(12) United States Patent
Nakai

(10) Patent No.: US 11,135,013 B2
(45) Date of Patent: Oct. 5, 2021

(54) ROOT CANAL TREATING DISPLAY DEVICE, ROOT CANAL TREATING UNIT, AND DENTAL IMAGE DISPLAY METHOD

(71) Applicant: J. MORITA MFG. CORP., Kyoto (JP)

(72) Inventor: Teruji Nakai, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 1174 days.

(21) Appl. No.: 15/357,355

(22) Filed: Nov. 21, 2016

(65) Prior Publication Data

US 2017/0065370 A1   Mar. 9, 2017

Related U.S. Application Data

(63) Continuation of application No. PCT/JP2015/064607, filed on May 21, 2015.

(30) Foreign Application Priority Data

May 21, 2014 (JP) .............................. JP2014-105572

(51) Int. Cl.
*A61B 34/10* (2016.01)
*A61B 6/03* (2006.01)
(Continued)

(52) U.S. Cl.
CPC ............ *A61B 34/10* (2016.02); *A61B 5/0036* (2018.08); *A61B 5/0059* (2013.01);
(Continued)

(58) Field of Classification Search
CPC ..... A61B 34/10; A61B 5/0059; A61B 5/0066; A61B 5/0088; A61B 5/055; A61B 5/4542;
(Continued)

(56) References Cited

U.S. PATENT DOCUMENTS 5,343,391 A * 8/1994 Mushabac .............. A61C 9/008
433/76
5,980,248 A * 11/1999 Kusakabe ............ A61C 1/0007
433/131
(Continued)

FOREIGN PATENT DOCUMENTS

EP   2 774 543 A1   9/2014
EP   3 153 129 A1   4/2017
(Continued)

OTHER PUBLICATIONS

Iida, Masato, (JP 2011030637 A), Machine translation of specfication. (Year: 2011).*
(Continued)

*Primary Examiner* — Nicholas D Lucchesi
*Assistant Examiner* — Mirayda A Aponte
(74) *Attorney, Agent, or Firm* — Oblon, McClelland, Maier & Neustadt, L.L.P.

(57) ABSTRACT

A root canal treatment information apparatus includes circuitry which stores three-dimensional information including information on a root canal of teeth in a storage, the three-dimensional information being acquired by an X-ray CT image capturing device, specify a tooth as a target of interest, generate a tooth image of the tooth, instruct display of the tooth image on a display, generate, based on the three-dimensional information, a root canal extension direction image showing a root canal extension direction along the root canal of the tooth, and instruct display of the root canal extension direction image on the display as overlapping, and in correspondence with, the tooth image.

25 Claims, 19 Drawing Sheets

(51) Int. Cl.
- *A61B 6/14* (2006.01)
- *A61B 5/00* (2006.01)
- *A61B 6/00* (2006.01)
- *A61C 1/00* (2006.01)
- *A61C 19/04* (2006.01)
- *A61C 9/00* (2006.01)
- *A61B 5/055* (2006.01)
- *A61C 5/42* (2017.01)
- *A61C 3/02* (2006.01)
- *A61B 90/00* (2016.01)

(52) U.S. Cl.
CPC .......... *A61B 5/0066* (2013.01); *A61B 5/0088* (2013.01); *A61B 5/055* (2013.01); *A61B 5/4542* (2013.01); *A61B 5/682* (2013.01); *A61B 6/03* (2013.01); *A61B 6/14* (2013.01); *A61B 6/463* (2013.01); *A61B 6/466* (2013.01); *A61B 6/5247* (2013.01); *A61C 1/0015* (2013.01); *A61C 3/02* (2013.01); *A61C 5/42* (2017.02); *A61C 9/0053* (2013.01); *A61C 19/041* (2013.01); *A61B 2034/107* (2016.02); *A61B 2090/376* (2016.02); *G06T 2207/10081* (2013.01); *G06T 2207/30036* (2013.01)

(58) Field of Classification Search
CPC ......... A61B 5/682; A61B 5/4836; A61B 6/03; A61B 6/14; A61B 6/463; A61B 6/466; A61B 6/5247; A61B 2034/107; A61B 2090/376; A61C 1/0015; A61C 3/02; A61C 9/0053; A61C 19/041; A61C 19/04; A61C 5/02; G06T 2207/10081; G06T 2207/00; G06T 2207/30036; G06T 1/0007
USPC .................... 382/128–134; 600/109; 396/16; 345/418–689, 947–960; 348/66; 713/100; 433/27–29, 215–224; 356/736, 356/247
See application file for complete search history.

(56) References Cited

U.S. PATENT DOCUMENTS

| | | | |
|---|---|---|---|
| 2008/0090199 A1* | 4/2008 | Noguchi | A61B 5/0066 433/29 |
| 2010/0161955 A1* | 6/2010 | Helfenbein | G05B 19/182 713/100 |
| 2013/0171580 A1 | 7/2013 | Van Lierde et al. | |
| 2013/0172731 A1 | 7/2013 | Gole | |
| 2014/0141385 A1* | 5/2014 | Taub | A61C 3/02 433/27 |
| 2014/0322664 A1* | 10/2014 | Van Lierde | G06T 19/20 433/72 |
| 2014/0342301 A1 | 11/2014 | Fleer et al. | |
| 2017/0071713 A1 | 3/2017 | Nakai | |

FOREIGN PATENT DOCUMENTS

| | | | |
|---|---|---|---|
| JP | 2001-051593 A | | 2/2001 |
| JP | 2001-51593 A | | 2/2001 |
| JP | 2006-305203 A | | 11/2006 |
| JP | 2009-153785 A | | 7/2009 |
| JP | 2010-068905 A | | 4/2010 |
| JP | 2010-68905 A | | 4/2010 |
| JP | 2010-533008 A | | 10/2010 |
| JP | 2011-30637 A | | 2/2011 |
| JP | 2011-030637 A | | 2/2011 |
| JP | 2011030637 A | * | 2/2011 |
| JP | 2012-096080 A | | 5/2012 |
| JP | 2013-519479 A | | 5/2013 |
| JP | 2013-172839 A | | 9/2013 |
| JP | 2014-520637 A | | 8/2014 |
| JP | 2014-171488 A | | 9/2014 |
| JP | 2014-236957 A | | 12/2014 |
| WO | WO 2012/155998 A1 | | 11/2012 |
| WO | WO 2013/010138 A2 | | 1/2013 |

OTHER PUBLICATIONS

International Search Report dated Aug. 11, 2015 in PCT/JP2015/064607 filed May 21, 2015.

Office Action dated May 19, 2015 in Japanese Patent Application No. 2014-105572, filed May 21, 2014 (with English-language Translation).

Extended European Search Report dated Jan. 8, 2018, in Patent Application No. 15795760.6, 6 pages.

\* cited by examiner

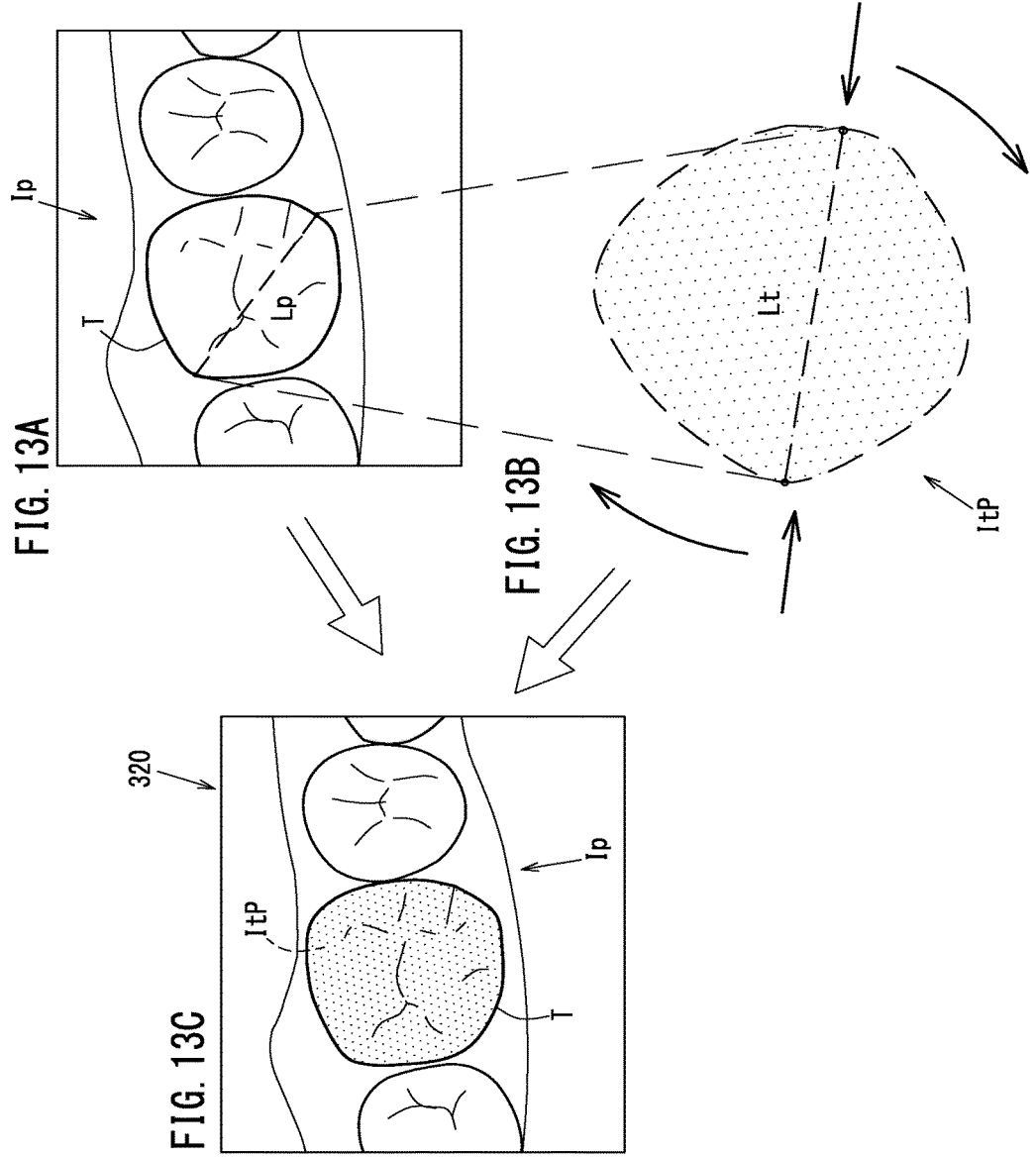

ROOT CANAL TREATING DISPLAY DEVICE, ROOT CANAL TREATING UNIT, AND DENTAL IMAGE DISPLAY METHOD

CROSS-REFERENCE TO RELATED APPLICATIONS

The present application is a continuation of and claims the benefit of priority to International Application No. PCT/JP2015/064607, filed May 21, 2015, which is based upon and claims the benefit of priority to Japanese Patent Application No. 2014-105572, filed May 21, 2014. The entire contents of these applications are incorporated herein by reference.

BACKGROUND OF THE INVENTION

Field of the Invention

The present invention relates to a root canal treating display device, a root canal treating unit and a dental image display method for displaying, for example, a tooth image created based on three-dimensional information on a tooth, including a root canal inside the tooth, acquired by an X-ray CT image capturing device or a tooth image captured by a visible light camera.

Description of Background Art

Japanese Laid-Open Patent Publication No. 2006-305203 describes a device for capturing a CT image. Japanese Laid-Open Patent Publication No. 2009-153785 describes a system for root canal treatment. Japanese Laid-Open Patent Publication No. 2012-96080 describes a guide system for guiding a cutting tool from the outside of a tooth crown to a root canal orifice inside a tooth. The entire contents of these publications are incorporated herein by reference.

SUMMARY OF THE INVENTION

According to one aspect of the present invention, a root canal treatment information apparatus includes circuitry which stores three-dimensional information including information on a root canal of teeth in a storage, the three-dimensional information being acquired by an X-ray CT image capturing device, specify a tooth as a target of interest, generate a tooth image of the tooth, instruct display of the tooth image on a display, generate, based on the three-dimensional information, a root canal extension direction image showing a root canal extension direction along the root canal of the tooth, and instruct display of the root canal extension direction image on the display as overlapping, and in correspondence with, the tooth image.

According to another aspect of the present invention, a dental image display method includes generating, based on three-dimensional information, a root canal extension direction image showing a root canal extension direction along a root canal of a tooth by a root canal treatment information apparatus including circuitry which stores the three-dimensional information including information on the root canal of teeth in a storage, the three-dimensional information being acquired by an X-ray CT image capturing device, specifies the tooth as a target of interest, generates a tooth image of the tooth, and instructs display of the tooth image on a display, and displaying the root canal extension direction image on the display as overlapping, and in correspondence with, the tooth image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 13A, 13B and 13C show a two-dimensional captured image and a two-dimensional converted image displayed in an overlapping manner;

DETAILED DESCRIPTION OF THE EMBODIMENTS

Figure 1:
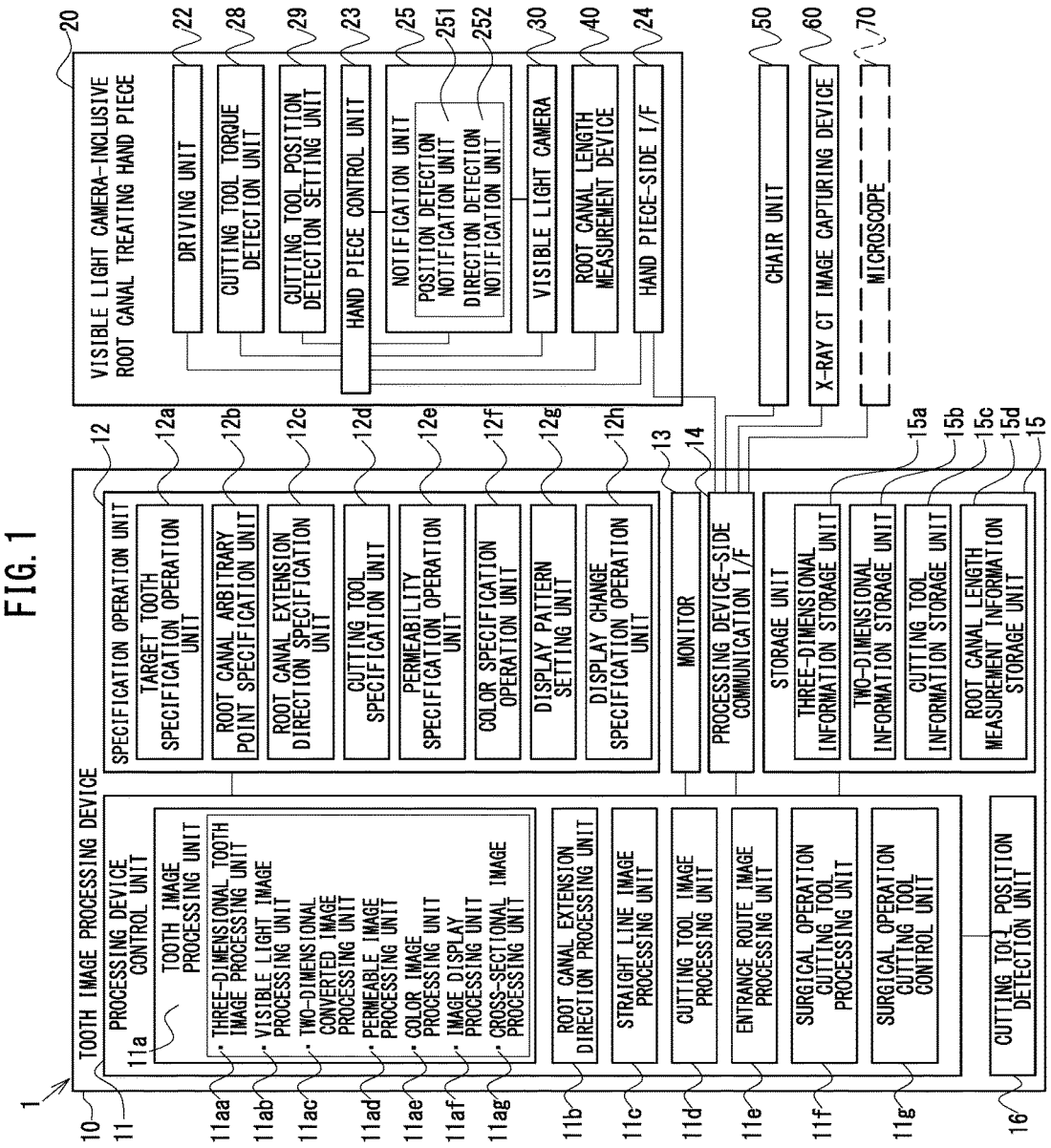
FIG. 1 is a block diagram of a medical care system according to an embodiment of the present invention.

The embodiments will now be described with reference to the accompanying drawings, wherein like reference numerals designate corresponding or identical elements throughout the various drawings.

Figure 2:
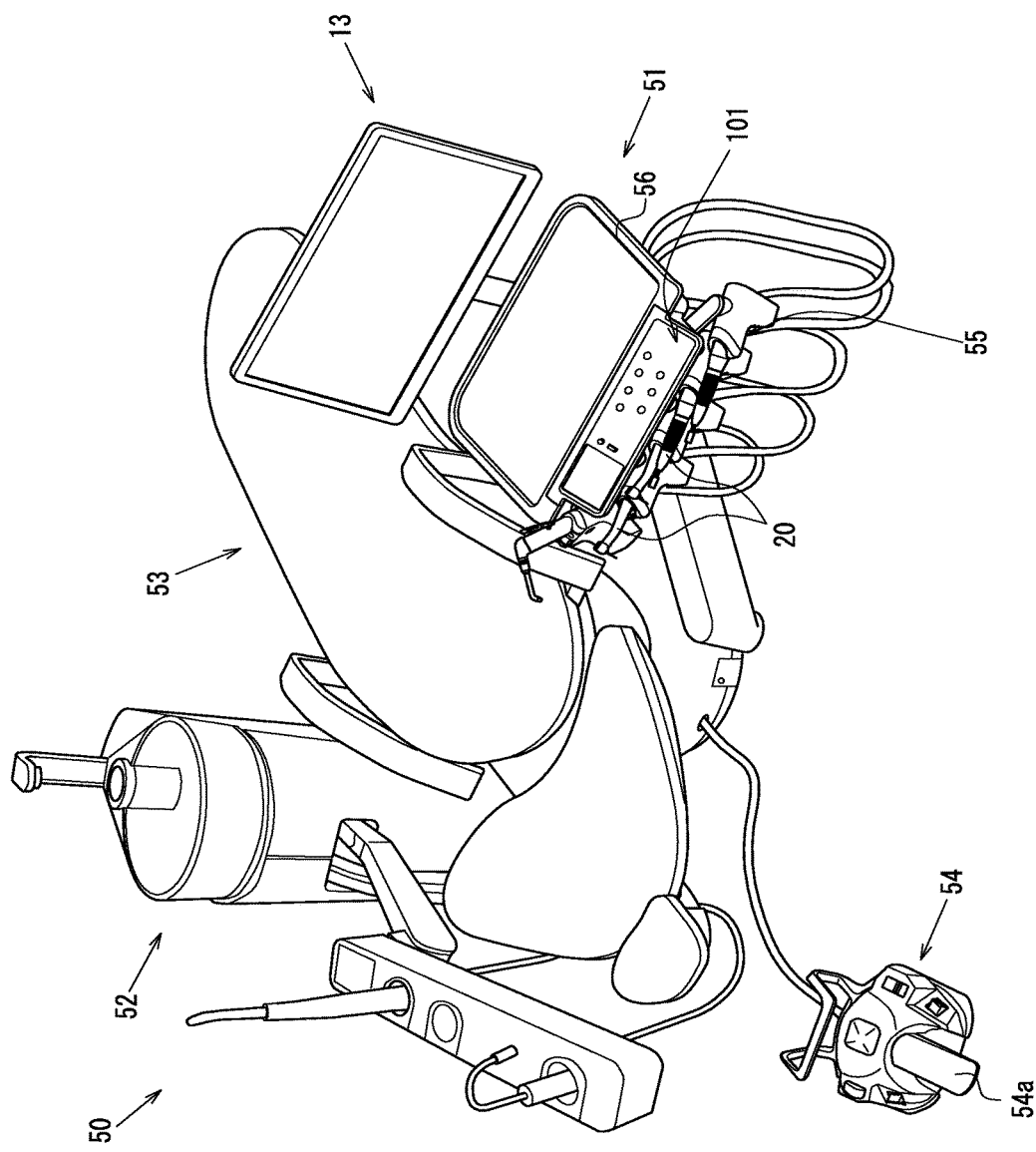
FIG. 2 is a schematic isometric view of the medical care system.
Figure 3:
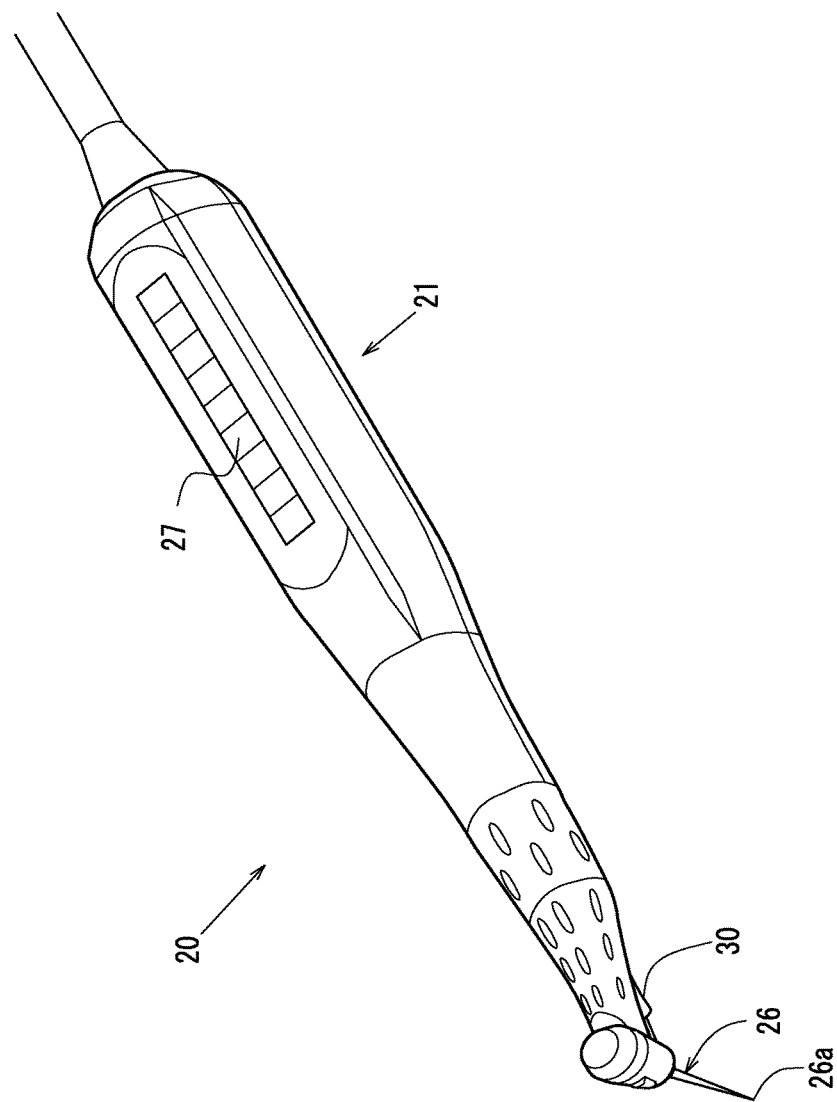
FIG. 3 is a schematic isometric view of a visible light camera-inclusive root canal treating hand piece.
Figure 4:
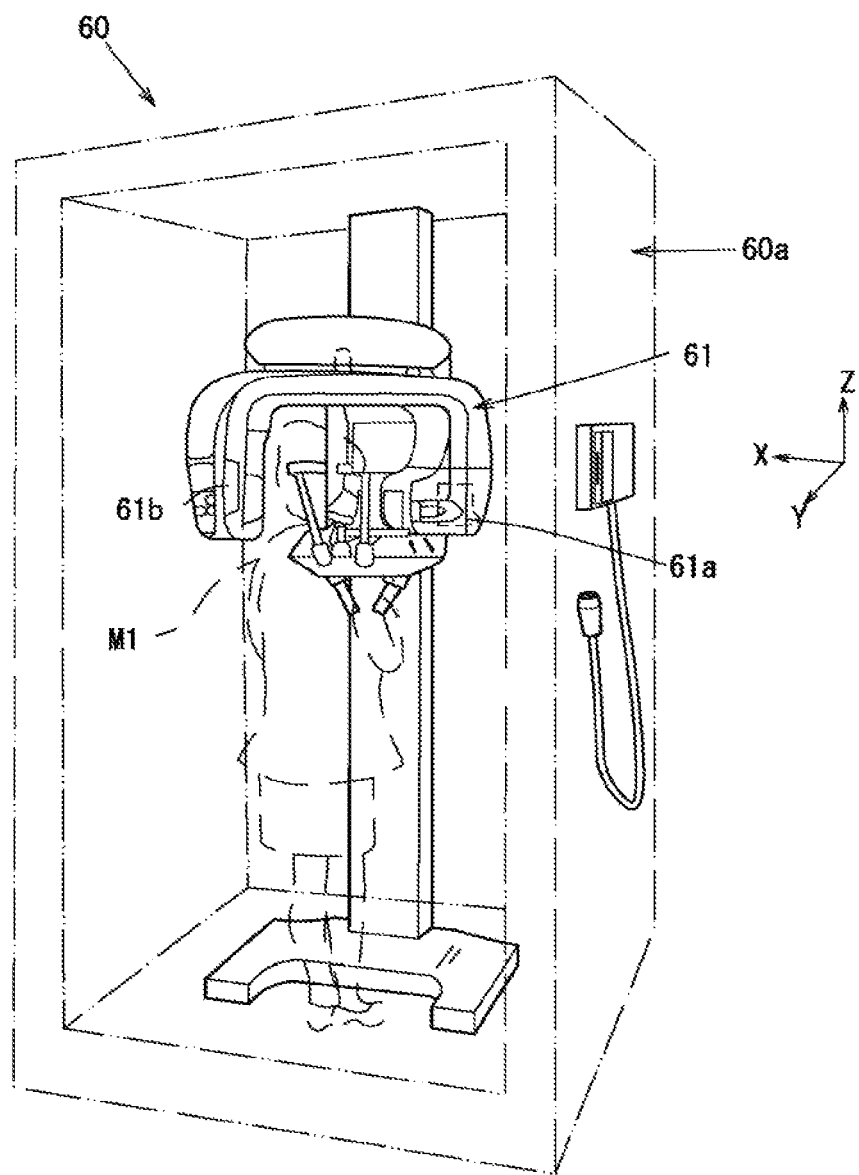
FIG. 4 is a schematic view of an X-ray CT image capturing device.
Figure 5:
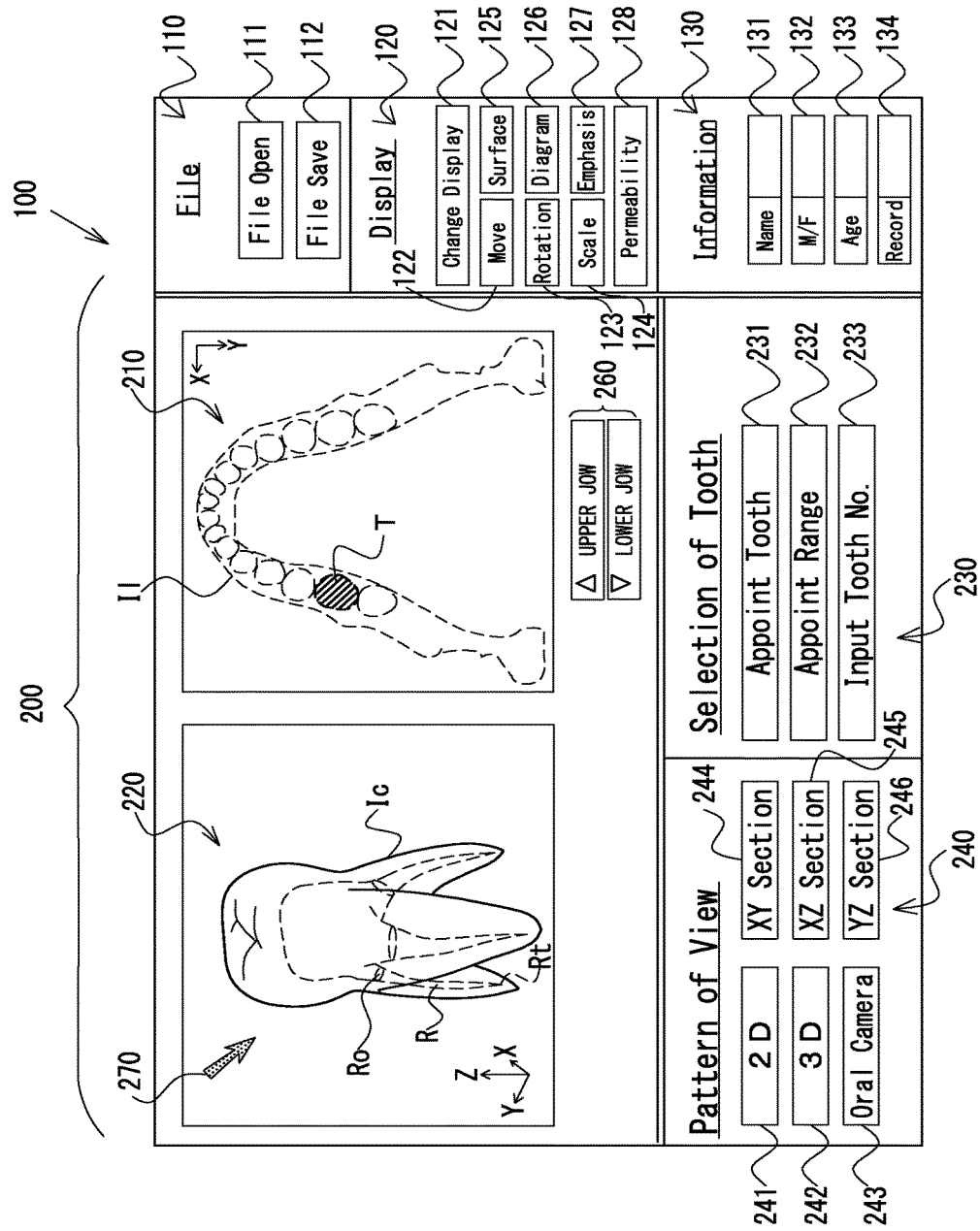
FIG. 5 shows a selected tooth image display operation screen.
Figure 6:
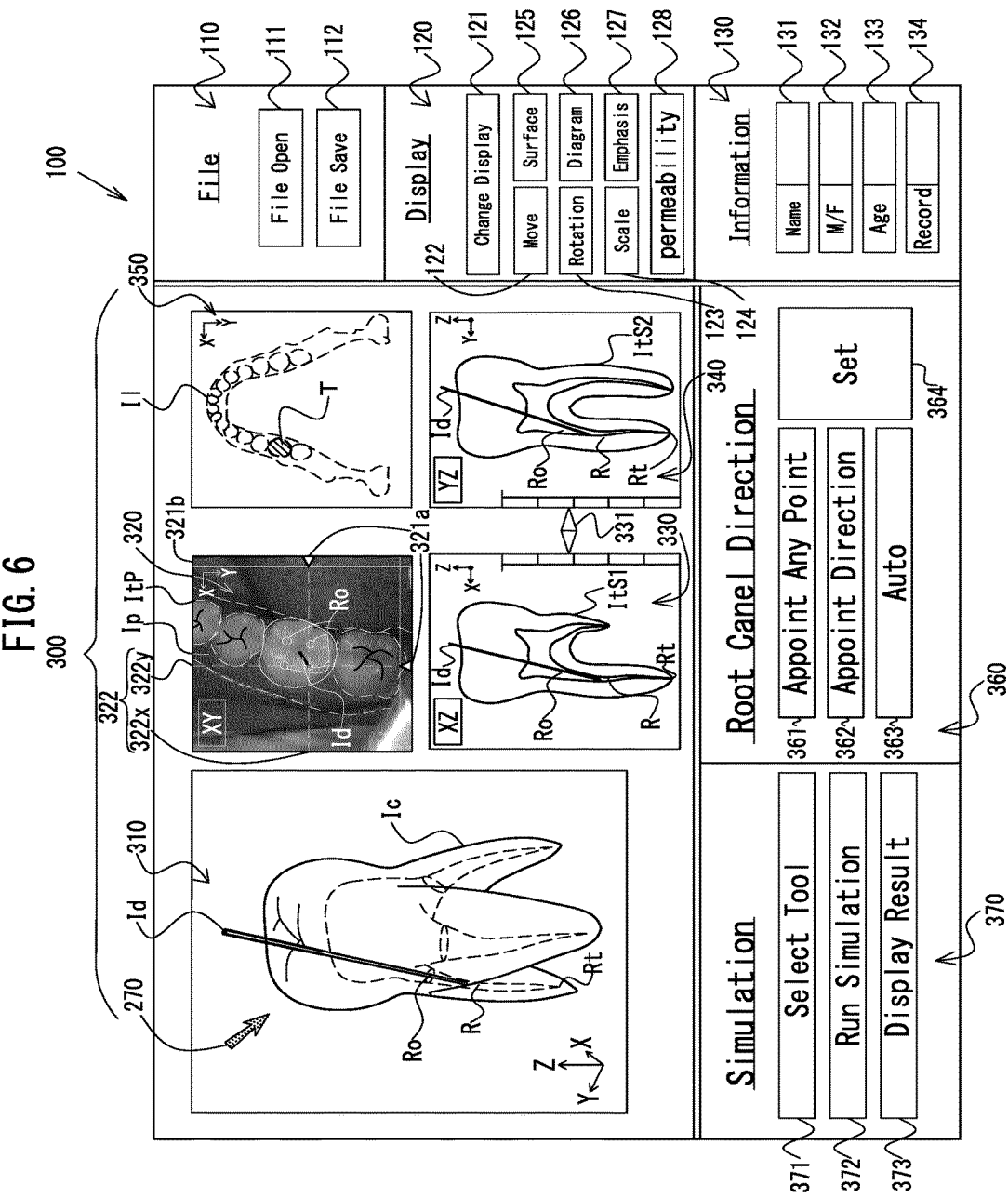
FIG. 6 shows a root canal extension direction display operation screen in an example.
Figure 7:
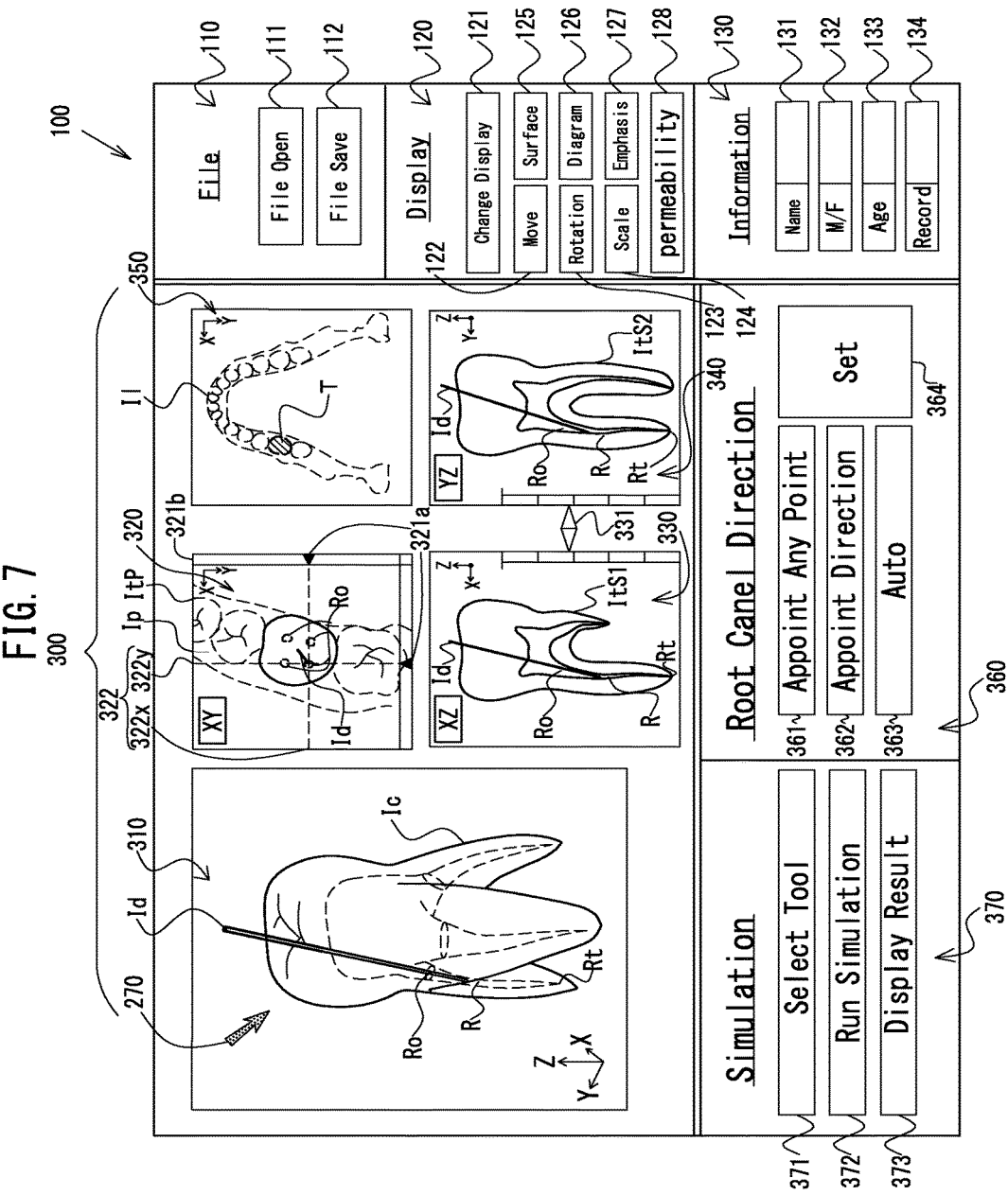
FIG. 7 shows a root canal extension direction display operation screen in another example.
Figure 8:
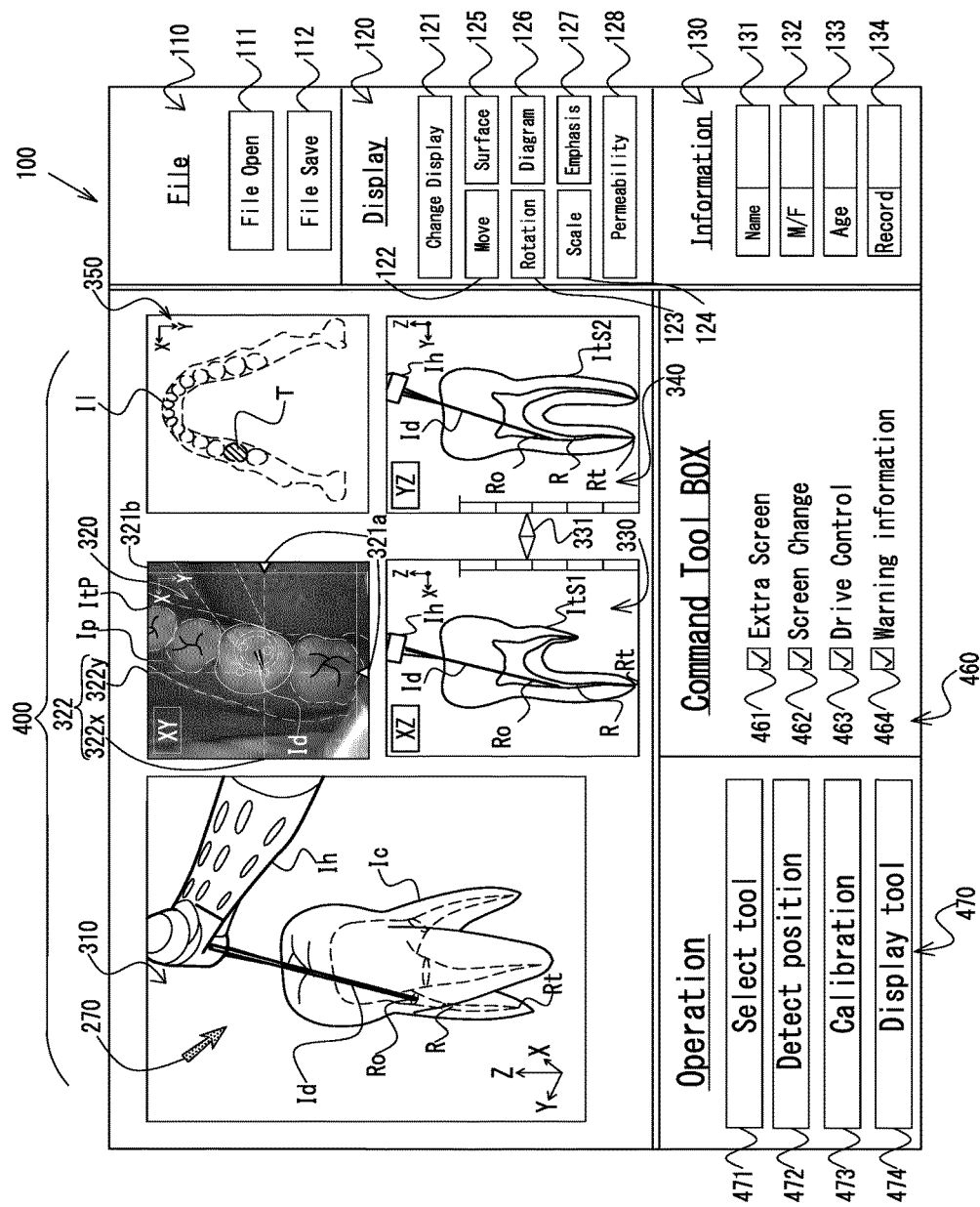
FIG. 8 shows a surgery operation screen.

Hereinafter, a medical care system 1 according to an embodiment of the present invention is described with reference to FIG. 1 through FIG. 19. FIG. 1 is a block diagram of the medical care system 1. FIG. 2 is a schematic isometric view of the medical care system 1. FIG. 3 is a schematic isometric view of a visible light camera-inclusive root canal treating hand piece 20. FIG. 4 is a schematic view of an X-ray CT image capturing device 60. FIG. 5 shows a selected tooth image display operation screen 200. FIG. 6 shows a root canal extension direction display operation screen 300 in an example. FIG. 7 shows a root canal extension direction display operation screen 300 in another example. FIG. 8 shows a surgery operation screen 400. In FIG. 2, the X-ray CT image capturing device 60 is omitted.

Figure 9:
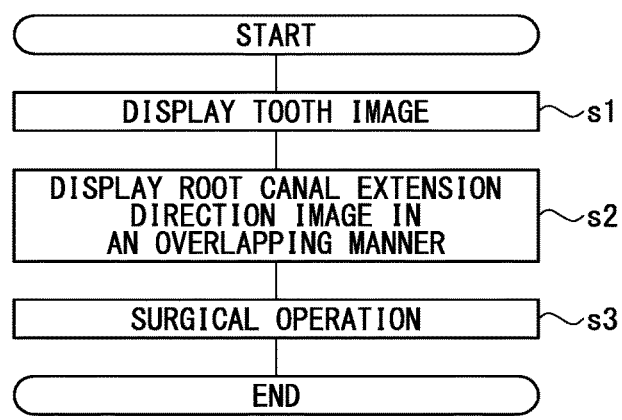
FIG. 9 is a flowchart schematically showing a process of a medical care performed on a root canal.
Figure 10:
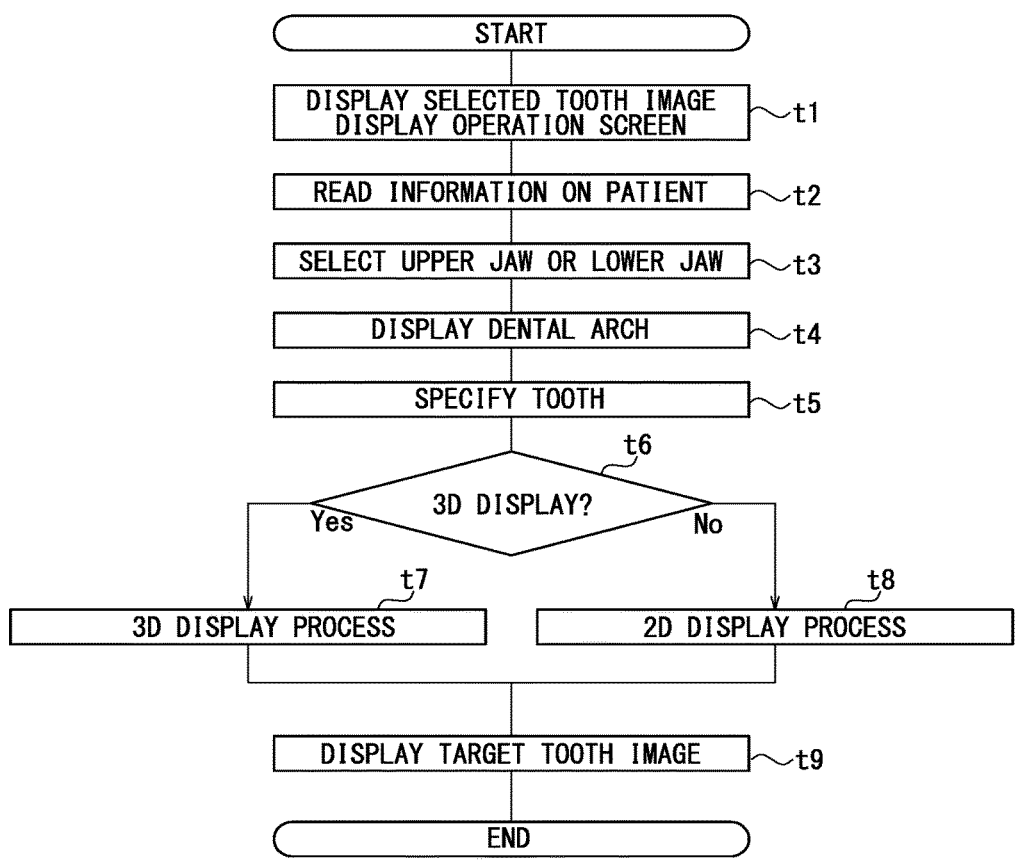
FIG. 10 is a flow chart of a process of displaying an image of a tooth.
Figure 11:
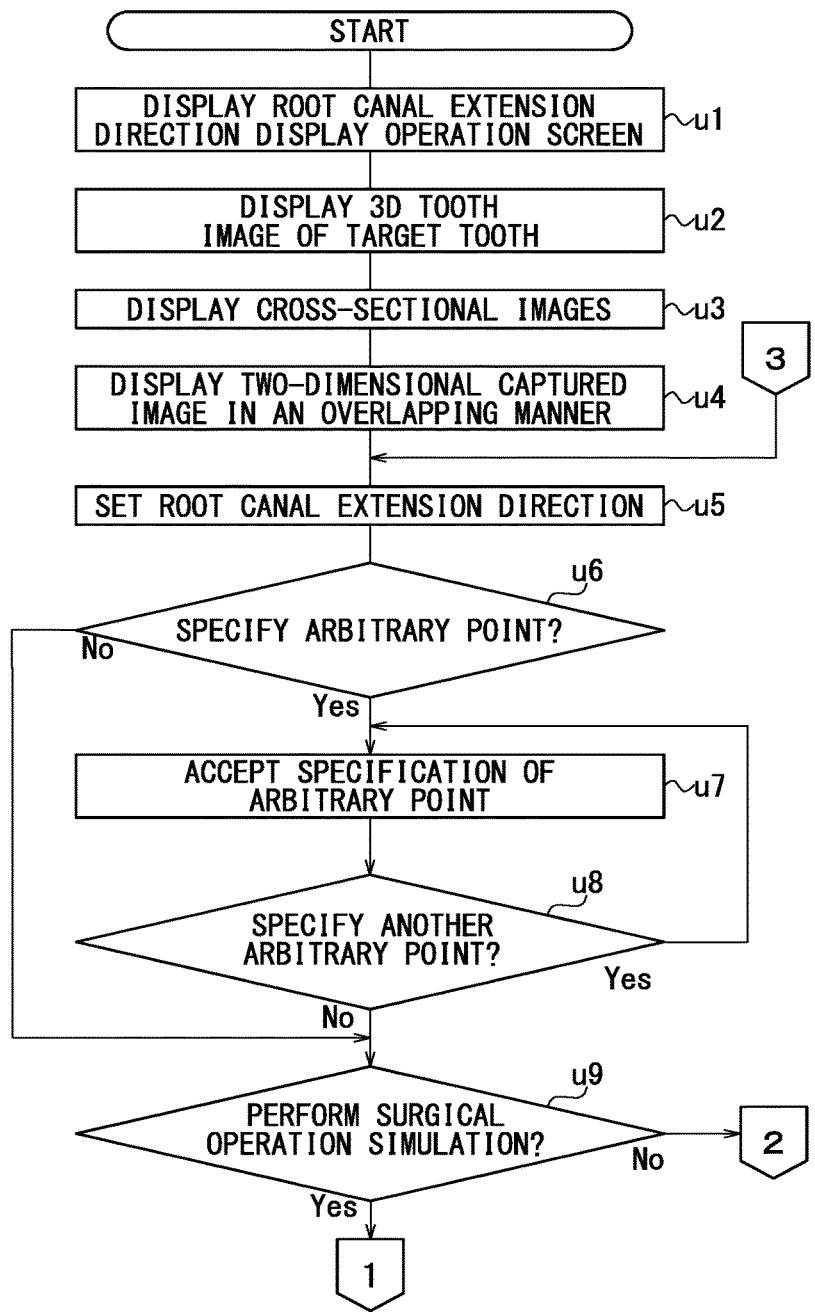
FIG. 11 is a flow chart of a process of displaying an image showing a root canal extension direction.
Figure 12:
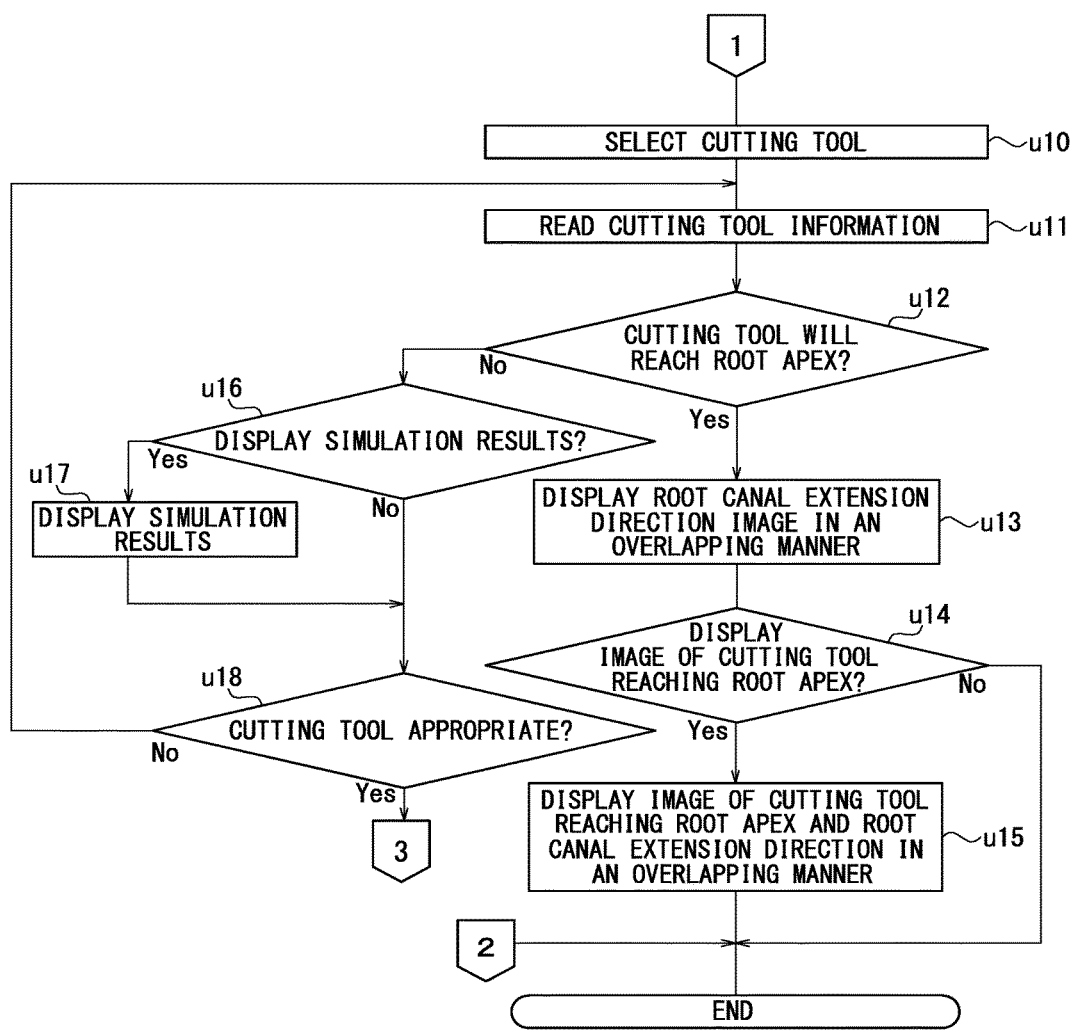
FIG. 12 is a flowchart of the process of displaying the image showing the root canal extension direction.
Figure 14A:
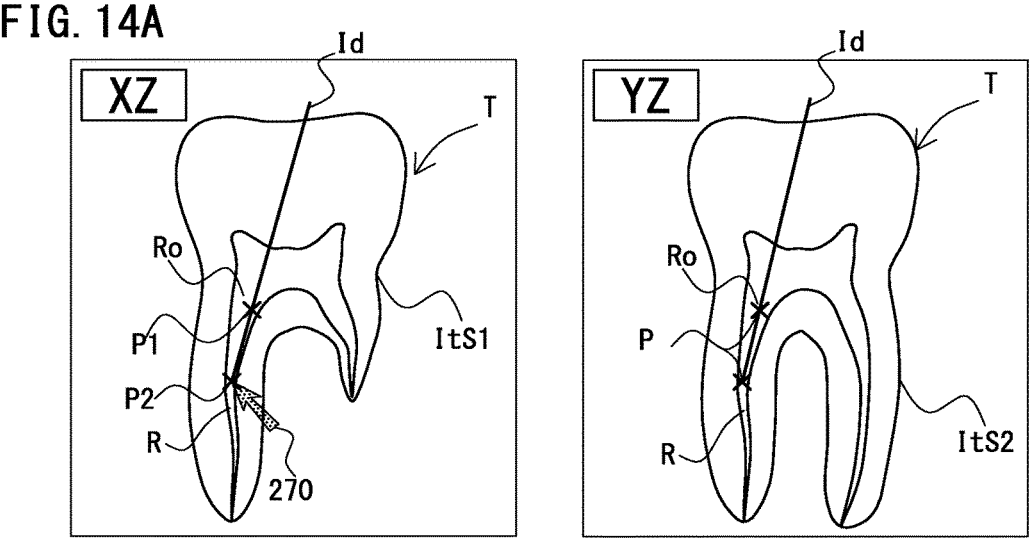
FIGS. 14A and 14B show a method for specifying the root canal extension direction.
Figure 14B:
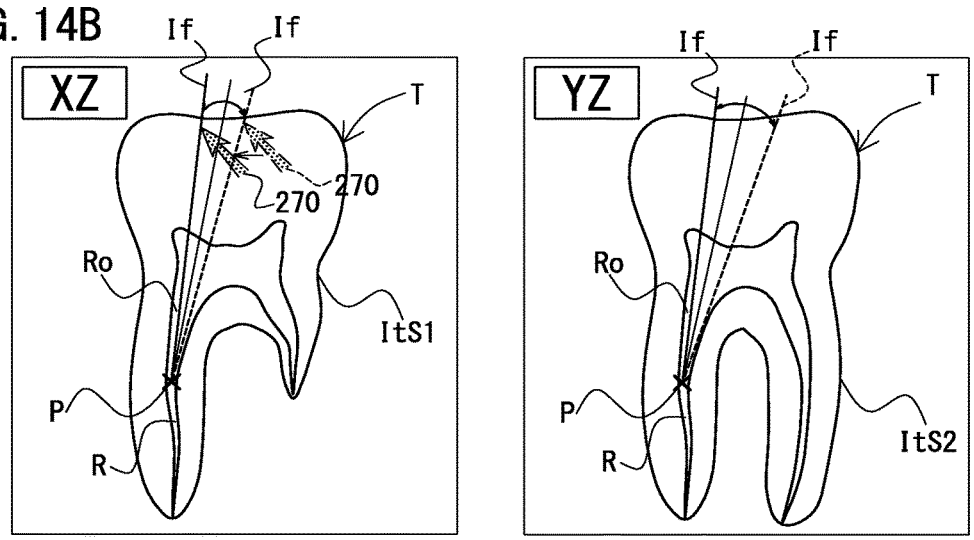
Figure 15:
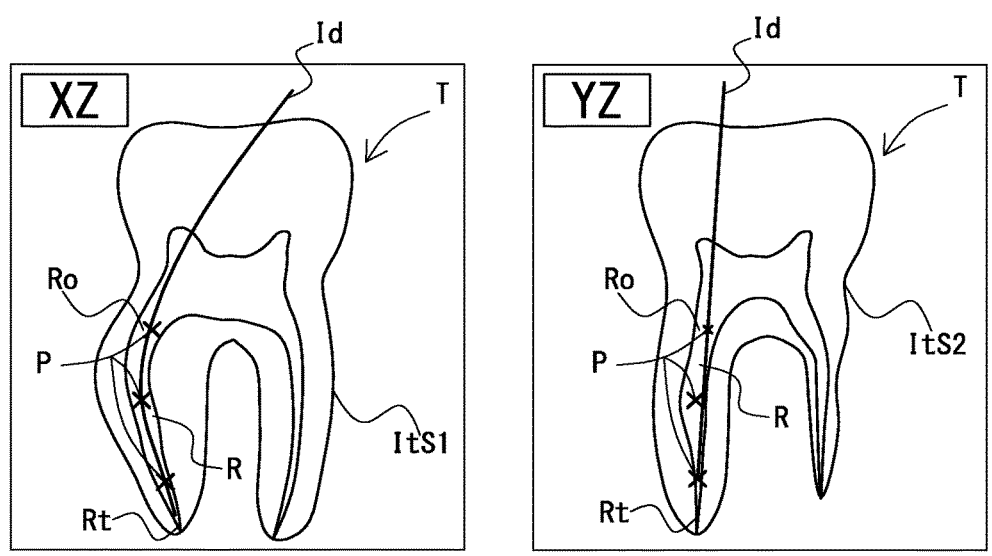
FIG. 15 shows a method for specifying the root canal extension direction.
Figure 16:
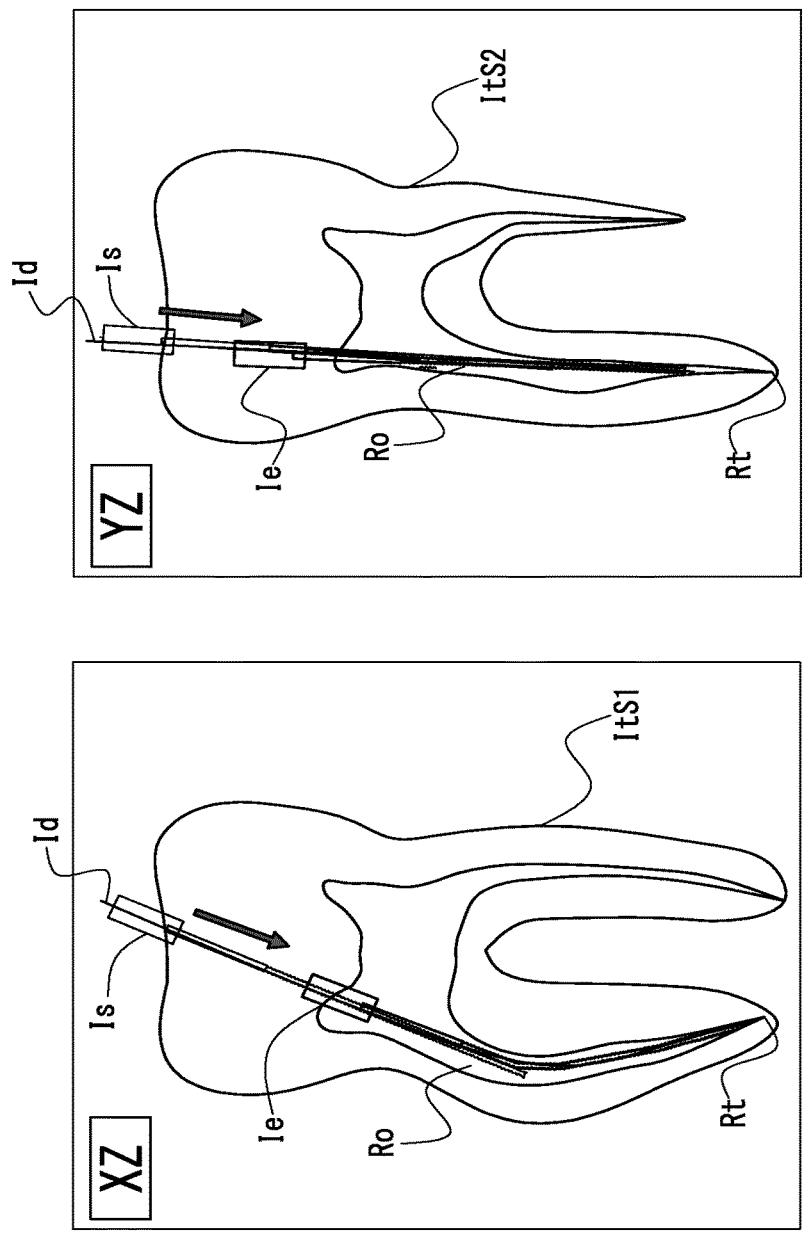
FIG. 16 shows an entrance route image.
Figure 17:
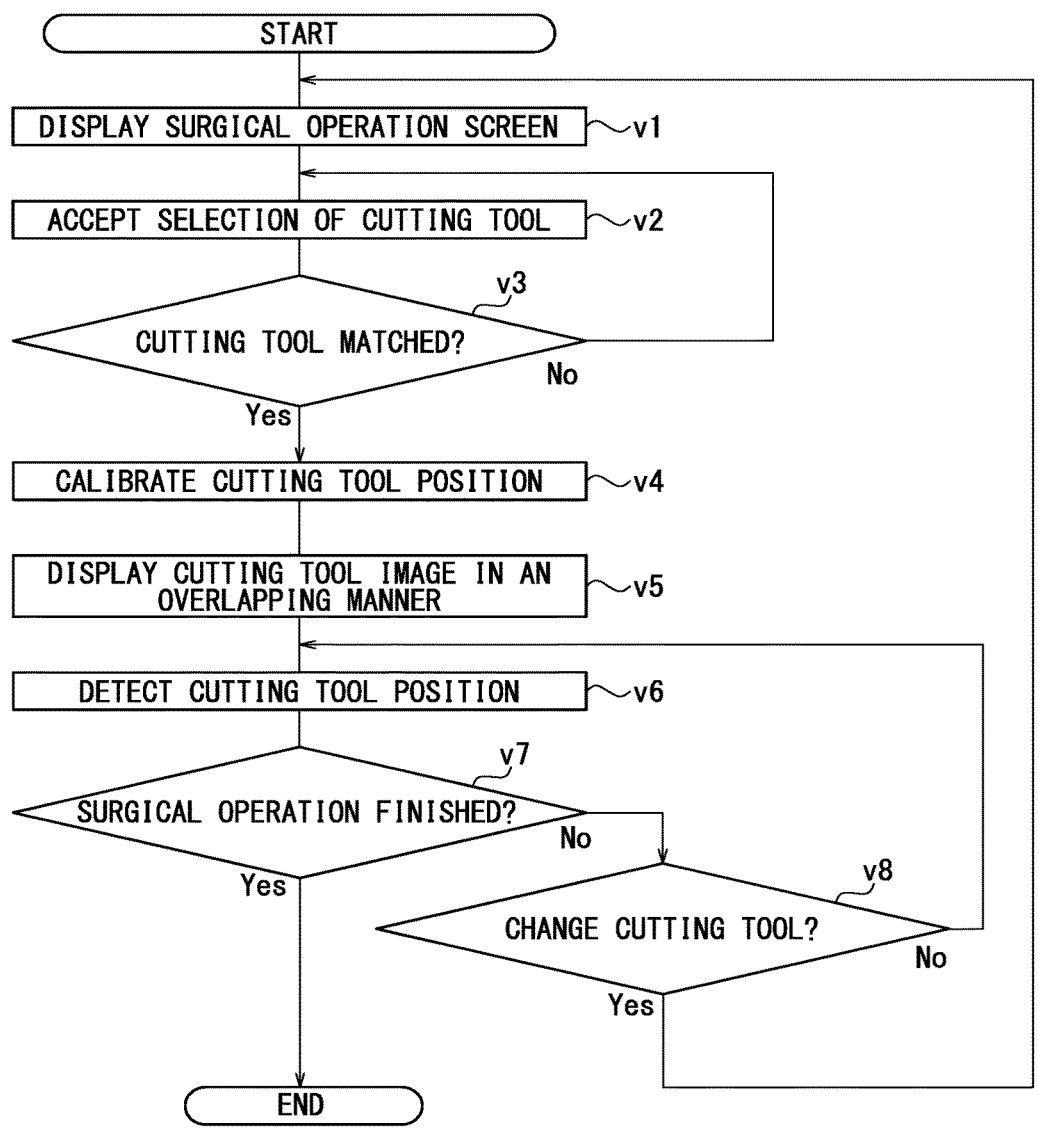
FIG. 17 is a flowchart showing a process of a surgical operation.
Figure 18A:
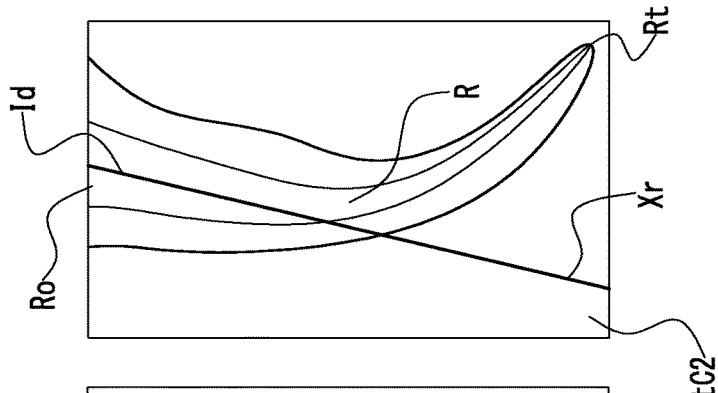
FIGS. 18A, 18B and 18C shows root canal cross-sectional images.
Figure 18B:
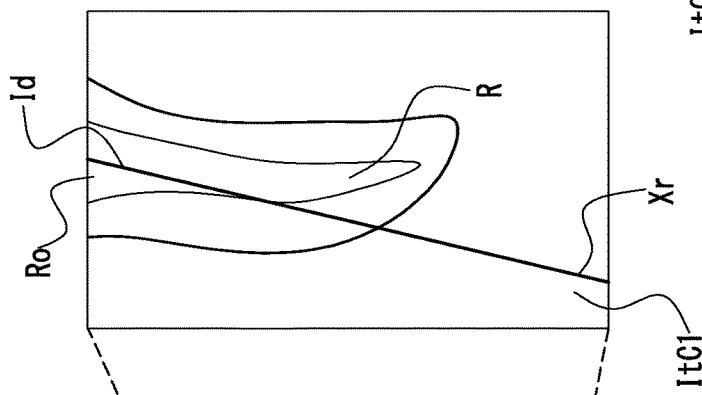
Figure 18C:
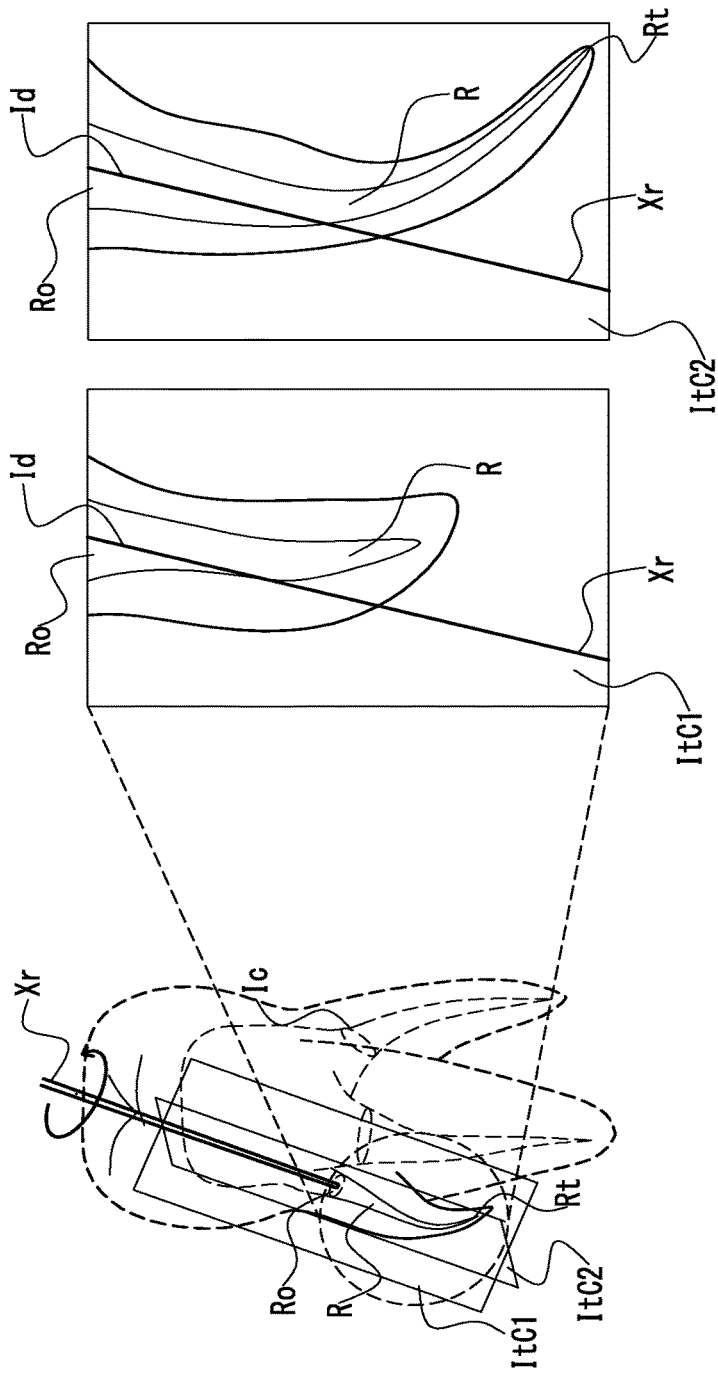
Figure 19:
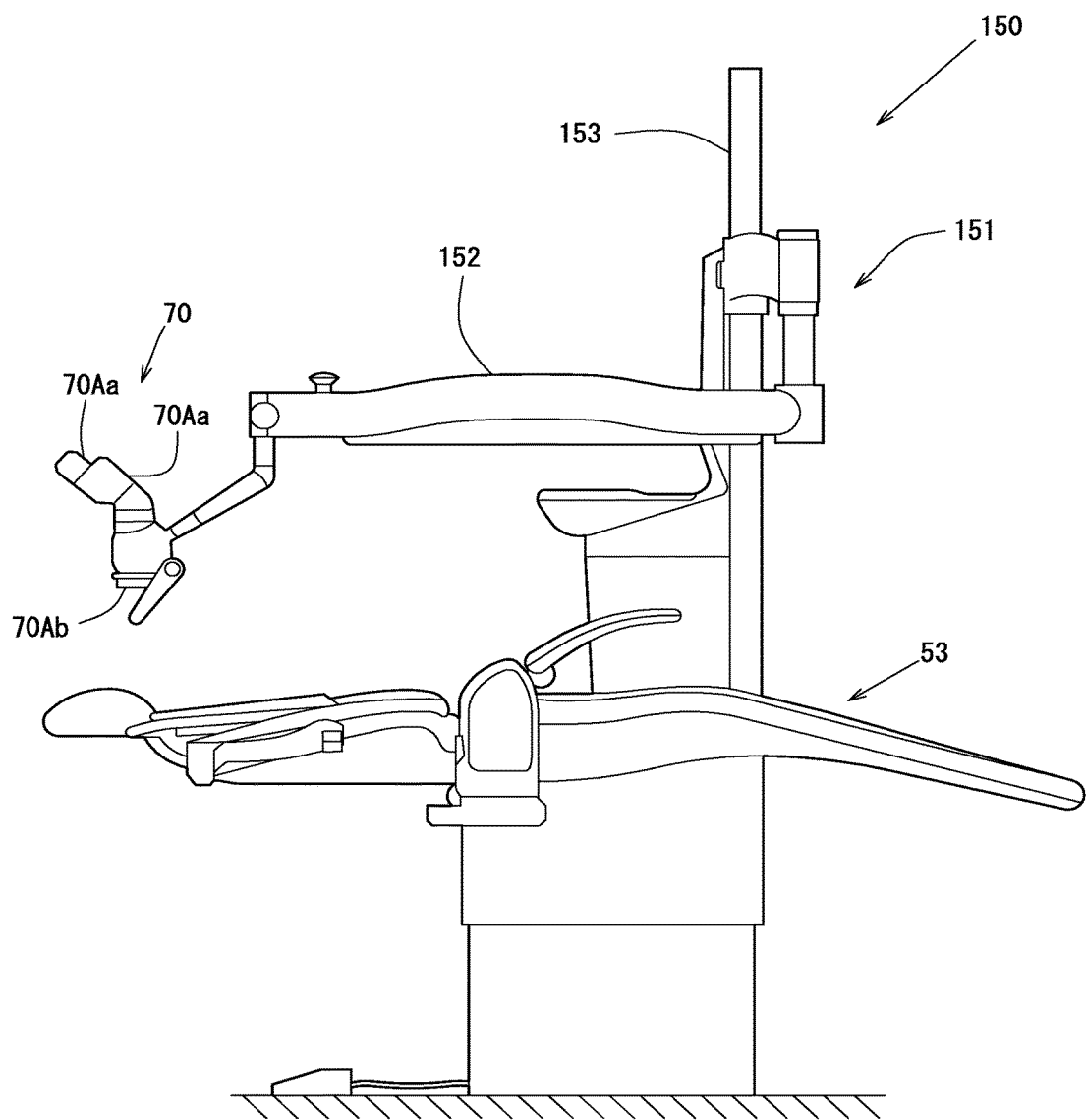
FIG. 19 shows a microscope-inclusive dental care table.

FIG. 9 is a flowchart schematically showing a process of a medical care performed on a root canal (R). FIG. 10 is a flowchart of a process of displaying an image of a tooth (T). FIG. 11 and FIG. 12 are a flowchart of a process of displaying an image showing a root canal extension direction. FIGS. 13A, 13B and 13C show a two-dimensional captured image (Ip) and a two-dimensional converted image (ItP) displayed in an overlapping manner. FIGS. 14A and 14B and FIG. 15 each show a method for specifying the root canal extension direction. FIG. 16 shows an entrance route image (Ie). FIG. 17 is a flowchart showing a process of a surgical operation. FIGS. 18A, 18B and 18C show root canal cross-sectional images ItC. FIG. 19 shows a microscope-inclusive dental care table 150.

As shown in FIG. 1, the medical care system 1 includes a tooth image processing device 10, the visible light camera-inclusive root canal treating hand piece 20, a chair unit 50, and the X-ray CT image capturing device 60.

The tooth image processing device 10 includes a processing device control unit 11, a specification operation unit 12, a monitor 13, a processing device-side communication interface 14 (hereinafter, referred to as the "processing device-side communication I/F 14"), a storage unit 15, and a cutting tool position detection unit 16.

The processing device control unit 11 includes a CPU, a ROM and a RAM. The processing device control unit 11 controls the monitor 13, the processing device-side communication I/F 14, the storage unit 15, and the cutting tool position detection unit 16 based on an operation signal input to the specification operation unit 12. The processing device control unit 11 includes functional units described below in detail.

The processing device control unit 11 includes a tooth image processing unit (11a), a root canal extension direction processing unit (11b), a straight line image processing unit (11c), a cutting tool image processing unit (11d), an entrance route image processing unit (11e), a surgical operation cutting tool processing unit (11f), and a surgical operation cutting tool control unit (11g).

The tooth image processing unit (11a) creates a tooth image (I) of the tooth (T), and displays the tooth image (I) on a tooth image operation screen 100 displayed on a monitor (described later).

The tooth image (I) may be a three-dimensional tooth image (Ic), a two-dimensional converted image (It), or the two-dimensional captured image (Ip), which is described later in detail.

The root canal extension direction processing unit (11b) creates a root canal extension direction image (Id) showing the root canal extension direction along the root canal (R), based on an arbitrary point (P) specified by a root canal arbitrary point specification unit (12b) (described later) and based on a direction specified by a root canal extension direction specification unit (12c) (described later). The root canal extension direction processing unit (11b) displays the root canal extension direction image (Id) on the monitor 13 in correspondence with the tooth image (I) (see FIG. 6). The arbitrary point (P) and the direction are specified based on three-dimensional information acquired by the X-ray CT image capturing device 60.

The root canal extension direction is a direction along the root canal (R). The root canal extension direction may be a direction that extends from a root apex (Rt) toward the outside of a tooth crown through a root canal orifice (Ro), a direction that extends from the root apex orifice (Ro), which is an end of the root canal (R) toward the outside of the tooth crown, or a direction that extends toward the root apex (Rt). The "direction that extends toward the root apex (Rt)" may be rephrased as a direction that extends from an end of a cutting tool 26 usable for a root canal treatment toward the root apex (Rt).

The straight line image processing unit (11c) displays a straight line image (If) based on the arbitrary point (P) specified by the root canal arbitrary point specification unit (12b) (described later) on the monitor 13 in correspondence with the tooth image (I) (see FIG. 14B).

The cutting tool image processing unit (11d) displays a cutting tool image (Is) of a cutting tool 26 specified by a cutting tool specification unit (12d) (described later) on the monitor 13 (see FIG. 16).

The entrance route image processing unit (11e) operates as follows. When the cutting tool 26 specified by the cutting tool specification unit (12d) (described later) enters the root canal (R) from the root canal orifice (Ro) in the root canal extension direction, the entrance route image processing unit (11e) determines whether or not a cutting tool tip (26a) of the cutting tool 26 is capable of reaching the root apex (Rt) of the root canal (R). The entrance route image processing unit (11e) creates the entrance route image (Ie) based on the determination result, and displays the entrance route image (Ie) on the monitor 13 in correspondence with the two-dimensional converted image (It) (see FIG. 16).

The surgical operation cutting tool processing unit (11f) determines whether or not a cutting tool 26 to be used for the surgical operation corresponds to the cutting tool 26 specified during a simulation. The surgical operation cutting tool processing unit 11f displays a cutting tool image (Ih) of the cutting tool 26 on the monitor 13 at a position detected by the cutting tool position detection unit 16 (described later) based on information on the cutting tool 26 stored on a cutting tool information storage unit (15c) (described later) (see FIG. 8).

The surgical operation cutting tool control unit (11g) operates as follows. When, for example, the cutting tool tip (26a) of the cutting tool 26 detected by the cutting tool position detection unit 16 (described later) is deviated from a certain range that is set based on the root canal extension direction, the surgical operation cutting tool control unit (11g) controls such that a control signal usable to control the drive on the visible light camera-inclusive root canal treating hand piece 20 is transmitted from the tooth image processing device 10 to the visible light camera-inclusive root canal treating hand piece 20 via a communication cable.

The tooth image processing unit (11a) includes a three-dimensional tooth image processing unit (11aa), a visible light image processing unit (11ab), a two-dimensional converted image processing unit (11ac), a permeable image processing unit (11ad), a color image processing unit (11ae), an image display processing unit (11af), and a cross-sectional image processing unit (11ag).

The three-dimensional tooth image processing unit (11aa) creates the three-dimensional tooth image (Ic) of the tooth (T) based on the three-dimensional information (hereinafter, referred to as the "3D information") acquired by the X-ray CT image capturing device 60. As shown in, for example, FIG. 5, the three-dimensional tooth image processing unit (11aa) displays the three-dimensional tooth image (Ic), for example, a target tooth image display area 220 of the selected tooth image display operation screen 200 (described later).

The visible light image processing unit (11ab) creates the two-dimensional captured image (Ip) based on information acquired by a visible light camera 30. As shown in, for example, FIG. 6, the visible light image processing unit (11ab) displays the two-dimensional captured image (Ip) in an XY plane root canal extension direction display area 320, which is included in the root canal extension direction display operation screen 300. The two-dimensional converted image processing unit (11ac) creates the two-dimensional converted image (It), which is a two-dimensional image, based on the 3D information acquired by the X-ray CT image capturing device 60, and displays the two-dimensional converted image (It) in, for example, the XY plane root canal extension direction display area 320 of the root canal extension direction display operation screen 300 (see FIG. 7).

The permeable image processing unit (11ad) creates a permeable tooth image (not shown) adjusted to have a desired permeability level by a permeability specification operation unit (12e) (described later). The color image processing unit (11ae) creates a color tooth image (not shown) of a specified tooth (T) that is colored by a color specification operation unit (12f) (described later).

The image display processing unit (11af) displays any of the above-described images in the state of, for example, being rotated, enlarged, contracted, emphasized or moved, or displays any of the above-described images in correspondence with a different image, in an appropriate display area. The cross-sectional image processing unit (11ag) creates, and displays in an appropriate display area, the root canal cross-sectional image (ItC). The root canal cross-sectional image (ItC) is of a plane including the root canal extension direction that extends along the root canal (R) in a straight manner from the outside of the tooth crown through the root canal orifice (Ro). The root canal cross-sectional image (ItC) is also rotatable about a root canal extension axis direction (D).

The specification operation unit 12 includes, as functional units, a target tooth specification operation unit (12a), the root canal arbitrary point specification unit (12b), the root canal extension direction specification unit (12c), the cutting tool specification unit (12d), the permeability specification operation unit (12e), the color specification operation unit (12f), a display pattern setting unit (12g), and a display change specification operation unit (12h).

The target tooth specification operation unit (12a) accepts an operation of specifying a tooth (T) as a target of interest from an image showing a dental arch that is displayed in a dental arch image display area 210 (described later) shown in FIG. 5, and is usable to extract 3D information on the corresponding tooth (T) from multiple pieces of 3D information stored on a three-dimensional information storage unit (15a) (described later).

The root canal arbitrary point specification unit (12b) accepts an operation of, for example, specifying a point on the root canal (R) as the arbitrary point (P) in order to set the root canal extension direction (see FIG. 14A).

The root canal extension direction specification unit (12c) accepts an operation of specifying a direction that is along the root canal (R) and passes the root canal orifice (Ro), based on one arbitrary point (P) specified by use of the root canal arbitrary point specification unit (12b) (see FIG. 14B).

The cutting tool specification unit (12d) accepts an operation of specifying a cutting tool 26. The permeability specification operation unit (12e) accepts an operation of adjusting the permeability level of the entirety of, or a part of, images displayed on the monitor 13 in an overlapping manner. The color specification operation unit (12f) accepts an operation of specifying the color of the entirety of, or a part of, images displayed on the monitor 13 in an overlapping manner.

The display pattern setting unit (12g) sets a display pattern of the tooth image (I). For example, the display pattern setting unit (12g) changes the three-dimensional tooth image (Ic) (see FIG. 5) displayed in the target tooth image display area 220 (described later), which is in a main part of the tooth image operation screen 100 (described later) displayed on the monitor 13, into the two-dimensional converted image (ItP) as observed in an occlusal surface direction.

The display change specification operation unit (12h) accepts an operation of specifying a screen to be displayed on the monitor 13. Specifically, the display change specification operation unit (12h) accepts an operation of switching the operation screen to be provided in a main part of the tooth image operation screen 100 (described later) (see FIG. 5). The display change specification operation unit (12h) also accepts an operation of specifying that the three-dimensional tooth image (Ic) or the two-dimensional converted image It created based on the 3D information is to be displayed on the monitor 13 as a line drawing or a topographical view. In addition, the display change specification operation unit (12h) accepts an operation of moving, rotating, enlarging, contracting or emphasizing the image to be displayed.

The processing device-side communication I/F 14 is usable to cause the tooth image processing device 10 to communicate with a peripheral device such as the visible light camera-inclusive root canal treating hand piece 20 or the like via a communication cable.

The storage unit 15 includes an HDD, an SSD or the like, and includes functional units described below in detail.

The storage unit 15 includes the three-dimensional information storage unit (15a) that stores the 3D information acquired by the X-ray CT image capturing device 60, a two-dimensional information storage unit (15b) that stores the two-dimensional captured image (Ip) acquired by the visible light camera 30, a cutting tool information storage unit (15c) that stores information on the cutting tool 26, and a root canal length measurement information storage unit (15d) that stores root canal length measurement information, such as a root canal length or the like, measured by a root canal length measurement device 40. The storage unit 15 stores, for example, various processing programs usable to process an image by the processing device control unit 11, and information on a surgical operator or a patient as a target of surgical operation.

The cutting tool position detection unit 16 detects at least one of the position of the cutting tool tip (26a) of the cutting tool 26 attached to the visible light camera-inclusive root canal treating hand piece 20 (described later) and the inclination of the cutting tool 26. The detection may be performed by a detection method. For example, a three-dimensional position measurement marker detectable by an infrared detector or a magnetic sensor detectable by a three-dimensional magnetic detector may be attached to the visible light camera-inclusive root canal treating hand piece 20 (described later). Thus, the position of the cutting tool tip (26a) of the cutting tool 26 or the inclination of the cutting tool 26 attached to the visible light camera-inclusive root canal treating hand piece 20 is estimated.

As shown in FIG. 1 and FIG. 3, the visible light camera-inclusive root canal treating hand piece 20 (hereinafter, referred to as the "root canal treating hand piece"20") has the cutting tool 26, which is rotatable, attached to a head (21a) at a tip thereof. The cutting tool 26 is detachable from the head (21a). The root canal treating hand piece 20 includes a hand piece main body 21, a driving unit 22 such as a micromotor or the like that drives the cutting tool 26 to rotate, a hand piece control unit 23, a hand piece-side interface 24 (hereinafter, referred to as the hand piece-side I/F 24"), a notification unit 25, a cutting tool torque detection unit 28, and a cutting tool position detection setting unit 29. The driving unit 22, the hand piece control unit 23, the hand piece-side I/F 24, the notification unit 25, the cutting tool torque detection unit 28, and the cutting tool position detection setting unit 29 are accommodated in the hand piece main body 21. The root canal treating hand piece 20 also includes the root canal length measurement device 40 accommodated in the hand piece main body 21. The root canal treating hand piece 20 is connected to an oral cavity electrode (not shown) by a connection cable (not shown) attached to a rear end thereof. The root canal treating hand piece 20 includes the visible light camera 30 in a tip part of the head (21a), and also includes a measurement result display unit 27 that displays a measurement result acquired by the root canal length measurement device 40. The measurement result display unit 27 is provided on a top surface of a rear part of the hand piece main body 21.

The root canal treating hand piece 20 having the above-described structure is driven by the driving unit 22 via the hand piece control unit 23 provided inside the hand piece main body 21 to, for example, cut off a decayed part or a contaminated root canal wall of the tooth (T) as the target of surgical operation.

The processing device-side communication I/F 14 and the hand piece-side I/F 24 are connected to each other by a communication unit connection cable (not shown). Therefore, the root canal treating hand piece 20 is communicable with the tooth image processing device 10.

In this example, the root canal treating hand piece 20 and the tooth image processing device 10 communicate with each other by the cable. Alternatively, the root canal treating hand piece 20 and the tooth image processing device 10 may communicate with each other by use of wireless communication such as infrared communication or the like.

The notification unit 25 includes a position detection notification unit 251 and a direction detection notification unit 252, which make a notification in the form of, for example, a sound such as a buzzer or illumination.

The cutting tool torque detection unit 28 detects a torque value applied on the cutting tool 26. When the detected torque value exceeds a value preset by a torque setting unit (not shown), the hand piece control unit 23 performs a predetermined operation, namely, stops the rotation of the cutting tool 26, rotates the cutting tool 26 in a reverse direction, or decreases a force of driving the cutting tool 26. The cutting tool position detection setting unit 29 sets a predetermined position with respect to the root apex Rt. For example, at the time when the cutting tool tip (26a) is detected by the root canal length measurement device 40 to have reached the predetermined position set by the cutting tool position detection setting unit 29, the hand piece control unit 23 performs any of the above-described operations.

The visible light camera 30, which is an example of visible light image capturing device, is located in the head (21a) of the root canal treating hand piece 20 shown in FIG. 3. The visible light camera 30 operates as follows. Illumination light is directed from the head (21a), inserted into the oral cavity of a patient M1 (see FIG. 4), toward an image capturing target site as an area of interest, and the light reflected by the image capturing target site is received by a solid-state image capturing sensor (not shown) such as a CMOS or the like. Thus, the visible light camera 30 captures the two-dimensional captured image (Ip). The two-dimensional captured image (Ip) captured by the visible light camera 30 is stored on the two-dimensional information storage unit (15b) of the storage unit 15.

The root canal length measurement unit 40 is accommodated in, for example, the hand piece main body 21 of the root canal treating hand piece 20, and measures, based on an electrical current value, the position of the cutting tool tip (26a) of the cutting tool 26 with respect to the root apex (Rt) as a tip of the root canal (R) in the tooth (T). The root canal length measurement unit 40 supplies an electric current between the cutting tool 26 attached to the head (21a) and the oral cavity electrode (not shown), which is a hook-shaped electrode that is hooked at a corner of the mouth of the patient (M1), and measures the length of the root canal (R).

Specifically, the root canal length measurement unit 40 may operate in the following manner. The oral cavity electrode is hooked at a corner of the mouth of the patient (M1), while the cutting tool 26 is inserted into the root canal (R) of the tooth (T). The position of the cutting tool tip (26a) of the cutting tool 26 with respect to the root apex (Rt) of the root canal (R) of the tooth (T) is measured based on an electric current value or the like.

The measurement result acquired by the root canal length measurement unit 40 is displayed by the measurement result display unit 27 provided on the hand piece main body 21, and is stored on the root canal length measurement information storage unit (15d) of the storage unit 15.

As shown in FIG. 2, the chair unit 10 includes an operation driving unit 51, a basin unit 52 including a suction device that sucks saliva, cooled water or the like and a device usable to gargle, a medical care chair 53 including a reclining back sheet and an up/down movable seat, a foot controller 54 that is connected to the medical care chair 53, hand piece holders 55 each usable to hold the root canal treating hand piece 20, and a tray table 56. The foot controller 54 includes a pedal (54a) operable by a foot of the operator. It can be detected that the pedal (54a) has been stepped on as well as the amount of stepping.

As shown in FIG. 2, forward to the tray table 56, an operation panel having various types of operation devices 101 located on a top surface thereof, and the hand piece holders 55, are provided. The hand piece holders 55 are each usable to hold the root canal treating hand piece 20.

The operation devices 101 on the operation panel include a touch screen, a pointing stick, a switch and the like. The operation devices 101 may include an appropriate input device such as a mouse or the like.

As shown in FIG. 4, the X-ray CT image capturing device 60 is accommodated in a hollow parallelepiped X-ray-proof chamber (60a) longer in a height direction, and executes CT image capturing to collect projection data. The X-ray CT image capturing device 60 includes a revolving arm 61 which supports an X-ray generation unit (61a) and an X-ray detection unit (61b). The revolving arm 61 is movable up and down along a support pillar and is revolvable. The X-ray generation unit (61a) emits an X-ray cone beam, which is a bundle of X rays, toward a patient (M1), and the X-ray detection unit (61b) detects the X-ray cone beam emitted by the X-ray generation unit (61a).

The X-ray CT image capturing device 60 having such a structure operates as follows. The patient (M1) is located as being held between the X-ray generation unit (61a) and the X-ray detection unit (61b) supported by the revolving arm 61. While the revolving arm 61 revolves around the patient (M1), the X-ray cone beam emitted by the X-ray generation unit (61a) and transmitted through the patient M1 is detected by the X-ray detection unit (61b). Thus, 3D information is acquired.

The X-ray CT image capturing device 60 is connected to the storage unit 15 via the processing device control unit 11, and thus the 3D information acquired by the X-ray CT image capturing device 60 is stored on the three-dimensional information storage unit (15*a*) of the storage unit 15.

In the above description, the 3D information acquired by the X-ray CT image capturing device 60 is stored on the three-dimensional information storage unit (15*a*) of the storage unit 15, and the tooth image (I) or the like is created based on the 3D information and displayed on the monitor 13. Alternatively, the tooth image (I) or the like may be displayed on a collimation screen of a microscope 70 in the microscope-inclusive dental care table 150 shown in FIG. 19.

The microscope-inclusive dental care table 150 includes a medical care chair 53 and a microscope unit 151 located to the side of the medical care chair 53. The microscope unit 151 includes a hanger arm 152 including parts coupled with each other by joints, the microscope 70 attached to a tip of the hanger arm 152, and a light pillar 153 to which a base part of the hanger arm 152 is attached. A microscope main body (70A) is positioned above and in the vicinity of a head rest of the medical care chair 13 by use of the joints of the hanger arm 152, so that the inside of the oral cavity of the patient (M1) (not shown) as the target of surgical operation lying on the medical care chair 13 on his/her back is observed.

This is described in more detail. The microscope 70 is a microscope including the microscope main body (70A), an eyepiece (70Aa), an objective lens (70Ab), a focusing mechanism and the like. The operator directs the objective lens (70Ab) toward the tooth (T) as a target of collimation and peeps through the eyepiece (70Aa) to perform collimation.

Now, with reference to FIG. 5, the tooth image operation screen 100 that is displayed on the monitor 13 and displays the tooth image (I) of the tooth (T) as a target of surgical operation is described. Hereinafter, the tooth (T) as the target of surgical operation may be referred to as the "target tooth (T)".

The tooth image operation screen 100 is divided into a right end part and a main part, which is the rest of the tooth image operation screen 100. Displayed in the main part are the selected tooth image display operation screen 200 (see FIG. 5) that is usable to select the tooth (T) and displays the tooth image (I) of the tooth (T), the root canal extension direction display operation screen 300 (see FIG. 6) that displays the root canal extension direction image (Id) in correspondence with the tooth image (I), and the surgery operation screen 400 (see FIG. 8) that is referred to while a surgical operation is being performed along the root canal extension direction image (Id). The operation screens (200, 300, 400) are switched in accordance with the purpose. By contrast, the right end part displays items common to the operation screens (200, 300, 400), and is described in detail later.

The part that displays the common items is not limited to the right end part, and may be an upper end part, a lower end part, a left end part or the like.

The right end part of the tooth image operation screen 100 displays a file unit 110 in an upper part, a display unit 120 in a middle part, and an information unit 130 in a lower part. As described above, the units (110, 120, 130) are common to the selected tooth image display operation screen 200, the root canal extension direction display operation screen (300, 300) and the surgery operation screen 400.

The file unit 110 includes a file open specification processing unit 111 and a file save specification processing unit 112.

The file open specification processing unit 111 is usable to read information on the patient (M1); more specifically, for example, the name of the patient (M1) or other information that is to be displayed on the information unit 130 (described later), and 3D information on the patient (M1) stored on the three-dimensional information storage unit (15*a*) or information that is acquired by a process performed by use of the selected tooth image display operation screen 200 or the root canal extension direction display operation screen 300 and is to be stored by the file save specification processing unit 112 (described later).

The file save specification processing unit 112 accepts an operation of specifying that information acquired by a process performed by use of the selected tooth image display operation screen 200 or the root canal extension direction display operation screen 300 is to be stored on the storage unit 15. Such information is information on, for example, selection of the tooth (T) as the target of interest performed by use of the selected tooth image display operation screen 200 (described later), or the tooth image (I) of the tooth (T).

The display unit 120 includes a "change display" selection unit 121, a move selection unit 122, a rotation selection unit 123, a scale selection unit 124, a surface selection unit 125, a diagram selection unit 126, an emphasis selection unit 127, and a permeability selection unit 128.

The "change display" selection unit 121 acts as the display change specification operation unit (12*h*), and accepts an operation of selecting the operation screen to be displayed on the tooth image operation screen 100.

In more detail, the "change display" selection unit 121 accepts an operation of displaying, in the main part of the tooth image operation screen 100, an operation screen suitable to each of the steps (s1, s2, s3) in the flowchart shown in FIG. 9.

The move selection unit 122 acts as the display change specification operation unit (12*h*), and accepts an operation of selecting to allow the displayed tooth image (I) or the like to be movable. The rotation selection unit 123 acts as the display change specification operation unit (12*h*), and accepts an operation of selecting to rotate the displayed two-dimensional converted image (It) or the like.

The move selection unit 122 and the rotation selection unit 123 allow the operator to move and rotate the root image (I) displayed on the monitor 13. Therefore, the operator can visually recognize the position or the shape of the root canal (R).

The scale selection unit 124 accepts an operation of selecting to enlarge or contract the displayed tooth image (I) or the like. The surface selection unit 125 acts as the display change specification operation unit (12*h*). In the case where the displayed tooth image (I) is created based on the 3D information, the surface selection unit 125 accepts an operation of selecting to display an image of the surface of the tooth (T). The surface selection unit 125 is also usable to display an image of a surface of the root canal (R) or the root canal orifice (Ro) inside the tooth (T), as well as the image of the surface of the tooth (T).

The diagram selection unit 126 accepts an operation of selecting to display the tooth image (I) of the target tooth (T) with a line drawing.

The emphasis selection unit 127 acts as the display change specification operation unit (12*h*), and accepts an operation of displaying the entirety of, or a part of, the displayed image in an emphasized manner. For example, the root canal (R) or the root canal orifice Ro may be displayed in an emphasized manner, so that the position and the shape of the root canal (R) or the root canal orifice (Ro) are made clear. This allows the operator to visually recognize the root canal (R) or the root canal orifice (Ro) clearly.

The permeability selection unit 128 acts as the permeability specification operation unit (12e), and accepts an operation of selecting to display the entirety of, or a part of, the tooth image (I) displayed on the monitor 13 in a permeable manner. This is described specifically. An image to be displayed in a permeable manner is selected by use a cursor 270, and a desired permeability level is selected by use of the permeability selection unit 128. Thus, the image selected by use of the cursor 270 is displayed at the desired permeability level.

Owing to this, the following is made possible. It is now assumed that two images, for example, the two-dimensional captured image (Ip) captured in the occlusal surface direction, and the two-dimensional converted image (ItP) showing the root canal orifice (Ro) or the like, are displayed in an overlapping manner as in the XY plane root canal extension direction display area 320 (described later) shown in FIG. 6. Even in this case, the permeability level of the two-dimensional captured image (Ip) may be adjusted so that the two images are observed concurrently and thus the position of the root canal orifice (Ro) is displayed (not shown).

The permeability selection unit 128 is not limited to having such a structure, and may be displayed on the tooth image operation screen 100 as a scroll bar.

The information unit 130 displays information on the patient (M1) stored on the storage unit 15, and includes a name unit 131 that displays the name, an M/F unit 132 that displays the gender, an age unit 133 that displays the age, and a record unit 134 that displays the history of treatments.

The information stored on the storage unit 15 is on the name, gender, age, history of treatments or the like, but is not limited to such information. The information stored on the storage unit 15 may be, for example, the name of the operator or the date of the medical care.

Now, with reference to FIG. 5, the selected tooth image display operation screen 200 that is usable to select the target tooth (T) and displays the tooth image (I) of the tooth (T) is described.

As shown in FIG. 5, the selected tooth image display operation screen 200 is divided into an upper display screen and a lower operation screen. The upper display screen includes the dental arch image display area 210 provided in a right part and the target tooth image display area 220 provided in a left part. The lower operation screen includes a target tooth selection unit 230 provided in a right part and a target tooth image display pattern selection unit 240 provided in a left part. In a lower right part of the display screen, namely, between the dental arch image display area 210 and the target tooth selection unit 230, there is provided a jaw specification unit 260 usable to select an upper dental arch or a lower dental arch. In addition, the cursor 270 is provided. The cursor 270 is operable by a pointing device among the operation devices 101, and is movable to both of the display screen and the operation screen (when operated by a mouse, the cursor 270 is occasionally referred to as a "mouse pointer" or simply as a "pointer").

The dental arch image display area 210 displays a dental arch including the target tooth (T). Specifically, in the case where the target tooth (T) is in the upper jaw, the dental arch image display area 210 displays the upper dental arch; whereas in the case where the target tooth (T) is in the lower jaw, the dental arch image display area 210 displays the lower dental arch. Alternatively, the dental arch image display area 210 may display both of the upper dental arch and the lower dental arch.

In this example, a dental arch image (I1) of the lower jaw is displayed (see FIG. 5) with an assumption that the tooth (T) is in the lower jaw. Alternatively, the three-dimensional tooth image (Ic) created based on a range of teeth selected by the target tooth selection unit 230 (described later) or the two-dimensional captured image (Ip) captured by the visible light camera 30 may be displayed (not shown).

The target tooth image display area 220 displays the tooth image I of the target tooth (T) that is selected from the dental arch image displayed in the dental arch image display area 210. The tooth image (I) is created based on the 3D information acquired by the X-ray CT image capturing device 60. The tooth image (I) to be displayed in the target tooth image display area 220 may be the three-dimensional tooth image (Ic) created based on the 3D information acquired by the X-ray CT image capturing device 60 (see FIG. 5) as in this example, the two-dimensional converted image (It) (not shown) created based on the 3D information, or the two-dimensional captured image (Ip).

In the case where being displayed in the target tooth image display area 220, the two-dimensional captured image (Ip), which is an image that is captured in the occlusal surface direction by the visible light camera 30 or the microscope 70, may be displayed as being enlarged. In the case where the two-dimensional captured image (Ip) is captured by the microscope 70, the tectorium may be removed so that the two-dimensional captured image (Ip) shows the root canal orifice (Ro) as being visually recognizable.

The target tooth selection unit 230 acts as the target tooth specification operation unit (12a), and is usable to select the target tooth (T) from the dental arch image displayed in the dental arch image display area 210. The target tooth selection unit 230 includes an "appoint tooth" selection unit 231, an "appoint range" selection unit 232, and an "input tooth No." selection unit 233.

The "appoint tooth" selection unit 231 accepts an operation of selecting the target tooth (T) from the dental arch image displayed in the dental arch image display area 210.

The "appoint range" selection unit 232 accepts an operation of selecting a predetermined range including the target tooth (T) from the dental arch image displayed in the dental arch image display area 210.

The "input tooth No." selection unit 233 accepts an operation of selecting the target tooth (T). Specifically, the "input tooth No." selection unit 233 accepts an operation of specifying the number of the target tooth (T), not an operation of directly selecting the target tooth (T) from the dental arch image displayed in the dental arch image display area 210.

The target tooth image display pattern selection unit 240 acts as the display pattern setting unit (12g), and is usable to select the display pattern of the tooth image (I) in the target tooth image display area 220. The target tooth image display pattern selection unit 240 includes a 2D selection unit 241, a 3D selection unit 242, an oral camera selection unit 243, an XY selection unit 244, an XZ selection unit 245, and a YZ selection unit 246.

The 2D selection unit 241 operates as follows. In the case where, for example, the tooth image (I) to be displayed in the target tooth image display area 220 is the three-dimensional tooth image Ic created based on the 3D information of the target tooth (T) selected by use of the dental arch image display area 210, the 2D selection unit 241 accepts an operation of specifying that the tooth image (I) to be displayed in the target tooth image display area 220 is switched to the two-dimensional converted image (It). The 3D selection unit 242 operates in substantially the same manner. In the case where the tooth image (I) to be displayed in the target tooth image display area 220 is the two-dimensional converted image It, the 3D selection unit 242 accepts an operation of specifying that the tooth image (I) to be displayed in the target tooth image display area 220 is switched to the three-dimensional tooth image (Ic) created based on the 3D information (not shown).

The oral camera selection unit 243 accepts an operation of displaying the two-dimensional captured image (Ip) captured by the visible light camera 30 or the microscope 70 in the target tooth image display area 220 as the tooth image (I) (not shown).

The XY selection unit 244, the XZ selection unit 245, and the YZ selection unit 246 respectively accept an operation of displaying an XY plane, an XZ plane and an YZ plane of the three-dimensional tooth image (Ic) at predetermined positions of the tooth (T) (not shown).

An "XY plane" is a plane parallel to an occlusal surface. Referring to FIG. 4, an "X axis direction" is a left-right direction with respect to the patient (M1), and a leftward direction with respect to the patient (M1) is a "+X axis direction". A "Y axis direction" is a front-rear direction with respect to the patient (M1), and a rearward direction with respect to the patient (M1) is a "+Y axis direction". A "Z axis direction" is an up-down direction, and a vertically upward direction is a "+Z axis direction". The concept represented by the expression "plane parallel to the occlusal surface" is not limited to a plane strictly parallel to the occlusal surface, but encompasses a plane, the line vertical to which crosses the line vertical to the occlusal surface at an angle of ±30 degrees. In other words, the "plane parallel to the occlusal surface" is a plane crossing the occlusal surface at an angle of ±30 degrees.

Now, with reference to FIG. 6, the root canal extension direction display operation screen 300 is described. The root canal extension direction display operation screen 300 is divided into an upper display screen and a lower operation screen. The upper display screen includes a 3D root canal extension direction display area 310 provided in a left part, an XY plane root canal extension direction display area 320 provided in an upper central part, an XZ plane root canal extension direction display area 330 provided in a lower central part, an YZ plane root canal extension direction display area 340 provided in a lower right part, an XY cross-sectional position specification operation unit 331 provided between the XZ plane root canal extension direction display area 330 and the YZ plane root canal extension direction display area 340, and a dental arch display area 350 provided in an upper right part. The lower operation screen includes a root canal extension direction display operation unit 360 provided in a right part, and a simulation operation specification unit 370 provided in a left part. In addition, the cursor 270 is provided. The cursor 270 is operable by the pointing device among the operation devices 101, and is movable to both of the display screen and the operation screen (when operated by a mouse, the cursor 270 is occasionally referred to as a "mouse pointer" or simply as a "pointer").

The 3D root canal extension direction display area 310 displays the three-dimensional tooth image (Ic) of the tooth (T) specified by use of the selected tooth image display operation screen 200. The 3D root canal extension direction display area 310 accepts an operation of specifying the arbitrary point (P), which is performed by an operation made on the root canal extension direction display operation unit 360 (described later) (not shown), and thus displays the root canal extension direction image (Id) and the three-dimensional tooth image (Ic) in an overlapping manner in positional correspondence with each other. The root canal extension direction image (Id) shows the root canal extension direction that passes the arbitrary point (P) and the root canal orifice (Ro) and extends along the root canal (R) toward the outside of the tooth crown.

The XY plane root canal extension direction display area 320 displays the two-dimensional captured image (Ip) captured by the visible light camera 30 included in the root canal treating hand piece 20, and an image of an XY plane of the three-dimensional tooth image (Ic) created on the selected tooth image display operation screen 200, namely, the two-dimensional converted image (ItP), as overlapping, and in correspondence with, each other. The two-dimensional converted image (ItP) is a type of tooth image (I) and shows the three-dimensional tooth image (Ic) of the target tooth (T) as seen in the occlusal surface direction. The XY plane root canal extension direction display area 320 also displays the root canal extension direction image (Id) created based on the 3D information as overlapping, and in positional correspondence with, the two-dimensional captured image (Ip) and the two-dimensional converted image (ItP).

In the XY plane root canal extension direction display area 320, the root canal extension direction is along the root canal (R) and passes the root canal orifice (Ro). Since the root canal extension direction image (Id) is displayed as overlapping, and in correspondence with, the two-dimensional captured image (Ip) and the two-dimensional converted image (ItP), the operator can perform the surgical operation with the curving direction of the root canal (R) in mind. The position in the XY plane root canal extension direction display area 320 at which the two-dimensional converted image (ItP) is displayed can be changed by an operation made on the XY cross-sectional position specification operation unit 331. Therefore, the operator can insert the cutting tool 26 into the root canal (R) as the target of surgical operation to the root canal orifice (Ro) at the shortest possible distance, with the healthy area of the tooth (T) that is unnecessarily cut being minimized.

The XY plane root canal extension direction display area 320 displays the two-dimensional captured image (Ip) and the two-dimensional converted image (ItP) in an overlapping manner. Alternatively, the XY plane root canal extension direction display area 320 may display an image of the XY plane of the three-dimensional tooth image (Ic) created on the selected tooth image display operation screen 200, namely, the two-dimensional converted image (ItP) (see FIG. 7). The two-dimensional converted image (ItP) is a type of tooth image (I) and shows the three-dimensional tooth image (Ic) of the target tooth (T) as seen in the occlusal surface direction. The XY plane root canal extension direction display area 320 may display the two-dimensional captured image (Ip) (not shown).

The XY plane root canal extension direction display area 320 includes a cross-sectional position adjustment scroll bar 321 that accepts an operation of setting the positions of the tooth (T) at which the cross-sectional images are to be displayed in the XZ plane root canal extension direction display area 330 and the YZ plane root canal extension direction display area 340.

This is described in more detail. The cross-sectional position adjustment scroll bar 321 includes bars (321*b*) and arrows (321*a*). The arrows (321*a*) are each moved along the corresponding bar (321*b*) by use of the cursor 270. Thus, the cross-sectional position of a two-dimensional converted cross-sectional image (ItS) to be displayed in each of the XZ plane root canal extension direction display area 330 and the YZ plane root canal extension direction display area 340 is set. The XY plane root canal extension direction display area 320 displays cross-section display lines 322 (more specifically, cross-section display line (322a, 322b)) showing the positions to be set.

Each of the cross-section display lines 322 is held and moved to a desired position by a so-called drag-and-drop operation made on the cursor 270, so that the cross-sectional position is set. The bars (321b) and the arrows (321a) may be omitted, so that the cross-section display lines 322 are directly held and moved.

As described above, the XY plane root canal extension direction display area 320 includes the cross-sectional position adjustment scroll bar 321, and thus displays the desired two-dimensional converted cross-sectional images (ItS) (more specifically, two-dimensional converted cross-sectional images (ItS1, Its2)) of the tooth (T) in the XZ plane root canal extension direction display area 330 and the YZ plane root canal extension direction display area 340 (described later).

The XZ plane root canal extension direction display area 330 displays the two-dimensional converted cross-sectional image (ItS1). The two-dimensional converted cross-sectional image (ItS1) shows a cross-section, of the three-dimensional tooth image (Ic) displayed in the 3D root canal extension direction display area 310, that is taken along the cross-section display line (322y) displayed in the XY plane root canal extension direction display area 320. The two-dimensional converted cross-sectional image (ItS1) is as observed from the side of front teeth. In other words, the two-dimensional converted cross-sectional image (ItS1) shows an XZ cross-section of the tooth (T) as observed in the +Y axis direction. Alternatively, the XZ plane root canal extension direction display area 330 may display the two-dimensional converted cross-sectional image (ItS1) as observed in the −Y axis direction.

The YZ plane root canal extension direction display area 340 displays the two-dimensional converted cross-sectional image (ItS2). The two-dimensional converted cross-sectional image (ItS2) shows a cross-section, of the three-dimensional tooth image (Ic) displayed in the 3D root canal extension direction display area 310, that is taken along the cross-section display line (322x) displayed in the XY plane root canal extension direction display area 320. The two-dimensional converted cross-sectional image (ItS2) is as observed from the right side. In other words, the two-dimensional converted cross-sectional image (ItS2) shows an YZ cross-section of the tooth (T) as observed in the +X axis direction. Alternatively, the YZ plane root canal extension direction display area 340 may display the two-dimensional converted cross-sectional image (ItS2) as observed in the −X axis direction.

Like the 3D root canal extension direction display area 310, the XZ plane root canal extension direction display area 330 and the YZ plane root canal extension direction display area 340 each display the root canal extension direction image (Id) in correspondence with the respective two-dimensional converted cross-sectional image ItS (see FIGS. 14A and 14B). Such display is provided by an operation made on the root canal extension direction display operation unit 360 (described later).

The XY cross-sectional position specification operation unit 331 provided between the XZ plane root canal extension direction display area 330 and the YZ plane root canal extension direction display area 340 is usable to specify the position of the tooth (T) at which the two-dimensional converted cross-sectional image (ItS) of the two-dimensional converted image (ItP) is to be displayed in the XY plane root canal extension direction display area 320.

The dental arch display area 350 displays the dental arch displayed in the dental arch image display area 210 and also explicitly shows the target tooth (T).

The root canal extension direction display operation unit 360 is usable to make specifications in order to set the root canal extension direction. The root canal extension direction display operation unit 360 includes an "appoint any point" specification unit 361, an "appoint direction" specification unit 362, an "auto" specification unit 363, and a set processing unit 364.

The "appoint any point" specification unit 361 acts as the root canal arbitrary point specification unit (12b), and accepts an operation of specifying, for example, the number or the position of the arbitrary point(s) (P) on the two-dimensional converted cross-sectional image (ItS1) displayed in the XZ plane root canal extension direction display area 330. The specification is made by, for example, a click on the cursor 270.

The arbitrary point (P) is not limited to being on the two-dimensional converted cross-sectional image (ItS1) displayed in the XZ plane root canal extension direction display area 330, and may be on the two-dimensional converted cross-sectional image ItS2 displayed in the YZ plane root canal extension direction display area 340 or on the three-dimensional tooth image Ic displayed in the 3D root canal extension direction display area 310.

The "appoint direction" specification unit 362 acts as the root canal extension direction specification unit (12c), and is usable to specify an arbitrary direction along the root canal (R) based on one arbitrary point (P) specified by use of the "appoint any point" specification unit 361.

The root canal extension direction may be determined based on two arbitrary points (P) as described above, or an angle of the root canal extension direction may be determined based on one arbitrary point (P). Alternatively, the root canal extension direction may be determined as follows. The root canal (R) is generally curved. Therefore, multiple points may be set along the curved shape of the root canal (R), so that the curved root canal extension direction is calculated by use of an appropriate interpolation method such as spline interpolation or the like (see FIG. 15).

The "auto" specification unit 363 accepts an operation of automatically calculating the root canal extension direction based on the 3D information. In this case, the operator does not specify the arbitrary point (s) (P). In the case where the "auto" specification unit 363 is used, during the surgical operation, the current position of the cutting tool tip (26a) of the cutting tool 26, or a position that is closer, by several millimeters, to the root apex (Rt), is automatically calculated based on a signal transmitted from the cutting tool position detection unit 16 or the root canal length measurement device 40. Along with the progress of the surgical operation by the cutting tool 26, the root canal extension direction image (Id) connecting these two points is displayed as overlapping, and in correspondence with, the tooth image (I). As can be seen, the root canal extension direction image (Id) may show a straight line or a curved line extending from the position of the cutting tool tip (26a) of the cutting tool 26 to the position several millimeters beyond the position of the cutting tool tip (26a). The root canal extension direction image (Id) may have a width corresponding to the diameter of the root canal (R).

The set processing unit 364 is usable to determine the specification of the arbitrary point (s) (P) performed by use of the "appoint any point" specification unit 361 or the direction specified by use of the "appoint direction" specification unit 362.

Alternatively, the set processing unit 364 may be used as follows. The arbitrary point (s) (P) and the direction are specified by use of the "appoint any point" specification unit 361 and the "appoint direction" specification unit 362. Based on the specified position and direction, the root canal extension direction that is along the root canal (R) and passes the root canal orifice (Ro) to extend toward the outside of the tooth crown is calculated. The set processing unit 364 causes the root canal extension direction image (Id) showing the root canal extension direction to be displayed in the 3D root canal extension direction display area 310, the XY plane root canal extension direction display area 320, the XZ plane root canal extension direction display area 330 and the YZ plane root canal extension direction display area 340 in correspondence with the images displayed therein.

The simulation operation specification unit 370 is usable to determine whether or not the surgical operation can be performed by use of a desired cutting tool 26, and also is usable to display the determination result in the 3D root canal extension direction display area 310 or the like. The simulation operation specification unit 370 includes a "select tool" unit 371, a "run simulation" specification operation unit 372, and a "display result" display processing unit 373.

The "select tool" unit 371 acts as the cutting tool specification unit (12*d*), and is usable to select a desired cutting tool 26.

The "run simulation" specification operation unit 372 acts as the entrance route image processing unit 11*e* together with the "display result" display processing unit 373 (described later). The "run simulation" specification operation unit 372 accepts an operation of executing a simulation in order to check whether or not the root canal treatment can be performed safety and certainly by use of the cutting tool 26 selected by the "select tool" unit 371.

The "display result" display processing unit 373 accepts an operation of specifying that the result of the simulation executed by use of the "run simulation" specification operation unit 372 is to be displayed.

Now, the surgery operation screen 400 usable for the surgical operation is described with reference to FIG. 8.

The display areas common to those of the root canal extension direction display operation screen 300 shown in FIG. 6 and FIG. 7 are described herein.

The surgery operation screen 400 is divided into an upper display screen and a lower operation screen (see FIG. 8), like the selected tooth image display operation screen 200 shown in FIG. 5 and the root canal extension direction display operation screen 300 shown in FIG. 6. The upper display screen has the same arrangement as that of the upper display screen of the root canal extension direction display operation screen 300 shown in FIG. 6. Specifically, the upper display screen of the surgery operation screen 400 includes a 3D root canal extension direction display area 310 provided in a left part, an XY plane root canal extension direction display area 320 provided in an upper central part, an XZ plane root canal extension direction display area 330 provided in a lower central part, an YZ plane root canal extension direction display area 340 provided in a lower right part, an XY cross-sectional position specification operation unit 331 provided between the XZ plane root canal extension direction display area 330 and the YZ plane root canal extension direction display area 340, and a dental arch display area 350 provided in an upper right part. Such an arrangement is the same as that of the upper display screen of the root canal extension direction display operation screen 300.

In the 3D root canal extension direction display area 310 and the like in the surgery operation screen 400, the tooth image (I) and the root canal extension direction image (Id) may be displayed in an overlapping manner. In addition, the cutting tool image (Ih) of the cutting tool 26 selected by use of a "select tool" specification operation unit 471 (described later) may be displayed as overlapping, and in correspondence with, the tooth image (I) or the like.

The operation screen includes a command tool box unit 460 provided in a right part and an operation processing unit 470 in a left part. In addition, the cursor 270 is provided. The cursor 270 is operable by a pointing device among the operation devices 101, and is movable to both of the display screen and the operation screen (when operated by a mouse, the cursor 270 is occasionally referred to as a "mouse pointer" or simply as a "pointer").

The command tool box unit 460 includes an extra screen check box 461, a screen change check box 462, a drive control check box 463, and a warning information check box 464.

The extra screen check box 461 is to be checked to display the 3D root canal extension direction display area 310 in a separate screen on the monitor 13.

The screen change check box 462 is to be checked to switch the 3D root canal extension direction display area 310 to the XY plane root canal extension direction display area 320, the an XZ plane root canal extension direction display area 330 or the YZ plane root canal extension direction display area 340 by a stepping operation on the foot controller 14.

In the state where the extra screen check box 461 is checked, for example, the 3D root canal extension direction display area 310 displayed in the separate screen may be switched to the XY plane root canal extension direction display area 320.

The drive control check box 463 is to be checked to control the drive on the root canal treating hand piece 20 when, for example, an excessive load is applied to the root canal treating hand piece 20, or the cutting tool tip (26*a*) of the cutting tool 26 attached to the root canal treating hand piece 20 is close to the root apex (Rt). Specifically, the cutting tool 26 is stopped to be driven, rotated in a reverse direction, or driven at a lower force.

The warning information check box 464 is to be checked to notify that, for example, the cutting tool tip (26*a*) of the cutting tool 26 attached to the root canal treating hand piece 20 is deviated from the root canal (R) or is close to the root apex (Rt). Such deviation is detected by the cutting tool position detection unit 16 under the control of the processing device control unit 11. Such a notification is not limited to being made when the cutting tool tip (26*a*) of the cutting tool 26 is close to the root apex (Rt), and may be made when, for example, the cutting tool 26 is deviated from an entrance direction or an entrance position calculated by the simulation described above.

The operation processing unit 470 includes the "select tool" specification operation unit 471, a "detect position" specification operation unit 472, a calibration specification operation unit 473, and a "display tool" processing unit 474.

The "select tool" specification operation unit 471 acts as the cutting tool specification unit (12*d*), and accepts an operation of specifying the cutting tool 26 to be used by the operator for the surgical operation.

The "detect position" specification operation unit 472 accepts an instruction to start detecting a three-dimensional position of the root canal treating hand piece 20.

The calibration specification operation unit 473 accepts an instruction to start the calibration on the cutting tool tip (26a) of the cutting tool 26 attached to the root canal treating hand piece 20.

The "display tool" processing unit 474 acts as the surgical operation cutting tool processing unit (11f), and accepts an instruction to start displaying an image of the root canal treating hand piece 20 in, for example, the 3D root canal extension direction display area 310 in an overlapping manner.

The medical care system 1 having the above-described structure is used to perform a medical care on the root canal (R) of the target tooth (T) based on the 3D information acquired by the X-ray CT image capturing device 60. With reference to the flowchart shown in FIG. 9, a process of the medical care including display and surgical operation is briefly described.

First, the target tooth (T) is specified, and the tooth image (I) of the tooth (T) is displayed on the monitor 13 based on the 3D information acquired by the X-ray CT image capturing device 60. Thus, the position of the root canal (R) of the target tooth (T) is clearly shown (step (s1)).

Next, as shown in FIG. 6, the root canal extension direction that is along the root canal (R) of the tooth (T) and passes the root canal orifice Ro to extend toward the outside of the tooth crown is calculated based on the 3D information. It is determined whether or not the cutting tool tip (26a) of the cutting tool 26 will reach the root apex (Rt) when the cutting tool 26 is inserted along the root canal extension direction to cut away the tooth (T). The determination is made based on the information on the root canal extension direction, the information on the cutting tool 26, and the 3D information. When it is determined that the cutting tool tip (26a) of the cutting tool 26 will reach the root apex (Rt), the root canal extension direction image (Id) showing the root canal extension direction is displayed in correspondence with the tooth image (I) (step (s2)).

Next, as shown in FIG. 8, the cutting tool image (Ih) of the selected cutting tool 26 is displayed on the monitor 13 as overlapping, and in correspondence with, the tooth image (I) of the tooth (T) and the root canal extension direction image (Id) also displayed in correspondence with the tooth image (I). The root canal treatment is performed on the tooth (T) while the monitor 13 is observed (step (s3)). When the root canal treatment is finished, the process is finished.

Now, with reference to the flowchart shown in FIG. 10, a method for displaying the tooth image (I) of the target tooth (T) on the selected tooth image display operation screen 200 shown in FIG. 5 is described in detail. This corresponds to step (s1) in the flowchart shown in FIG. 9.

The tooth image (I) displayed in the target tooth image display area 220 may be the two-dimensional converted image (It) or the three-dimensional tooth image (Ic). In this example, it is assumed that the three-dimensional tooth image (Ic) is displayed.

First, in order to perform the medical care on the root canal (R) of the target tooth (T), the operator acquires the 3D information on the tooth (T) and an area in the vicinity thereof including the root canal (R) inside the tooth (T) by use of the X-ray CT image capturing device 60, and stores the 3D information on the three-dimensional information storage unit (15a), beforehand.

Referring to FIG. 5, the tooth image operation screen 100 is displayed on the monitor 13, and the selected tooth image display operation screen 200 is displayed in the main part of the tooth image operation screen 100 by use of the "change display" selection unit 121 of the display unit 120 (step (t1)).

Then, the information on the patient (M1) to be displayed in the information unit 130 is read by use of the file open specification processing unit 111 of the file unit 110 (step (t2)).

Next, the dental arch including the target tooth (T) is selected by use of the jaw specification unit 260 (step (t3)), and the dental arch image showing the target tooth (T) (in FIG. 5, the dental arch image (I1) of the lower jaw) is displayed in the dental arch image display area 210 (step (t4)).

The operator operates the "appoint tooth" selection unit 231 acting as the target tooth specification operation unit (12a) for the dental arch image (I1), displayed in the dental arch image display area 210, to specify the target tooth (T) in the dental arch image (I1) by use of the cursor 270 (step (t5)). When this occurs, the processing device control unit 11 reads the 3D information on the tooth (T) from the 3D information stored on the three-dimensional information storage unit (15a) of the storage unit 15, and di splays a screen (not shown) that accepts an operation of selecting whether or not to display the three-dimensional tooth image (Ic) of the target tooth (T), based on the 3D information (step (t6)).

When it is selected by the operator to display the three-dimensional tooth image (Ic) (step (t6): Yes), the three-dimensional tooth image (Ic) is created and displayed in the target tooth image display area 220 based on the 3D information by use of the three-dimensional tooth image processing unit 11aa of the tooth image processing unit (11a), (steps (t7, t9)). By contrast, although not shown, when it is selected not to display the three-dimensional tooth image (Ic) (step (t6): No), the two-dimensional converted image It of the tooth (T) is created and displayed in the target tooth image display area 220 based on the 3D information stored on the three-dimensional information storage unit (15a), by use of the two-dimensional converted image processing unit (11ac) of the tooth image processing unit (11a) (steps (t8, t9)).

In this example, it is determined whether or not to display the three-dimensional tooth image (Ic) in step (t6). Alternatively, the three-dimensional tooth image (Ic) or the two-dimensional converted image (It) may be automatically displayed by use of the three-dimensional tooth image processing unit (11aa) or the two-dimensional converted image processing unit (11ac) based on the 3D information, and then converted later by use of the 2D selection unit 241 or the 3D selection unit 242 of the target tooth image display pattern selection unit 240 acting as the display pattern setting unit (12g).

As a result of step (t1) through step (t9), the three-dimensional tooth image (Ic) or the like is displayed in the target tooth image display area 220. The three-dimensional tooth image (Ic) is created based on the 3D information acquired by the X-ray CT image capturing device 60 and stored on the three-dimensional information storage unit (15a). Therefore, the root canal (R) or the root canal orifice (Ro) are displayed, and information on the root canal (R) or the like of the target tooth (T) is accurately recognized.

In order to show the root canal (R) clearly, the permeability level may be adjusted by use of the permeability selection unit 128 such that the three-dimensional tooth image (Ic), more specifically, the tooth crown, the enamelum, the dentin or the like is shown as being semi-permeable. In this manner, the root canal (R) or the root canal orifice (Ro) is clearly shown in the target tooth image display area 220. The color image in which the root canal (R) or the like is colored may be displayed in the target tooth image display area 220 in correspondence with the three-dimensional tooth image (Ic) (not shown).

As a result, the operator can grasp the shape of the root canal (R) more accurately.

Now, with reference to the flowchart shown in FIG. 11 and FIG. 12, a method for displaying the root canal extension direction image (Id) in correspondence with the tooth image (I) of the target tooth (T) is described in detail. This corresponds to step 2 in the flowchart shown in FIG. 9.

First, the operator operates the "change display" selection unit 121, acting as the display change specification operation unit (12h), of the display unit 120. Thus, as shown in FIG. 6, the root canal extension direction display operation screen 300 is displayed in the main part of the tooth image operation screen 100 (step (u1)), and the three-dimensional tooth image (Ic) displayed in the target tooth image display area 220 in step (s1) shown in FIG. 9 is displayed in the 3D root canal extension direction display area 310 (step (u2)).

Next, in order to create and display the tooth images (I) of the tooth (T) as being observed in the X, Y and Z directions, the 3D information on tooth (T) is read from the three-dimensional information storage unit (15a). The two-dimensional converted image processing unit (11ac) is operated to create, and display in the XY plane root canal extension direction display area 320, the two-dimensional converted image (ItP) of the tooth (T) as observed in the occlusal surface direction (see FIG. 6). In addition, as shown in FIG. 6, the two-dimensional converted cross-sectional image (ItS1) of the tooth (T) as observed in the Y axis direction, and the two-dimensional converted cross-sectional image (Its2) of the tooth (T) as observed in the X axis direction, are created and displayed respectively in the XZ plane root canal extension direction display area 330 and the YZ plane root canal extension direction display area 340 (step (u3)).

In the case where the display of the tooth image (I) on the selected tooth image display operation screen 200 (step (s1) in FIG. 9) and the display of the root canal extension direction image (Id) (step (s2) in FIG. 9) are to be continuously performed, the "change display" selection unit 121 acting as the display change specification operation unit (12h) is operated to switch the screen in the main part of the tooth image operation screen 100. Thus, the three-dimensional tooth image (Ic) is automatically displayed in the 3D root canal extension direction display area 310. In the case where, for example, the display of the tooth image (I) (step (s1) in FIG. 9) and the display of the root canal extension direction image (Id) (step (s2) in FIG. 9) are to be performed on different dates or with a long interval in time, the following may be performed. The information created in step (s1), for example, the three-dimensional tooth image (Ic), is stored on the storage unit 15 by use of the file save specification processing unit 112. For performing step (s2), the file open specification processing unit 111 is operated to read the information stored on the storage unit 15, for example, the three-dimensional tooth image (Ic). Thus, the three-dimensional tooth image (Ic) or the like is displayed in the 3D root canal extension direction display area 310 or the like.

Next, the two-dimensional captured image (Ip) of the tooth (T) captured beforehand by the visible light camera 30 included in the root canal treating hand piece 20, the microscope 70 or the like is read from the two-dimensional information storage unit (15b). Then, the two-dimensional captured image (Ip) is displayed in the XY plane root canal extension direction display area 320 as overlapping the two-dimensional converted image (ItP) after being adjusted to be in correspondence therewith (step (u4)).

This is described more specifically. In the case where the position of the two-dimensional converted image (ItP) and the position of the two-dimensional captured image (Ip) are different from each other, the move selection unit 122 is operated to allow the images to move. The image(s) is (are) dragged to adjust the positions thereof. In the case where the sizes or the orientations of the images are different from each other, the scale selection unit 124 or the rotation selection unit 123, acting as the display change specification operation unit (12h), of the display unit 120 is used to adjust the size or the orientation of the two-dimensional converted image (ItP) so as to be adapted to that of the two-dimensional captured image (Ip).

It is assumed that, for example, as shown in FIGS. 13A and 13B, the maximum diameter of the tooth (T) in the two-dimensional converted image (ItP) is longer than that of the tooth (T) in the two-dimensional captured image (Ip) and extends in a different direction from that of the tooth (T) in the two-dimensional captured image (Ip). In this case, line (Lp) representing the maximum diameter of the tooth (T) in the two-dimensional captured image (Ip) is specified (see FIG. 13A), and line (Lt) representing the maximum diameter of the tooth (T) in the two-dimensional converted image (ItP) is specified (see FIG. 13B).

Line (Lt) of the tooth (T) in the two-dimensional converted image (ItP) is longer than line (Lp) of the tooth (T) in the two-dimensional captured image (Ip), and line (Lt) extends in a different direction from that of line (Lp) in a counterclockwise direction. Therefore, the two-dimensional converted image (ItP) is rotated clockwise such that the angle of line (Lt) of the tooth (T) in the two-dimensional converted image (ItP) matches the angle of line (Lp) of the tooth (T) in the two-dimensional captured image (Ip). In addition, the two-dimensional converted image (ItP) is contracted such that the length of line (Lt) of the tooth (T) in the two-dimensional converted image (ItP) matches the length of line (Lp) of the tooth (T) in the two-dimensional captured image (Ip). As a result, as shown in FIG. 13C, the tooth (T) in the two-dimensional converted image (ItP) is matched to the tooth (T) in the two-dimensional captured image (Ip) in both of the orientation and the size. Thus, the two-dimensional converted image (ItP) is displayed as overlapping the two-dimensional captured image (Ip) in the XY plane root canal extension direction display area 320.

The size of the two-dimensional converted image (ItP) may be adjusted to the size of the two-dimensional captured image (Ip) by the following method. An area size of the tooth (T) in the two-dimensional captured image (Ip) and an area size of the tooth (T) in the two-dimensional converted image (ItP) are found by image analysis, and the size of the two-dimensional converted image (ItP) is adjusted such that the size of the two-dimensional converted image (ItP) is matched to the size of the two-dimensional captured image (Ip).

The two-dimensional captured image (Ip) may be captured by the visible light camera 30, the microscope 70 or the like immediately before being displayed in the XY plane root canal extension direction display area 320. In this case, the two-dimensional information storage unit (15b) is not necessary.

The two-dimensional captured image (Ip) captured by the visible light camera 30, the microscope 70 or the like may be a moving image, and the two-dimensional converted image (ItP) may be displayed as overlapping, and following, the moving two-dimensional captured image (Ip).

Next, the position of the tooth (T) along which the two-dimensional converted cross-sectional image (ItS1) (XZ plane) is taken to be displayed in the XZ plane root canal extension direction display area 330 is adjusted based on the two-dimensional converted image ItP displayed in the XY plane root canal extension direction display area 320. Similarly, the position of the tooth (T) along which the two-dimensional converted cross-sectional image (Its2) (YZ plane) is taken to be displayed in the YZ plane root canal extension direction display area 340 is adjusted based on the two-dimensional converted image (ItP) displayed in the XY plane root canal extension direction display area 320.

This is described in more detail with reference to FIG. 6. The arrows (321a) are slid by use of the cursor 270 along the bars (321b), in the XY plane displayed in the XY plane root canal extension direction display area 320, to move the cross-section display lines 322 on the plane of the two-dimensional converted image (ItP). Thus, the positions of the tooth (T) along which the two-dimensional converted cross-sectional images (ItS) are to be displayed in the XZ plane root canal extension direction display area 330 and the YZ plane root canal extension direction display area 340 are specified.

As a result, the two-dimensional converted cross-sectional images (ItS1, ItS2) each showing a predetermined position of the tooth (T), for example, the root canal orifice (Ro) as the target of surgical operation, are respectively displayed in the XZ plane root canal extension direction display area 330 and the YZ plane root canal extension direction display area 340.

Next, with reference to the flowchart in FIGS. 11 and 12, and FIG. 14A, a method for calculating the root canal extension direction, which is along the root canal (R) and passes the root canal orifice (Ro) to extend toward the outside of the tooth crown, based on the two-dimensional converted cross-sectional images (ItS) displayed in the XZ plane root canal extension direction display area 330 and the YZ plane root canal extension direction display area 340 is described.

FIG. 14A show enlarged views of the XZ plane root canal extension direction display area 330 and the YZ plane root canal extension direction display area 340 shown on the root canal extension direction display operation screen 300.

First, in order to set the root canal extension direction (step (u5)), the operator determines whether or not to specify the arbitrary point (P), which is the basis for calculating the root canal extension direction (step (u6)).

When it is determined to specify the arbitrary point (P) (step (u6): Yes), the operator operates the "appoint any point" specification unit 361 (FIG. 6) acting as the root canal arbitrary point specification unit (12b), and then operates the set processing unit 364. Thus, the operator moves the cursor 270 to a desired position on, for example, the two-dimensional converted cross-sectional images (ItS1) in the XZ plane root canal extension direction display area 330, and clicks the cursor 270. Thus, the arbitrary point (P) is specified at the desired position (arbitrary point (P1) in FIG. 14A) (step (u7)).

When the arbitrary point (P) is specified, a message (not shown) asking whether or not to specify another arbitrary point (P) is displayed on the monitor 13. It is determined by the operator whether or not to specify another arbitrary point (P) (step (u8)). When it is determined to specify another arbitrary point (P) (step (u8): Yes), the process returns to step (u7). The operator moves the cursor 270 to another desired position on, for example, the two-dimensional converted cross-sectional images (ItS1) in the XZ plane root canal extension direction display area 330, and clicks the cursor 270 as described above. Thus, another arbitrary point (P2) is specified as shown in FIG. 14A (step (u7)). In this manner, the steps (u7, u8) are repeated until it is determined not to specify any more arbitrary point (P). When the specification of the arbitrary point (s) (P) is finished, it is determined by the operator whether or not to perform a surgical operation simulation (step (u9)).

When it is determined not to specify the arbitrary point (P) (step (u6): No), the operator operates the "auto" specification unit 363 to automatically specify an arbitrary point (P) based on the 3D information on the tooth (T) stored on the three-dimensional information storage unit (15a). Thus, the specification of the arbitrary point (P), which is the basis for calculating the root canal extension direction, is finished. Then, it is determined by the operator whether or not to perform a surgical operation simulation (step (u9)).

When it is determined not to perform the surgical operation simulation based on the specified arbitrary point (s) (P) (step (u9): No), the operator operates the "display result" display processing unit 373 to read the 3D information stored on the three-dimensional information storage unit (15a). Thus, based on the 3D information and the arbitrary point (s) (P), the root canal extension direction image (Id) of the root canal extension direction, which is along the root canal (R) and passes the root canal orifice (Ro) to extend toward the outside of the tooth crown, is created and displayed in each of the display areas of the root canal extension direction display operation screen 300 (step (u15)). The root canal extension direction image (Id) is displayed as overlapping, and in correspondence with, the tooth image (I).

The root canal extension direction that passes the root canal orifice (Ro) and is along the root canal (R) is calculated based on the arbitrary point (s) (P). Therefore, at least one of the arbitrary point (s) (P) is preferably on the root canal (R). Alternatively, at least one of the arbitrary point(s) (P) may be outside the root canal (R), for example, on the tooth crown.

In this example, the message asking whether or not to specify another arbitrary point (P) is displayed. Alternatively, the number of arbitrary point(s) (P) to be specified may be determined beforehand. Still alternatively, multiple points may be clicked as the arbitrary points P on the XZ plane root canal extension direction display area 330 or the YZ plane root canal extension direction display area 340 by use of the cursor 270. When the determination of the multiple points is accepted, the points are selected as the arbitrary points (P). In this case, the message is not displayed.

In this example, as shown in FIG. 14A, two arbitrary points (P) on the root canal (R) are specified. Alternatively, as shown in FIG. 14B, one arbitrary point (P) may be specified, so that a direction along the root canal (R) is set based on the one arbitrary point (P).

This is described in more detail. The operator operates the "appoint any point" specification unit 361 acting as the root canal arbitrary point specification unit (12b), and then operates the set processing unit 364. Thus, as shown in FIG. 14B, the operator specifies one arbitrary point (P) on the root canal (R) by use of the cursor 270 in substantially the same manner as described above. Then, the operator operates the "appoint direction" specification unit 362 acting as the root canal extension direction specification unit (12c), and the set processing unit 364. Thus, as shown in FIG. 14B, the straight line image (If) based on the arbitrary point (P) is created by use of the straight line image processing unit (11c). The straight line image (If) is displayed in the XZ plane root canal extension direction display area 330 or the like in correspondence with the two-dimensional converted cross-sectional image (ItS). The straight line image (If) is operated on by use of the cursor 270, so that a desired direction along the root canal (R) is specified.

With the above-described method, the operator can set a direction that is along the root canal (R) based on the arbitrary point (P), for example, the point at the center of the root canal orifice (Ro), as the root canal extension direction. In this manner, the operator can set a desired direction as the root canal extension direction.

The root canal (R) is generally curved. The "appoint any point" specification unit 361 acting as acting as the root canal arbitrary point specification unit (12b) and the set processing unit 364 may be operated to set multiple points (P) along the curved shape of the root canal (R). Therefore, even in the case where the root canal (R) has a complicated shape with bending parts, the root canal extension direction along the root canal (R) is defined by specifying multiple arbitrary points (P) and using an appropriate interpolation method such as spline interpolation or the like (see FIG. 15).

Now, the surgical operation simulation is described (step (u9): Yes).

After the arbitrary point (s) (P) is (are) specified in step (u6) through step (u8), the "select tool" unit 371 acting as the cutting tool specification unit (12d) is operated to display a list of the cutting tools on the monitor 13. The operator selects the cutting tool 26 to be used for the surgical operation from the cutting tools in the list (step (u10)).

When the operation of selecting the cutting tool 26 is accepted (step (u10)), the information on the cutting tool 26 stored on the cutting tool information storage unit (15c) is read (step (u11)).

In this example, it is assumed that the information on the cutting tool stored on the cutting tool information storage unit (15c) is read. Alternatively, information on the cutting tool that is newly downloaded or newly created information on the cutting tool may be used.

Next, the operator operates the "run simulation" specification operation unit 372 to perform the simulation by use of the entrance route image processing unit (11e) to determine whether or not the cutting tool tip (26a) of the cutting tool 26 can reach the root apex (Rt) along the root canal (R). The determination is made based on the 3D information stored on the three-dimensional information storage unit (15a), the information on the diameter or the curving capability of the cutting tool 26 stored on the root canal length measurement information storage unit (15d), and the arbitrary point(s) (P) (step (u12)).

When it is determined, as a result of the surgical operation simulation performed by use of the entrance route image processing unit (11e), that the cutting tool tip (26a) of the cutting tool 26 can reach the root apex (Rt) along the root canal (R) of the target tooth (T) (step (u12): Yes), the root canal extension direction image (Id) is displayed by use of the root canal extension direction processing unit (11b) in the 3D root canal extension direction display area 310 or the like in correspondence with the tooth image (I) (step (u13)).

When it is wished by the operator to display the results of the surgical operation simulation performed by use of the entrance route image processing unit (11e) on the monitor 13 (step (u14): Yes), the operator operates the "display result" display processing unit 373. Thus, the cutting tool image (Is) (FIG. 16) along the root canal extension direction image (Id) is displayed by use of the cutting tool image processing unit (11d) in each of the display areas, for example, the XZ plane root canal extension direction display area 330, as overlapping, and in correspondence with, the tooth image (I). In addition, the entrance route image (Ie) showing the cutting tool 26 reaching the root apex (Rt) along the root canal (R) of the target tooth (T) is displayed by use of the entrance route image processing unit (11e) in each of the display areas, for example, the XZ plane root canal extension direction display area 330 in correspondence with the tooth image (I). Thus, the surgical operation simulation is finished.

When it is wished not to perform the surgical operation simulation (step (u9): No), or when it is wished, by the operator, not to display the results of the surgical operation simulation (step (u14): No), the process shown in FIG. 11 is finished.

By contrast, when it is determined by use of the entrance route image processing unit 11e that the cutting tool tip (26a) of the cutting tool 26 cannot reach the root apex (Rt) along the root canal (R) (step (u12): No), a message asking whether or not to display the simulation results is displayed (step (u16)). When it is wished to display the simulation results (step (u16): Yes), the simulation results are displayed by use of the entrance route image processing unit (11e) (step (u17)).

In this example, the entrance route image (Ie) showing the cutting tool 26 which has cut the tooth (T) up to the farthest possible position is displayed in correspondence with the tooth image (I). Alternatively, a reason why the surgical operation cannot be performed by use of the cutting tool 26, for example, a message that there is a problem in the diameter or the curving capability of the cutting tool 26, may be displayed.

When a reason why the surgical operation cannot be performed by use of the cutting tool 26 is displayed (step (u17)) or when it is wished not to display the simulation results (step (u16): No), it is determined by the operator whether or not the cutting tool 26 is appropriate (step (u18)). When it is determined that the cutting tool 26 is not appropriate (step (u18): No), the process returns to step (u10) to select another cutting tool 26, and the steps (u11) and thereafter are performed again.

When it is determined that the cutting tool 26 is appropriate (step (u18): Yes), the process returns to step (u5), and step (u6) through step (u8) (specification of the arbitrary point(s) (P)) and step (u9) and steps thereafter are performed again.

With the above-described method, the root canal extension direction image (Id) showing the root canal extension direction, which is along the root canal (R) inside the tooth (T) and passes the root canal orifice (Ro) at the end of the root canal (R) to extend toward the outside of the tooth crown, is created based on the 3D information on the tooth (T) acquired by the X-ray CT image capturing device 60. The root canal extension direction image (Id) is displayed on the root canal extension direction display operation screen 300 as overlapping, and in accurate positional correspondence with, the tooth image (I) of the target tooth (T) (see FIG. 6).

As a result, before performing the surgical operation, the operator can allow the root canal extension direction image (Id) showing the root canal extension direction, which extends along the root canal (R) from the outside of the tooth crown of the target tooth (T) through the root canal orifice (Ro), to reach the root apex (Rt), to be clearly shown in positional correspondence with the tooth image (I). Thus, the entrance direction of the cutting tool 26 that passes the root canal orifice (Ro) and is along the root canal (R) is made clear. Therefore, the cutting tool 26 is correctly guided along the root canal (R) of the target tooth (T).

In the case where, for example, it is expected that the cutting tool tip (26a) cannot reach a predetermined position or the root apex (Rt) along the root canal (R) for a reason that the root canal (R) is curved too sharply or is too thin, the reason why the cutting tool (26a) cannot reach the predetermined position or the root apex (Rt) is displayed on the monitor 13. Therefore, the operator can determine, before actually performing the surgical operation, that the root canal (R) cannot be treated by the specified cutting tool 26.

Now, with reference to the flowchart shown in FIG. 17, a method for performing the surgical operation on the root canal (R) of the target tooth (T) is described in detail. The surgical operation is performed while the cutting tool image (Ih) of the root canal treating hand piece 20 is displayed in the XY plane root canal extension direction display area 320 on the surgery operation screen 400 as overlapping, and in correspondence with, the two-dimensional captured image (Ip) and the two-dimensional converted image (ItP).

Only an image (not shown) of the cutting tool 26 may displayed as the cutting tool image (Is) in correspondence with the tooth image (I). Alternatively, the image (not shown) of the cutting tool 26 and the two-dimensional captured image (Ip) captured by the visible light camera 30 built in the root canal treating hand piece 20 may be displayed (see FIG. 8). Still alternatively, an image (not shown) of the entirety of the root canal treating hand piece 20 may be displayed.

First, the "change display" selection unit 121, acting as the display change specification operation unit (12h), of the display unit 120 is operated to display the surgery operation screen 400 in the main part of the tooth image operation screen 100. The root canal extension direction image (Id) and the tooth image (I) displayed in step (s2) are displayed in correspondence with each other in each of the display areas of the surgery operation screen 400 (step (v1) in FIG. 17).

In the case where the display of the root canal extension direction image (Id) (step (s2) in FIG. 9) and the surgical operation (step (s3) in FIG. 9) are to be continuously performed, the screen is switched to automatically display the tooth image (I) and the root canal extension direction image (Id) in each of the display areas of the surgery operation screen 400 in an overlapping manner. In the case where the display of the root canal extension direction image (Id) (step (s2) in FIG. 9) and the surgical operation (step (s3) in FIG. 9) are to be performed on different dates or with a long interval in time, the following may be performed. The file save specification processing unit 112 is operated to store, on the storage unit 15, the information on the tooth image (I), the information on the root canal extension direction, the information on the surgical operation simulation and the like that are displayed on the root canal extension direction display operation screen 300. For performing the surgical operation (step (s3)), the file open specification processing unit (111) is operated to read the information stored on the storage unit 15 to display the tooth image (I).

Next, the "select tool" specification operation unit 471 of the operation processing unit 470 is operated to accept the operation of selecting the cutting tool 26 to be used for the surgical operation (step (v2)). It is determined whether or not the selected cutting tool 26 matches the cutting tool 26 determined in the surgical operation simulation (step (s2) in FIG. 9) as being usable for the surgical operation (step (v3)).

In this example, the operator selects the cutting tool 26. Alternatively, the cutting tool 26 may be provided with an identifier such as an RFID or the like so that the RFID is read by the root canal treating hand piece 20 to select the cutting tool 26.

When it is determined that the selected cutting tool 26 does not match the cutting tool 26 determined as being usable for the surgical operation (step (v3): No), the process returns to step (v2), in which an operation of selecting the cutting tool 26 is accepted again. By contrast, when it is determined that the selected cutting tool 26 matches the cutting tool 26 determined as being usable for the surgical operation (step (v3): Yes), the calibration on the position of the cutting tool 26 is performed (step (v4)). The cutting tool image (Ih) of the cutting tool 26 is displayed in the XY plane root canal extension direction display area 320 or the like as overlapping the tooth image (I) such as the two-dimensional captured image (Ip) or the like (step (v5)). After this, the operator can perform the root canal treatment on the tooth (T) while checking the XY plane root canal extension direction display area 320. During the treatment, the position of the cutting tool 26 is detected in repetition (step (v6) through step (v8)).

This is described in more detail. When it is determined that the selected cutting tool 26 matches the cutting tool 26 determined as being usable for the surgical operation based on the simulation (step (v3): Yes), the operator performs detection of, and calibration on, the cutting tool tip (26a) of the cutting tool 26 respectively by use of the "detect position" specification operation unit 472 and the calibration specification operation unit 473 of the operation processing unit 470 (step (v4)). Based on information on the position of the cutting tool tip (26a) acquired by the calibration, the cutting tool image Ih of the cutting tool 26 to be used for the surgical operation is displayed in the XY plane root canal extension direction display area 320 as overlapping the tooth image (I) such as, for example, the two-dimensional captured image (Ip) and the two-dimensional converted image (ItP) (step (v5)). As a result, the operator can perform the root canal treatment on the tooth (T) while checking, for example, the two-dimensional captured image (Ip) and the cutting tool image (Ih) displayed in the XY plane root canal extension direction display area 320.

This is described more specifically. When it is determined that the cutting tool 26 selected by the operator matches the cutting tool 26 determined as being usable for the surgical operation based on the simulation, the operator operates the "detect position" specification operation unit 472 to detect the three-dimensional position of the root canal treating hand piece 20 by use of the cutting tool position detection unit 16. Next, the operator operates the calibration specification operation unit 473 to detect the relative positions of the cutting tool tip (26a) of the cutting tool 26 and the tooth (T) by use of an output from the cutting tool position detection unit 16 or an output from the root canal length measurement device 40 (step (v4)). The cutting tool image (Ih) is displayed by use of the surgical operation cutting tool processing unit (11f) in the XY plane root canal extension direction display area 320 or the like as overlapping the tooth image (I) displayed as overlapping the root canal extension direction image (Id) (step (v5)).

The position of the root canal treating hand piece 20 may be detected as follows. An absolute position of the root canal treating hand piece 20 may be detected by use of a GPS device acting as the cutting tool position detection unit 16. Other methods usable for detecting the root canal treating hand piece 20 include a method of detecting a three-dimensional position measurement marker, attached to the root canal treating hand piece 20, by use of an infrared detector; a method of detecting a magnetic sensor, attached to the root canal treating hand piece 20, by use of a three-dimensional magnetic detector; and a method of measuring a three-dimensional position by use of infrared rays. The relative positions of the root canal treating hand piece 20 and the tooth (T) that is being treated can be detected optically or magnetically by such a non-contact three-dimensional position measurement method. Therefore, the tooth image (Ip, Ic or It), the root canal extension direction image (Id), and the cutting tool image (Is) are displayed on the monitor 13 in an overlapping manner as described above.

An example of calibration performed on the root canal treating hand piece 20 is described. In the case where, for example, the root canal treating hand piece 20 is provided with a position detection unit that detects the position of the cutting tool tip (26a) of the cutting tool 26, which is attached to the tip of the root canal treating hand piece 20, and a gyrosensor that detects the inclination of the root canal treating hand piece 20, the following is performed. The cutting tool tip (26a) of the cutting tool 26 detected by the cutting tool position detection unit 16 is put into contact with two points on the tooth (T) corresponding to two arbitrary points on the XY plane root canal extension direction display area 320. Thus, the relative positions of the cutting tool tip (26a) of the cutting tool 26 attached to the root canal treating hand piece 20 and the tooth (T) are detected. The inclination of the root canal treating hand piece 20 is detected by use of the gyrosensor.

In this manner, the position of the cutting tool tip (26a) of the cutting tool 26 with respect to the tooth (T) is calibrated, and the positional relationship between the tooth image (I) and the cutting tool image (Ih) displayed on the monitor 13 is matched to the positional relationship between the tooth (T) and the cutting tool tip (26a) of the cutting tool 26 in the actual treatment. Thus, the cutting tool image (Ih) is displayed on the monitor 13 as overlapping, and in correspondence with, the tooth image (I).

The above-described relative positions may be detected by a three-dimensional positional position measurement on two or more arbitrary points, a combination of measurement by a gyrosensor and the three-dimensional positional position measurement, or a combination of a two-dimensional position measurement on two or more arbitrary points and measurement by a gyrosensor. The position detection is not limited to such direct detection, and may be performed by calculation based on the detection results acquired by the detection unit.

The calibration on the position of the cutting tool tip (26a) of the cutting tool 26 is not limited to being based on the output from the cutting tool position detection unit 16, and may be based on an output from the root canal length measurement device 40. Alternatively, these outputs may be used in a switching manner, or may be combined.

The output from the cutting tool position detection unit 16 may be used for the surgical operation on an area up to the root canal orifice (Ro), whereas the output from the root canal length measurement device 40 may be used for an area from the root canal orifice Ro to the root apex (Rt). In general, the root canal (R) of a molar tooth or the like is curved. Therefore, in the case where the calibration is merely performed on the cutting tool 26 at a position where the cutting tool 26 is straight, the position of the cutting tool tip (26a) of the cutting tool 26 is not necessarily detected. Therefore, when the cutting tool tip (26a) is close to the root apex (Rt), the calibration is performed on the position of the cutting tool tip (26a) based on the measurement signal from the root canal length measurement device 40. Thus, the position of the cutting tool tip (26a) is detected more accurately. By contrast, in the state where the cutting tooth tip (26a) is in the area up to the root canal orifice (Ro), the tooth image (Ip, Ic or It), the root canal extension direction image (Id), and the cutting tool image (Is) may be displayed, as changing in accordance with the output from the cutting tool position detection unit 16, as overlapping the image of the root canal orifice (Ro) as seen in the occlusal surface direction.

With the above-described method, the calibrated cutting tool image (Ih) of the calibrated cutting tool 26 is displayed in the XY plane root canal extension direction display area 320 as overlapping, and in correspondence with, the two-dimensional captured image (Ip) and the two-dimensional converted image (ItP). Therefore, the operator can perform the surgical operation on the tooth (T) while checking the XY plane root canal extension direction display area 320. When the surgical operation has not been finished (step (v7): No), it is determined whether or not to change the cutting tool 26 (step (v8)). When it is determined to change the cutting tool 26 (step (v8): Yes), a simulation is performed to determine whether or not the cutting tool 26 to be used by the operator is usable for the surgical operation (step (u12)). When the cutting tool 26 is usable for the surgical operation, the root canal extension direction image (Id) is displayed in the 3D root canal extension direction display area 310, and the surgical operation is resumed by use of the cutting tool 26 (step (v1) through step (v7)).

When it is determined not to change the cutting tool 26 (step (v8): No), the detection of the position of the root canal treating hand piece 20 and the surgical operation are repeated until the finish of the surgical operation (step (v6)). When it is determined to finish the surgical operation (step (v7): Yes), the process shown in FIG. 17 is finished.

With the above-described method, the cutting tool image (Ih) of the root canal treating hand piece 20 is displayed as overlapping, and in correspondence with, the two-dimensional captured image (Ip) and the two-dimensional converted image (ItP) displayed in correspondence with the root canal extension direction image (Id). Thus, for example, the operator can perform the treatment on the root canal (R) while checking the XY plane root canal extension direction display area 320 showing the cutting tool image (Ih), the two-dimensional captured image (Ip) and the like in an overlapping manner.

The root canal extension direction shown by the root canal extension direction image (Id) is along the root canal (R) and passes the root canal orifice (Ro) at the end of the root canal (R) to extend toward the outside of the tooth crown. Therefore, for the surgical operation on an area from the tooth crown to the root canal orifice (Ro), the root canal extension direction image (Id) is straight toward the outside of the tooth crown as shown in FIG. 6 and FIG. 7. Thus, the root canal extension direction image (Id) acts as a guide to introduce the cutting tool 26. Therefore, the operator can operate the root canal treating hand piece 20 such that the cutting tool image (Ih) is along the root canal extension direction image (Id) while checking, for example, the XY plane root canal extension direction display area 320. In this manner, the cutting tool tip (26a) of the cutting tool 26 reaches the root canal orifice (Ro). The part of the tectorium that is cut away during the treatment on the root canal (R) is minimized.

The root canal extension direction image (Id) and the cutting tool image (Ih) are displayed in an overlapping manner in the XZ plane root canal extension direction display area 330 or the like. Therefore, the root canal extension direction and the direction of the root canal (R) can be checked in an image other than the image of the tooth (T) as seen in the occlusal surface direction, for example, in the image of the XZ cross-section of the tooth (T) shown in the XZ plane root canal extension direction display area 330. Thus, the part of the tectorium that is cut away is minimized, and the surgical operation can be performed safely and cautiously.

When the cutting tool tip (26*a*) of the cutting tool 26 becomes close to the root apex (Rt), the cutting tool image (Ih) displayed based on the position information of the root canal treating hand piece 20 detected by the cutting tool position detection unit 16 may be switched to the cutting tool image (Ih) showing the position of the cutting tool tip (26*a*) based on the measurement result of the root canal length measurement device 40, and the latter cutting tool image (Ih) may be displayed as overlapping the tooth image (I) in each of the display areas shown in FIG. 8. Alternatively, the position information on the root canal treating hand piece 20 detected by the cutting tool position detection unit 16 and the position information on the cutting tool tip (26*a*) detected by the root canal length measurement device 40 may be combined to define the position of the cutting tool tip (26*a*), and the resultant cutting tool image (Ih) may be displayed as overlapping, and in correspondence with, the tooth image (I). The cutting tool position detection unit 16 may perform the detection by the non-contact three-dimensional position measurement method described above. Instead of the cutting tool position detection unit using the non-contact three-dimensional position measurement method, the root canal length measurement device 40 may be used. The cutting tool position detection unit 16 using the non-contact three-dimensional position measurement method may be switched to the root canal length measurement device 40 at the time when the cutting tool tip (26*a*) becomes close to the root apex (Rt). In the case where the root canal (R) has a certain shape, the cutting tool position detection unit 16 and the root canal length measurement device 40 may be used in combination. For switching the devices, a switching unit (not shown) may be provided such that the devices can be switched at a position optimal to the degree of curving of the root canal (R). For acquiring the position information, only the cutting tool position detection unit 16 using the non-contact three-dimensional position measurement method or only the root canal length measurement device 40 may be used in accordance with the shape of the site to be cut away or the shape of the root canal (R).

During the surgical operation, the current position of the cutting tool tip (26*a*) of the cutting tool 26, or a position that is closer, by several millimeters, to the root apex (Rt), may be automatically calculated based on a signal transmitted from the cutting tool position detection unit 16 or the root canal length measurement device 40. Along with the progress of the surgical operation by the cutting tool 26, the root canal extension direction image (Id) connecting these two points may be displayed as overlapping, and in correspondence with, the tooth image (I). Thus, the shape of the curved root canal (R) at the position beyond the cutting tool tip (26*a*) of the cutting tool 26 by several millimeters is displayed in real time. Alternatively, the past trace of the positions of the cutting tool tip (26*a*) and the simulation results may be displayed.

The drive control check box 463 or the warning information check box 464 may be checked so that the surgical operation is performed safely and cautiously.

This is described more specifically. The position of the cutting tool tip (26*a*) of the cutting tool 26 is detected by the cutting tool position detection unit 16 or the root canal length measurement device 40. When the cutting tool tip (26*a*) is deviated from a certain range that is set based on the root canal extension direction or reaches a position close to the root apex (Rt) by a predetermined distance, the drive on the root canal treating hand piece 20 is restricted by the surgical operation cutting tool control unit (11*g*), or a notification is made by the position detection notification unit 251 of the notification unit 25 in the form of, for example, a sound such as a buzzer or illumination. Thus, the operator can perform the surgical operation safely and cautiously.

Similarly, when the cutting tool tip (26*a*) of the cutting tool 26 is detected by the cutting tool position detection unit 16 to have deviated from a certain angle range around the root canal extension direction, the drive on the root canal treating hand piece 20 is restricted by the surgical operation cutting tool control unit (11*g*), or a notification is made by the direction detection notification unit 252 of the notification unit 25 in the form of, for example, a sound such as a buzzer or illumination. Thus, the operator can perform the surgical operation safely and carefully.

In the case where the root canal treating hand piece 20 including the root canal length measurement device 40 is used, the position of the cutting tool tip (26*a*) of the cutting tool 26 with respect to the root apex (Rt) is measured. Therefore, the operator can perform the surgical operation cautiously and carefully while being aware that the cutting tool tip (26*a*) of the cutting tool 26 is becoming close to the root apex (Rt).

In this case, the root canal length measurement information storage unit (15*d*) is not necessary.

In the case where the visible light camera 30 is included in the root canal treating hand piece 20 as in this example, the operator does not need to hold the visible light camera 30 and the root canal treating hand piece 20 in a switching manner and thus can perform the treatment smoothly. Alternatively, the visible light camera 30 that captures the two-dimensional captured image (Ip) may be provided as an independent instrument in the medical care system 1. As shown in FIG. 19, the microscope 70 included in the dental care table 150 may be used instead of the visible light camera 30. In this case, neither the visible light image processing unit (11*ab*) of the tooth processing device control unit 11 nor the two-dimensional information storage unit (15*b*) of the storage unit 15 is necessary.

In the case where the microscope 70 is used, the two-dimensional converted image (ItP) created based on the 3D information is displayed on a screen viewable through the eyepiece (70Aa), as overlapping, and in correspondence with, the two-dimensional captured image (Ip) of the tooth (T) collimated by the microscope main body (70A) as described above. In addition, the root canal extension direction image (Id) and the cutting tool image (Ih) are displayed in correspondence with the two-dimensional captured image (Ip).

Thus, the operator can perform the surgical operation while viewing the root canal extension direction image (Id) or the like viewable through the eyepiece (70Aa). Therefore, the operator does not need to view the tooth image (I) showing the position of the root canal orifice (Ro) or the like and the oral cavity of the patient (M1) in a switching manner, and can perform the surgical operation safely and accurately.

Now, with reference to FIGS. 18A, 18B and 18C, a method for showing the shape of the root canal (R), by use of a plane including the root canal extension direction, during the surgical operation performed on the root canal (R) of the target tooth (T) is described.

First, the root canal cross-sectional image (ItC) that shows the plane that including the straight root canal extension direction and is rotatable about the root canal extension direction image (Id) as a rotation axis (Xr) is created by the cross-sectional image processing unit (11*ag*). The root canal cross-sectional image (ItC) is displayed in, for example, the 3D root canal extension direction display area 310. The straight root canal extension direction image (Id) is displayed in step (s2) (see FIG. 5).

Since the straight root canal extension direction image (Id) is along the root canal (R) and passes the root canal orifice (Ro), the root canal cross-sectional image (ItC) shows a cross-section of the root canal (R) (see FIGS. 18A, 18B and 18C).

As shown in FIG. 18A, the root canal (R) is curved in general. Therefore, as shown in FIG. 18B, a root canal cross-sectional image (ItC1) including the root canal extension direction image (Id) may not show the root apex (Rt) and the vicinity thereof in the case where the root canal cross-sectional image (ItC1) shows a certain cross-section of the root canal (R). Therefore, the shape of the root canal (R), especially, the shape of the root apex (Rt) and the vicinity thereof, cannot be accurately grasped. However, the root canal cross-sectional image (ItC) is rotatable about the straight root canal extension direction image (Id) as the rotation axis (Xr) (see FIG. 18(*a*)). The root canal cross-sectional image (ItC) showing a plane, with which the curved shape of the root canal (R) is observed, is rotated to display a root canal cross-sectional image (ItC2), which shows the shape of the root apex (Rt) and the vicinity thereof (see FIG. 18(*c*)).

Thus, even in the case where the root canal (R) is bent or even branched, the root canal cross-sectional image (ItC) including the root canal extension direction image (Id) may be rotated about the root canal extension direction image (Id) as the rotation axis (Xr), so that the shape of the root canal (R) can be accurately grasped.

The root canal extension direction calculated in step (s2) in the flowchart shown in FIG. 9 is not necessarily straight, and may be curved. In the case where the root canal extension direction is curved, the root canal cross-sectional image (ItC) may be displayed as follows. The root canal extension direction that passes the root canal orifice (Ro) to expand toward the outside of the tooth crown in a straight manner is calculated based on the curved root canal extension direction, and a plane including a root canal extension direction image (Ids) showing the calculated root canal extension direction is displayed as the root canal cross-sectional image (ItC) (not shown).

As described above, the medical care system 1 acting as a display device includes the three-dimensional information storage unit (15*a*) that stores the 3D information, including the information on the root canal (R) of the tooth (T), acquired by the X-ray CT image capturing device 60, the target tooth specification operation unit (12*a*) usable to specify the target tooth (T), the tooth image processing unit (11*a*) that creates the tooth image (I) of the tooth (T), the monitor 13 that displays the tooth image (I), and the root canal extension direction processing unit (11*b*) that creates the root canal extension direction image (Id) showing the root canal extension direction along the root canal (R) of the tooth (T) and displays the root canal extension direction image (Id) on the tooth image operation screen 100 on the monitor 13 as overlapping, and in correspondence with, the tooth image (I), based on the 3D information. The root canal extension direction image (Id) is displayed on the tooth image operation screen 100 on the monitor 13 in correspondence with the tooth image (I). Therefore, during the root canal treatment, the root canal extension direction is shown, and the cutting tool 26 is guided to the desired root canal (R). Thus, the healthy area of the tooth (T) that is cut away is minimized.

This is described in more detail. The root canal extension direction image (Id), showing the direction that is along the root canal (R) inside the tooth (T) and passes the root canal orifice (Ro) to extend toward the outside of the tooth crown or the direction in which the cutting tool 26 is to be advanced toward the root apex (Rt), is created based on the 3D information on the tooth (T) acquired by the X-ray CT image capturing device 60. The root canal extension direction image (Id) is displayed on the monitor 13 as overlapping, and in accurate correspondence with, the tooth image (I) of the target tooth (T). Thus, the direction extending from the outside of the tooth crown toward the root canal orifice Ro of the tooth (T) and further toward the root apex (Rx) along the root canal (R) is clearly displayed. Therefore, the entrance direction of the cutting tool 26 that passes the root canal orifice (Ro) to extend toward the root apex (Rt) along the root canal (R) is made clear. As can be seen, the root canal extension direction image (Id) showing the direction extending from the outside of the tooth crown toward the root canal orifice (Ro) acts as a guide to introduce the cutting tool 26 toward the root canal orifice (Ro). The root canal extension direction image (Id) showing the direction in which the root canal (R) extends from the cutting tool tip (26*a*) of the cutting tool 26 in use toward the root apex (Rt) acts as a guide to introduce the cutting tool 26 toward the root apex (Rt). As a result, the entrance direction of the cutting tool 26 into the root canal (R) is made clear, and the cutting tool 26 is accurately guided so as to be along the root canal (R) of the target tooth (T).

The tooth image processing unit (11*a*) creates the tooth image (I) of the tooth (T) specified by use of the target tooth specification operation unit (12*a*) based on the 3D information stored on the three-dimensional information storage unit (15*a*). Owing to this, the tooth image (I) showing the root canal orifice (Ro) and the root canal (R), and the root canal extension direction image (Id), are displayed on the monitor 13 as overlapping, and in correspondence with, each other based on the 3D information on the tooth (T) acquired by the X-ray CT image capturing device 60. Therefore, the cutting tool 26 is accurately guided to the root canal (R) of the tooth (T). During the treatment on the root canal (R), the healthy area of the dentin that is cut away is minimized, and the cutting tool 26 is accurately guided to the desired root canal (R).

The medical care system 1 includes the root canal arbitrary point specification unit (12*b*) that accepts an operation of specifying an arbitrary point (P) on the root canal (R), and the root canal extension direction processing unit (11*b*) creates the root canal extension direction image (Id) based on the arbitrary point (P) specified by use of the root canal arbitrary point specification unit (12*b*). Owing to this, even in the case where the root canal (R) has a complicated shape of, for example, being bent or branched, the arbitrary point (P) may be specified along the shape of the root canal (R), so that the root canal extension direction along the root canal (R) is appropriately set and displayed.

The root canal arbitrary point specification unit (12b) accepts an operation of specifying multiple arbitrary points (P) at a predetermined interval. Owing to this, the root canal extension direction is defined so as to pass the arbitrary points (P). Therefore, the degree of freedom of the root canal extension direction is raised.

A part of the arbitrary points (P) specified by use of the root canal arbitrary point specification unit (12b) is at a position on the tooth crown where the cutting tool 26 enters the root canal (R) or at a position on the root canal orifice (Ro) of the tooth (T). Owing to this, even in the case where, for example, there are multiple root canal orifices (Ro) of the root canal (R), the root canal orifice (Ro) as the target of interest is accurately specified.

The tooth image processing unit (11a) creates, as the tooth image (I), the root canal cross-sectional image (ItC) that shows a cross-section of the tooth (T) passing the rotation axis (Xr) and is rotatable about the rotation axis (Xr). The rotation axis (Xr) is the straight root canal extension direction. The tooth image processing unit (11a) displays the root canal cross-sectional image (ItC) on the monitor 13. Owing to this, the root canal (R) of the target tooth (T) is displayed with a cross-section taken along a plane of any angle. Therefore, even in the case where the root canal (R) has a complicated shape, the shape of the root canal (R) can be easily recognized visually.

This is described in more detail. The root canal extension direction extends along the root canal (R) from the outside of the tooth crown through the root canal orifice (Ro). Therefore, the plane including the root canal extension direction includes a cross-section of the root canal (R) from the root canal orifice (Ro). Thus, the shape of the root canal (R) is displayed accurately.

The root canal cross-sectional image (ItC) is rotatable about the rotation axis (Xr), namely, the root canal extension direction. Owing to this, even in the case where the root canal (R) has a complicated shape of, for example, being bent or branched three-dimensionally, a cross-section including, for example, the bending direction of the root canal (R) is displayed and thus the shape of the root canal (R) can be accurately grasped because the root canal cross-sectional image (ItC) is rotated about the rotation axis (Xr), namely, the root canal extension direction. The root canal extension direction image (Id) is not limited to being straight or curved, and may have a width corresponding to the thickness of the root canal (R).

The medical care system 1 includes the visible light camera 30 that captures the visible light two-dimensional captured image (Ip) of the target tooth (T) in the occlusal surface direction. The tooth image processing unit (11a) creates, as the tooth image (I), the two-dimensional converted image (It) showing a predetermined plane based on the 3D information. The tooth image processing unit (11a) displays the two-dimensional converted image (It) on the monitor 13 in correspondence with the two-dimensional captured image (Ip). Owing to this, the shape of the root canal (R) inside the tooth (T), and the direction that is along the root canal (R) and passes the root canal orifice (Ro), are clearly shown against the visible light two-dimensional captured image (Ip).

This is described in more detail. The visible light two-dimensional captured image (Ip) of the target tooth (T) captured in the occlusal surface direction, and the two-dimensional converted image (ItP) created based on the 3D information on the tooth (T) and showing a predetermined plane, are displayed on the monitor 13 in correspondence with each other. The 3D information includes information on the root canal (R) inside the tooth (T). The root canal extension direction image (Id) created based on the 3D information is also displayed on the monitor 13 as overlapping, and in accurate correspondence with, the two-dimensional captured image (Ip) and the two-dimensional converted image (ItP).

Owing to this, the two-dimensional converted image (ItP) shows the position, the size or the like of the root canal orifice (Ro) inside the tooth (T) against the visible light two-dimensional captured image (Ip) of the surface of the target tooth (T). Therefore, while checking the two-dimensional captured image (Ip) of the surface of the target tooth (T), the operator can grasp the position or the size of the root canal orifice Ro inside the tooth (T) and also the direction that is along the root canal (R) and passes the root canal orifice (Ro), namely, the direction in which the cutting tool 26 is to be introduced.

The root canal extension direction processing unit (11b) creates, as the root canal extension direction image (Id), a root canal extension direction converted image. The root canal extension direction converted image is a two-dimensional image of the root canal extension direction image (Id) and shows a predetermined plane. The root canal extension direction processing unit (11b) displays the root canal extension direction converted image on the monitor 13 as overlapping, and in correspondence with, the tooth image (I). Owing to this, the position or the size of the root canal (R), and also the root canal extension direction along the root canal (R) inside the tooth (T), are clearly shown against the visible light two-dimensional captured image (Ip) of the surface of the tooth (T). Thus, the operator can perform the surgical operation accurately.

The medical care system 1 includes the visible light camera 30 that captures an image of the target tooth (T) in the occlusal surface direction. The tooth image processing unit (11a) creates, as the tooth image (I), the two-dimensional captured image (Ip) as seen in the occlusal surface direction based on the information captured by the visible light camera 30. Owing to this, the root canal extension direction image (Id) showing the direction toward the root canal orifice (Ro) and the two-dimensional captured image (Ip) are displayed in an overlapping manner. The two-dimensional captured image (Ip) is created based on the information captured by a visible light camera such as, for example, the visible light camera 30 built in the root canal treating hand piece 20 or a visible light camera attached to the root canal treating hand piece 20, or the microscope 70. Since the root canal extension direction image (Id) and the two-dimensional captured image (Ip) are displayed in an overlapping manner, the operator can visually recognize the direction toward the root canal orifice (Ro) inside the target tooth (T) based on the two-dimensional captured image (Ip), and can perform the surgical operation safely and accurately.

The medical care system 1 includes the cutting tool information storage unit (15c) that stores the cutting tool information on the cutting tool 26 to be used for the surgical operation on the tooth (T), the cutting tool specification unit (12d) that accepts an operation of specifying the cutting tool 26 to be displayed on the monitor 13, and the cutting tool image processing unit (11d) that creates the cutting tool image (Is) based on the cutting tool information on the cutting tool 26 specified by use of the cutting tool specification unit (12d) and displays the cutting tool image (Is) on the monitor 13 as overlapping, and in correspondence with, the tooth image (I). Owing to this, an image of the cutting tool 26 is displayed on the monitor 13. For example, the image of the cutting tool 26 may be displayed along the root canal extension direction. In this case, the operator can easily grasp the entrance direction of the cutting tool 26 visually.

The medical care system 1 includes the entrance route image processing unit (11*e*) that creates the entrance route image (Ie) showing the entrance route of the cutting tool 26 along the root canal (R) based on the cutting tool information and the root canal extension direction. The entrance route image processing unit (11*e*) displays the entrance route image (Ie) on the monitor 13 in correspondence with the tooth image (I). Owing to this, the entrance direction of the cutting tool 26 is clearly shown so as to be visually recognizable. Therefore, the operator can perform the surgical operation accurately and safely.

This is described in more detail. Before performing the surgical operation, the operator can display the entrance route of the cutting tool 26 along the root canal (R) on the monitor 13 based on the 3D information on the tooth (T) acquired by the X-ray CT image capturing device 60, the information on the cutting tool 26 to be used for the surgical operation, and the root canal extension direction.

Therefore, before performing the surgical operation, the operator can visually recognize the state of the cutting tool 26 entering the root canal (R) along the root canal extension direction. The operator can determine whether or not to perform the surgical operation based on the displayed entrance route image (Ie). Thus, the healthy area of the tooth (T) that is cut away is minimized, and the cutting tool 26 is guided to the desired root canal (R).

The medical care system 1 includes the permeability specification operation unit (12*e*) that accepts an operation of specifying the permeability level of at least a part of the images displayed on the monitor 13 in an overlapping manner. The tooth image processing unit (11*a*) creates an image having the permeability level specified by use of the permeability specification operation unit (12*e*). Owing to this, for example, the root canal extension direction image (Id) may be made semi-permeable so that the position of the root canal orifice (Ro) of the root canal (R) is clearly shown against the tooth image (I) while the root canal extension direction along the root canal (R) is clearly shown. The visible light image may be made semi-permeable so that the root canal (R) is clearly shown against the tooth image (I) created based on the 3D information. Alternatively, the tooth image (I) may be made semi-permeable so that the visible light image is clearly shown. In this manner, one of the tooth image (I) and the visible light image displayed in an overlapping manner is clearly shown against the other. Therefore, the operator can perform the treatment on the root canal (R) more precisely and accurately. In addition, while one of the images is clearly shown, the other image may be made permeable or non-permeable. In this manner, the operator can perform the treatment while mainly checking the image clearly shown.

The medical care system 1 includes the color specification operation unit (12*f*) that accepts an operation of specifying the color of at least a part of the images displayed on the monitor 13 in an overlapping manner. The tooth image processing unit (11*a*) creates a color image having the color specified by use of the color specification operation unit (12*f*). Owing to this, for example, the root canal (R) shown in the tooth image (I) created based on the 3D information is colored. In this manner, one of the tooth image (I) and the visible light image displayed in an overlapping manner is clearly shown against the other. Therefore, the operator can perform the treatment on the root canal (R) more precisely and accurately. The root canal (R) may be shown with a color, and the cutting tool tip (26*a*) of the cutting tool 26 may be displayed as overlapping the tooth image (I) based on an output from the cutting tool position detection unit 16 or an output from the root canal length measurement device 40. In this case, the operator can perform the surgical operation while grasping, in real time, that the cutting tool 26 is becoming close to the root apex (Rt). The area from the cutting tool tip (26*a*) of the cutting tool 26 to the root apex (Rt)) may be displayed with a color. In this case, the color of this area indicates the entrance direction of the cutting tool 26.

With the medical care system 1 including the tooth image operation screen 100 and the root canal treating hand piece 20 usable to perform the surgical operation on the tooth (T), the operator can perform the surgical operation on the target tooth (T) in the oral cavity while checking the direction toward the root canal orifice Ro of the target tooth (T) with the tooth image (I) and/or the two-dimensional captured image (Ip) displayed on the monitor 13.

The medical care system 1 includes the driving unit 22 that drives the cutting tool 26 attached to the root canal treating hand piece 20 and also the hand piece control unit 23 that controls the driving unit 22. The hand piece control unit 23 controls the cutting tool 26 in accordance with the type of the cutting tool 26. Owing to this, the operator can perform the surgical operation safely and accurately.

This is described in more detail. Cutting tools are available in various types that are different in the length, the diameter or the shape. One type of cutting tool moves up and down to cut, and another type of cutting tool rotates to cut. Still another type of cutting tool rotates in a cutting direction and a non-cutting direction alternately. The drive control on the cutting tool 26 is changed in accordance with the type thereof. Multiple types of cutting tools 26 different in the diameter or the length are often used for the root canal treatment. The degree of curving of the cutting tool 26 is different in accordance with the type. Therefore, the hand piece control unit 23 controls the cutting tool 26 in accordance with the type thereof. Thus, the cutting tool 26 is controlled appropriately.

The medical care system 1 includes the cutting tool position detection unit 16 that detects at least one of a surgical operation direction, in which the cutting tool 26 attached to the root canal treating hand piece 20 advances into the target tooth (T), and the position of the root canal treating hand piece 20. Owing to this, the image of the root canal treating hand piece 20 is displayed on the monitor 13 in correspondence with the tooth image (I).

This is described in more detail. The cutting tool position detection unit 16 that detects at least one of the position and the direction of the root canal treating hand piece 20 is provided. Owing to this, the position of the root canal treating hand piece 20 with respect to the target tooth (T) is detected, and the image of the root canal treating hand piece 20 is displayed on the monitor 13 in correspondence with the tooth image (I). Therefore, the operator can perform the surgical operation accurately while checking the monitor 13.

The operator does not need to view the tooth image (I) showing the position of the root canal orifice (Ro) or the like and the oral cavity of the patient (M1) in a switching manner, and can perform the surgical operation safely and accurately.

The medical care system 1 includes a predetermined operation unit that performs a predetermined operation when the cutting tool tip (26*a*) of the cutting tool 26 is detected by the cutting tool position detection unit 16 to be at a predetermined position in the root canal (R), or when the surgical operation direction is a predetermined direction with respect to the root canal extension direction at a predetermined position in the tooth (T). Owing to this, for example, when the cutting tool 26 is not at the predetermined position, or when the rotation axis of the cutting tool 26 is not in the predetermined direction, a notification is made in the form of, for example, voice, buzzer, melody, vibration, or illumination such as lighting or blinking of an LED or the like. Therefore, the operator can perform the surgical operation cautiously and carefully while being aware that the cutting tool 26 is at the predetermined position or that the rotation axis of the cutting tool 26 is in the predetermined direction. The cutting tool 26 is driven when the cutting tool 26 is at the predetermined position or when the rotation axis of the cutting tool 26 is in the predetermined direction. Therefore, the healthy area of the tooth (T) is prevented from being inadvertently cut away, or the cutting tool 26 is prevented from piercing the root apex (Rt).

The medical care system 1 includes the root canal length measurement device 40 that detects the position of the cutting tool tip (26a) of the cutting tool 26, and the root canal length measurement information storage unit (15d) that stores information on the root canal length detected by the root canal length measurement device 40. The predetermined operation unit performs the predetermined operation when the cutting tool tip (26a) is detected by the cutting tool position detection unit 16 to be at the predetermined position in the root canal (R) that is set based on the root canal length. Owing to this, for example, the operator can perform the surgical operation cautiously and carefully while being aware that the cutting tool tip (26a) of the cutting tool 26 is becoming close to the root apex (Rt). Even if the operator is not aware that the cutting tool tip (26a) is becoming close to the root apex (Rt), the root canal treating hand piece 20 is automatically controlled, for example, is stopped, driven at a decreased force, or rotated in a reverse direction. Therefore, the treatment can be performed safely.

The predetermined operation unit is the notification unit 25 that notifies that the cutting tool 26 is at the predetermined position in the root canal length of the root canal (R) or that the surgical operation direction is the predetermined direction with respect to the root canal extension direction at a predetermined position in the tooth (T). Owing to this, for example, when the root canal treating hand piece 20 is deviated from the root canal extension direction, or when the cutting tool tip (26a) of the cutting tool 26 attached to the root canal treating hand piece 20 is at a position that is arbitrarily set by the operator as the position several millimeters before the root apex (Rt), a notification is made in the form of, for example, voice, buzzer, melody, vibration, or illumination such as lighting or blinking of an LED or the like. Therefore, the operator can perform the surgical operation cautiously and carefully while being aware that the surgical operation direction is not correct or that the cutting tool tip (26a) of the cutting tool 26 is becoming close to the root apex (Rt).

The medical care system 1 includes the hand piece control unit 23 that controls the drive on the root canal treating hand piece 20. Owing to this, for example, when the root canal treating hand piece 20 is deviated from the root canal extension direction preset by the operator, or when the cutting tool tip (26a) of the cutting tool 26 attached to the root canal treating hand piece 20 is at a position that is arbitrarily set by the operator as the position several millimeters before the root apex (Rt), the root canal treating hand piece 20 is controlled, for example, is stopped, rotated in a reverse direction, or driven at a decreased force. Therefore, an unintended area in the root canal (R) is prevented from being inadvertently cut away by the cutting tool 26, or the cutting tool 26 is prevented from piercing the root apex (Rt) (so-called perforation is prevented). Therefore, the operator can perform the surgical operation safely.

The three-dimensional information of the present invention corresponds to the 3D information in the embodiment; and similarly, the tooth specification unit corresponds to the target tooth specification operation unit (12a);

the display unit corresponds to the monitor 13;

the arbitrary point specification unit corresponds to the root canal arbitrary point specification unit (12b);

the tooth cross-sectional image corresponds to the root canal cross-sectional image (ItC);

the visible light camera corresponds to the visible light camera 30 built in, or attached to, the root canal treating hand piece 20 or the microscope 70;

the surgical operation unit corresponds to the visible light camera-inclusive root canal treating hand piece 20;

the root canal treating unit corresponds to the medical care system 1;

the drive control unit corresponds to the hand piece control unit 23;

the detection unit corresponds to the cutting tool position detection unit 16;

the predetermined operation unit corresponds to the surgical operation cutting tool control unit (11g) and the notification unit 25; and the root canal length measurement unit corresponds to the root canal length measurement device 40.

The present invention is not limited to the above-described embodiment, and may be carried out in any of various other embodiments.

For example, in step (t3), in the above embodiment, the upper dental arch or the lower dental arch is selected by use of the jaw specification unit 260. Alternatively, the information on the patient (M1) that is read in step (t2) may include information indicating which of the upper jaw and the lower jaw include the target tooth (T). In this case, the upper dental arch or the lower dental arch may be automatically selected.

The positions of the display areas, showing the tooth image (I), in the root canal extension direction display operation screen 300 are not limited to those in the above embodiment. The display area such as the 3D root canal extension direction display area 310 may be changeable to at a position desired by the operator. Alternatively, one of the display areas may be displayed in an enlarged state whereas the other display areas may be displayed in a contracted state. These display areas may be switchable such that any of the other display areas is displayed in an enlarged state.

In the above embodiment, the two-dimensional converted images, which are each a cross-sectional image of the tooth (T), are displayed in the XZ plane root canal extension direction display area 330 or the YZ plane root canal extension direction display area 340. Alternatively, a side view of the tooth (T) may be displayed. In the above embodiment, the XY plane root canal extension direction display area 320 shows the two-dimensional converted image (ItP), which shows the tooth (T) as observed in the occlusal surface direction. Alternatively, a cross-sectional image of the tooth (T) taken along a plane parallel to the occlusal surface direction may be displayed in the XY plane root canal extension direction display area 320.

In the above embodiment, the XY cross-sectional position specification operation unit 331 is usable to specify the position of the tooth (T) along which the two-dimensional converted image (ItP) is to be displayed in the XY plane root canal extension direction display area 320. The XY cross-sectional position specification operation unit 331 may be used to display the two-dimensional converted image (ItP) taken along a plane including the position of the cutting tool tip (26*a*) of the cutting tool 26.

The root canal (R) and the root canal orifice (Ro) may be colored, and only the colored root canal (R) and root canal orifice (Ro) may be displayed on the tooth image (I) in an overlapping manner. The outline of the tooth (T) or the root canal orifice (Ro) may be emphasized and displayed on the tooth image (I) in an overlapping manner.

In the above embodiment, the size or the orientation of the two-dimensional converted image (ItP) of the tooth (T) as observed in the occlusal surface direction is adjusted to match the size or the orientation of the two-dimensional captured image (Ip) captured by the visible light camera 30. Alternatively, the size or the orientation of the two-dimensional captured image (Ip) may be adjusted to match the size or the orientation of the two-dimensional converted image (ItP). Still alternatively, the sizes or the orientations of both of the two-dimensional converted image (ItP) and the two-dimensional captured image (Ip) may be adjusted to match each other.

In the above embodiment, the cutting tool tip (26*a*) of the cutting tool 26 is detected by the cutting tool position detection unit 16. When the cutting tool tip (26*a*) is deviated from a certain range that is set based on the root canal extension direction, the hand piece control unit 23 restricts the drive on the root canal treating hand piece 20, or the position detection notification unit 251 of the notification unit 25 makes a notification in the form of, for example, a sound such as a buzzer or illumination. Alternatively, the root canal treating hand piece 20 may be controlled to drive the cutting tool 26, or the notification made by the position detection notification unit 251 of the notification unit 25 in the form of, for example, a sound such as a buzzer or illumination may be performed, when the cutting tool 26 reaches the predetermined position or when the direction of the rotation axis of the cutting tool 26 is the predetermined direction.

The cutting tool torque detection unit 28 measures the torque value directly or indirectly during the cutting performed on the root canal (R). When the torque value detected by the cutting tool torque detection unit 28 exceeds a predetermined value, the cutting tool 26 attached to the root canal treating hand piece 20 may be rotated in a reverse direction, stopped, or driven at a decreased force by the hand piece control unit 23.

In this case, the cutting tool 26 is prevented from eating into the root canal (R) or being broken.

In the field of dentistry, a root canal treatment is performed as follows. The tectorium of the tooth crown is removed by a high-speed cutting tool such as an air turbine or the like. Then, the tooth is cut away until the root canal orifice is seen. After the root canal orifice, which is a target of treatment, is visually recognized, a cutting tool for the root canal treatment such as a reamer or a file is inserted from the root canal orifice to perform the treatment.

In order to grasp the position of the root canal beforehand for the root canal treatment, CT image capturing is performed. According to the CT image capturing, a tooth as a target of interest is irradiated with an X-ray to collect projection data, and the acquired projection data is re-constructed on a computer to generate a computerized tomography image (volume rendering image, etc.).

The CT image capturing is performed as follows. A subject is located between an X-ray generator and an X-ray detector. While the X-ray generator and the X-ray detector are revolved around the subject, a cone-like X-ray is directed toward the subject from the X-ray generator. The X-ray detection results are collected by the X-ray detector, and three-dimensional data is re-constructed based on the collected X-ray detection results.

An X-ray CT image capturing device described in Japanese Laid-Open Patent Publication No. 2006-305203 displays a volume rendering image in addition to a cross-sectional image taken along each of X, Y and Z directions. An X cursor, a Y cursor and a Z cursor are operated to display cross-sections corresponding to the respective cursors.

In such CT image capturing, information on the tooth acquired by the X-ray transmitted through the tooth includes information on the root canal inside the tooth. Therefore, the position or the size of the root canal orifice, the root canal or the like, which cannot be visually recognized from the surface, can be shown.

However, an operator, performing a root canal treatment while checking an image captured by the optical camera or the microscope, needs to visually recognize, and accurately grasp, the position of the root canal orifice inside the tooth for a more accurate treatment. As described above, in order to allow the root canal orifice to be visually recognizable, an unintended area needs to be cut away.

Japanese Laid-Open Patent Publication No. 2009-153785 describes a system for the field of root canal treatment that displays a real-time image of an affected site and X-ray image data in a visually recognizable manner concurrently or displays medical check data such as root canal length measurement data or the like and a real-time image of an affected site in a visually recognizable manner concurrently. However, this system cannot display a direction in which the root canal extends as overlapping the real-time image of the affected image. As described above, in order to perform a root canal treatment, the position of the root canal orifice inside the tooth needs to be visually recognized and accurately grasped. Therefore, an unintended area needs to be cut away such that the root canal orifice is visually recognized.

For the root canal treatment, it is conceivable to apply, for example, a guide system described in Japanese Laid-Open Patent Publication No. 2012-96080 as a system that guides the cutting tool from the outside of the tooth crown to the root canal orifice inside the tooth.

Japanese Laid-Open Patent Publication No. 2012-96080 describes that the guide system for the cutting tool described therein operates as follows for a dental implantation surgery. A simulation is performed based on three-dimensional data on a tooth acquired by an X-ray CT image capturing device to create a template to be attached to the tooth. A guide hole used to guide the cutting tool is formed in the template. Thus, the cutting tool is guided.

However, the template to be used in the implant surgery is originally to make a straight hole in the jaw bone. Since the root canal is generally curved, it is difficult to make a hole in the root canal along the curved shaped thereof. Therefore, the operation of cutting an unintended area is unavoidable.

A root canal treating display device, a root canal treating unit and a dental image display method according to embodiments of the present invention show a direction in which a root canal treatment is to be performed and thus guide a cutting tool to a desired root canal so that a healthy area of a tooth to be cut is minimized.

A root canal treating display device according to an embodiment of the present invention includes a three-dimensional information storage unit that stores three-dimensional information including information on a root canal of teeth, the three-dimensional information being acquired by an X-ray CT image capturing device; a tooth specification unit that specifies a tooth as a target of interest; a tooth image processing unit that creates a tooth image of the tooth and displays the tooth image on the display unit; and a root canal extension direction processing unit that creates, based on the three-dimensional information, a root canal extension direction image showing a root canal extension direction along the root canal of the tooth, and displays the root canal extension direction image on the display unit as overlapping, and in correspondence with, the tooth image. The present invention is also directed to a display method using the root canal treating display device.

The concept represented by the "tooth image on the tooth" encompasses a three-dimensional image such as a CT image or the like that is created based on three-dimensional information, on a root canal of the tooth, that is acquired by the X-ray CT image capturing device; a cross-sectional image; a two-dimensional image; a two-dimensional captured image captured by a visible light camera; a three-dimensional visible light image captured by a stereo camera; and the like.

The concept represented by the "specification of the tooth" encompasses specification of a tooth from the tooth image created based on the three-dimensional information and displayed on the display unit; specification of a tooth by inputting the number of the tooth or the like; specification of a tooth based on another image such as an illustration of a dental arch displayed on the display unit; and specification of a tooth by any other appropriate method.

The root canal extension direction is a direction along the root canal. Specifically, the root canal extension direction may be along the shape of the root canal and extend from the root apex toward the outside of the tooth crown through the root canal orifice. For a surgical operation performed on an area from the outside of the tooth crown to the root canal orifice, the root canal extension direction may be a straight direction that is along the shape of the root canal and extends from the root canal orifice, which is an end of the root canal, toward the outside of the tooth crown. For a root canal treatment performed on an area from the root canal orifice to the root apex, the root canal extension direction may be a direction along the shape of the root canal, specifically, a direction in which the root canal extends from the position of the tip of the cutting tool used for the root canal treatment toward the root apex.

The concept represented by the "display of the root canal extension direction image" encompasses display of a root canal extension direction image that is straight, curved, bent or branched in accordance with the shape of the root canal.

The expression "display in an overlapping manner" indicates displaying the root canal extension direction image as overlapping the tooth image, with the size and the orientation of the root canal extension direction image being in correspondence with those of the tooth image.

According to an embodiment of the present invention, for the root canal treatment, the direction of the treatment is shown, and the cutting tool is guided to the desired root canal. Thus, the healthy area of the tooth that is cut away is minimized.

This is described in more detail. The root canal extension direction image, showing the direction that is along the root canal inside the tooth and passes the root canal orifice to extend toward the outside of the tooth crown or the direction in which the cutting tool is to be advanced toward the root apex, is created based on the three-dimensional information on the tooth acquired by the X-ray CT image capturing device. The root canal extension direction image is displayed on the display unit as overlapping, and in accurate correspondence with, the tooth image of the target tooth. Thus, the direction extending from the outside of the tooth crown of the target tooth toward the root canal orifice inside the tooth and further toward the root apex along the root canal is clearly displayed. Therefore, the entrance direction of the cutting tool that passes the root canal orifice to extend toward the root apex along the root canal is made clear. As can be seen, the root canal extension direction image showing the direction extending from the outside of the tooth crown toward the root canal orifice acts as a guide to introduce the cutting tool toward the root canal orifice. The root canal extension direction image showing the direction in which the root canal extends from the tip of the cutting tool in use toward the root apex acts as a guide to introduce the cutting tool toward the root apex. As a result, the entrance direction of the cutting tool into the root canal is made clear, and the cutting tool is accurately guided so as to be along the root canal of the target tooth.

Owing to this, the healthy area of the tooth that is cut away for treating the desired root canal is minimized.

In an embodiment of the present invention, the tooth image processing unit may create the tooth image of the specified tooth based on the three-dimensional information stored on the three-dimensional information storage unit.

According to an embodiment of the present invention, the tooth image showing the root canal orifice and the root canal, and the root canal extension direction image, are displayed on the display unit as overlapping, and in correspondence with, each other based on the three-dimensional information on the tooth acquired by the X-ray CT image capturing device. Therefore, the cutting tool is accurately guided to the root canal of the tooth. During the root canal treatment, the cutting tool is guided to the desired root canal, and the healthy area of the dentin that is cut away is minimized.

In an embodiment of the present invention, the root canal treating display device may further include an arbitrary point specification unit that accepts specification of an arbitrary point on the root canal. The root canal extension direction processing unit may create the root canal extension direction image based on the arbitrary point specified by use of the arbitrary point specification unit.

The concept represented by the "specification of the arbitrary point" encompasses specification of two or more arbitrary points on the root canal; specification of one point on the root canal and adjusting the angle based on the one point; and the like. The specification is performed in order to define the root canal extension direction.

According to an embodiment of the present invention, even in the case where the root canal has a complicated shape of, for example, being bent or branched, the arbitrary point may be specified along the shape of the root canal, so that the root canal extension direction along the root canal is appropriately set and displayed.

In an embodiment of the present invention, the arbitrary point specification unit may accept specification of multiple arbitrary points at a predetermined interval.

According to an embodiment of the present invention, the root canal extension direction is defined so as to pass the multiple arbitrary points. Therefore, the degree of freedom of the root canal extension direction is raised.

In an embodiment of the present invention, the arbitrary point specification unit may accept specification of, as a part of the arbitrary point (s), at least a position on a tooth crown where a cutting tool enters the tooth or a root canal orifice of the tooth.

According to an embodiment of the present invention, even in the case where, for example, there are multiple root canal orifices of the root canal, the root canal orifice of the root canal as the target of interest is accurately specified.

In an embodiment of the present invention, the tooth image processing unit may create, as the tooth image, a tooth cross-sectional image that shows a cross-section, of the tooth, including the root canal extension direction and is rotatable about the root canal extension direction, which is a rotation axis, and the tooth image processing unit may display the tooth cross-sectional image on the display unit, the root canal extension direction being straight.

According to an embodiment of the present invention, the root canal of the target tooth is displayed with a cross-section taken along a plane of any angle. Therefore, even in the case where the root canal has a complicated shape, the shape of the root canal can be easily recognized visually.

This is described in more detail. The root canal extension direction extends along the root canal. Therefore, the plane including the root canal extension direction includes a cross-section of the root canal. Thus, the shape of the root canal is displayed accurately.

This is described in more detail. A tooth cross-sectional image that shows a cross-section, of the tooth, including the root canal extension direction and is rotatable about the straight root canal extension direction, which is a rotation axis, is displayed. Owing to this, even in the case where the root canal has a complicated shape of, for example, being bent or branched three-dimensionally, the root canal cross-sectional image along the root canal is rotated about the rotation axis, namely, the straight root canal extension direction. As a result, for example, a cross-section including the bending direction of the root canal is displayed. Thus, the operator can accurately grasp the shape of the root canal. The root canal extension direction image is not limited to being straight or curved, and may have a width corresponding to the thickness of the root canal.

In an embodiment of the present invention, the root canal treating display device may further include a visible light camera that captures a visible light two-dimensional captured image of an occlusal surface of the tooth as the target of interest. The tooth image processing unit may create, as the tooth image, a two-dimensional converted image, which is a two-dimensional image that shows a predetermined plane parallel to the occlusal surface and is created based on the three-dimensional information, and the tooth image processing unit may display the two-dimensional captured image and the two-dimensional converted image on the display unit in correspondence with each other.

The occlusal surface is observed in the occlusal surface direction, namely, the tooth axis direction. More specifically, the concept represented by the "occlusal surface direction" encompasses a direction crossing the tooth axis at an angle in the range of ±30 degrees.

The predetermined plane is a plane crossing the tooth axis direction. The concept represented by the "predetermined plane" encompasses a cross-section passing the inside of the tooth, an invisible surface of the tooth, namely, an unexposed surface of the tooth, and a plane separated from the surface of the tooth.

The concept represented by the "visible light camera" encompasses a visible light camera attached to, or built in, the root canal treating hand piece to be integral therewith, an intraoral camera and a microscope separate from the root canal treating hand piece, and the like. The concept represented by the "two-dimensional capture image" encompasses a still image and also a moving image.

According to an embodiment of the present invention, the shape of the root canal inside the tooth, and the direction that is along the root canal and passes the root canal orifice, are clearly shown against the visible light two-dimensional captured image.

This is described in more detail. The visible light two-dimensional captured image of the target tooth captured in the occlusal surface direction, and the two-dimensional converted image created based on the three-dimensional information on the tooth and showing a predetermined plane, are displayed on the display unit in correspondence with each other. The three-dimensional information includes information on the root canal inside the tooth. The root canal extension direction image created based on the three-dimensional information is also displayed on the display unit as overlapping, and in accurate correspondence with, the two-dimensional captured image and the two-dimensional converted image.

In the case where the two-dimensional captured image is a moving image, the position or the direction of the root canal treating hand piece may detected, and the two-dimensional converted image, obtained based on the three-dimensional information acquired by the X-ray CT image capturing device, may be displayed as overlapping the two-dimensional captured image so as to follow the detected information.

Owing to this, the two-dimensional converted image, which is a two-dimensional image that is created based on the three-dimensional information and shows a predetermined plane, shows the position, the size or the like of the root canal orifice inside the tooth. The visible light two-dimensional captured image of the surface of the tooth and the two-dimensional converted image are displayed in an overlapping manner. In addition, the position, the size or the like of the root canal orifice inside the tooth is shown in the two-dimensional captured image. Therefore, while checking the two-dimensional captured image of the surface of the target tooth, the operator can grasp the position or the size of the root canal orifice inside the tooth, and also the direction that is along the root canal and passes the root canal orifice, namely, the direction in which the cutting tool is to be introduced.

In an embodiment of the present invention, the root canal extension direction processing unit may create, as the root canal extension direction image, a root canal extension direction converted image, which is a two-dimensional image of the root canal extension direction image and shows the predetermined plane, and the root canal extension direction processing unit may display the root canal extension direction converted image on the display unit in correspondence with the tooth image.

According to an embodiment of the present invention, the root canal extension direction image is displayed as overlapping the visible light two-dimensional captured image of the surface of the tooth, which is displayed as overlapping, or side by side with, the two-dimensional converted image created based on the three-dimensional information acquired by the X-ray CT image capturing device. Thus, the position or the size of the root canal, and also the root canal extension direction along the root canal inside the tooth, are clearly shown. Thus, the operator can perform the surgical operation accurately.

In an embodiment of the present invention, the root canal treating display device may further include a visible light camera that captures an image of an occlusal surface of the tooth as the target of interest. The tooth image processing unit may create, as the tooth image, a two-dimensional captured image of the occlusal surface of the tooth based on the image captured by the visible light camera.

According to an embodiment of the present invention, the two-dimensional captured image and the root canal extension direction image showing the direction toward the root canal orifice are displayed in an overlapping manner. The two-dimensional captured image is created based on the information captured by an intraoral camera such as, for example, the visible light camera built in the root canal treating hand piece or a visible light camera attached to the root canal treating hand piece, or the microscope. Since the two-dimensional captured image and the root canal extension direction image are displayed in an overlapping manner, the operator can visually recognize the direction toward the root canal orifice inside the target tooth in the actual treatment based on the two-dimensional captured image, and can perform the surgical operation safely and accurately.

In an embodiment of the present invention, the root canal treating display device may further include a cutting tool information storage unit that stores cutting tool information on a cutting tool to be used for a surgical operation on the tooth; a cutting tool specification unit that accepts specification of the cutting tool to be displayed on the display unit; and a cutting tool image processing unit that creates a cutting tool image based on the cutting tool information on the cutting tool specified by use of the cutting tool specification unit, and displays the cutting tool image on the display unit as overlapping, and in correspondence with, the tooth image.

The cutting tool is a cutting tool usable to cut the tectorium, dentin, dental pulp or the like of the target tooth. The concept represented by the "cutting tool" encompasses an air turbine usable to cut the tectorium, a reamer and a file usable for the root canal treatment, a cutting tool using ultrasonic waves or laser, and the like.

The concept represented by the "cutting tool information" encompasses information on the length, diameter of each of the cutting tools, the shape and rigidity of each of blades thereof, and the like. The concept represented by the "storage of the cutting tool information" encompasses storage of existing information on the cutting tool beforehand, storage of information on the cutting tool that is newly downloaded, storage of newly created information on the cutting tool, and the like.

The concept represented by the "specification of the cutting tool performed by use of the cutting tool specification unit" encompasses, for example, specification of the cutting tool performed by the operator at the time of the surgical operation; specification of the cutting tool performed based on the selection screen displayed on the display unit; specification of the cutting tool performed based on an identification signal read from an identification unit that is included in the surgical operation device to identify cutting tools; and the like.

The concept represented by the "display of the cutting tool" encompasses display of only the cutting tool, display of the cutting tool and a part of the surgical operation to which the cutting tool is attached, and display of the cutting tool and the entirety of the surgical operation device.

According to an embodiment of the present invention, an image of the cutting tool is displayed on the display unit as overlapping, and in correspondence with, the tooth image. For example, the image of the cutting tool may be displayed along the root canal extension direction. In this case, the operator can easily grasp the entrance direction of the cutting tool visually.

In an embodiment of the present invention, the root canal treating display device may further include an entrance route image processing unit that creates an entrance route image showing an entrance route of the cutting tool along the root canal based on the cutting tool information and the root canal extension direction, and displays the entrance route image on the display unit in correspondence with the tooth image.

According to an embodiment of the present invention, the entrance direction of the cutting tool is clearly shown so as to be visually recognizable. Therefore, the operator can perform the surgical operation accurately and safely.

This is described in more detail. Before performing the surgical operation, the operator can display the entrance route of the cutting tool along the root canal on the display unit based on the three-dimensional information on the tooth acquired by the X-ray CT image capturing device, the information on the cutting tool to be used for the surgical operation, and the root canal extension direction.

Therefore, before performing the surgical operation, the operator can visually recognize the state of the cutting tool entering the root canal along the root canal extension direction. The operator can determine whether or not to perform the surgical operation based on the displayed entrance route image. When the operator determines to perform the surgical operation, the operator causes the cutting tool to enter along the root canal extension direction. Thus, the healthy area of the tooth that is cut away is minimized, and the cutting tool is guided to the desired root canal.

In an embodiment of the present invention, the root canal treating display device may further include a permeability specification operation unit that accepts an operation of specifying a permeability level of at least a part of the images displayed on the display unit in an overlapping manner. The tooth image processing unit may create a permeable image that is made permeable in accordance with the permeability level specified by use of the permeability specification operation unit.

The concept represented by the "operation of specifying a permeability level" encompasses an operation of putting at least one of the images displayed in an overlapping manner into a semi-permeable state, and an operation of putting at least one of such images into a permeable or non-permeable state.

The concept represented by the "operation of specifying a permeability level of at least a part of the images" encompasses, for example, an operation of specifying that the entire image displayed on the display unit is to be semi-permeable; an operation of specifying that a part of the image, for example, the surgical operation device part of the cutting tool image, is to be semi-permeable, whereas the cutting tool part is to be non-permeable; and an operation of specifying that a part of the tooth image, displayed on the display unit based on the three-dimensional information, except for the root canal orifice and the root canal, is to be semi-permeable.

According to an embodiment of the present invention, for example, the root canal extension direction image may be made semi-permeable so that the position of the root canal orifice of the root canal is clearly shown against the tooth image while the root canal extension direction along the root canal is clearly shown. The visible light image may be made semi-permeable so that the root canal is clearly shown against the tooth image created based on the three-dimensional information. Alternatively, the tooth image may be made semi-permeable so that the visible light image is clearly shown. In this manner, one of the tooth image and the visible light image displayed in an overlapping manner is clearly shown against the other. Therefore, the operator can perform the treatment on the root canal more precisely and accurately. In addition, while one of the images is clearly shown, the other image may be made permeable or non-permeable. In this manner, the operator can perform the root canal treatment while mainly checking the image clearly shown.

In an embodiment of the present invention, the root canal treating display device may further include a color specification operation unit that accepts an operation of specifying a color of at least a part of the images displayed on the display unit in an overlapping manner. The tooth image processing unit may create a color image in accordance with the color specified by use of the color specification operation unit.

The concept represented by the "operation of specifying a color of at least a part of the images" encompasses an operation of specifying a color on the entirety of the images displayed on the display unit; and an operation of specifying a color on a part of the images, specifically, an operation of specifying a color on only the root canal area of the target tooth in the tooth image displayed on the display unit based on the three-dimensional information.

According to an embodiment of the present invention, for example, the root canal shown in the tooth image created based on the three-dimensional information is colored. In this manner, one of the tooth image and the visible light image displayed in an overlapping manner is clearly shown against the other. Therefore, the operator can perform the treatment on the root canal more precisely and accurately. The root canal may be shown with a color, and the tip of the cutting tool may be displayed as overlapping the tooth image based on an output from the detection unit or an output from the root canal length measurement device. In this case, the operator can perform the surgical operation while grasping, in real time, that the cutting tool is becoming close to the root apex. The area from the tip of the cutting tool to the root apex may be displayed with a color. In this case, the color of this area indicates the entrance direction of the cutting tool.

A root canal treating unit according to an embodiment of the present invention includes the above-described root canal treating display device; and a surgical operation device that performs a surgical operation on the tooth.

The concept represented by the "surgical operation device" encompasses hand pieces such as an air turbine hand piece, a motor hand piece, an ultrasonic hand piece, a laser hand piece, and the like.

According to an embodiment of the present invention, the operator can perform the surgical operation on the target tooth in the oral cavity while checking the direction toward the root canal orifice of the target tooth with the three-dimensional information and/or the two-dimensional captured image displayed on the display unit of the root canal treating display device.

In an embodiment of the present invention, a root canal treating unit may further include a driving unit that drives the cutting tool attached to the surgical operation device; and a drive control unit that controls drive on the driving unit. The drive control unit may perform the control in accordance with the cutting tool.

The concept represented by the "drive control" encompasses drive control on the cutting tool attached to the surgical operation device performed in a manner suitable to the cutting tool, drive control on the cutting tool performed based on a simulation result, and the like.

According to an embodiment of the present invention, the operator can perform the surgical operation safely and accurately.

This is described in more detail. Cutting tools are available in various types that are different in the length, the diameter or the shape. One type of cutting tool moves up and down to cut, and another type of cutting tool rotates to cut. Still another type of cutting tool rotates in a cutting direction and a non-cutting direction alternately. The drive control on the cutting tool is changed in accordance with the type thereof. Types of cutting tools different in the diameter or the length are often used for the root canal treatment. The degree of curving of the cutting tool is different in accordance with the type. Therefore, the drive control unit controls the cutting tool attached to the surgical operation device in accordance with the type thereof. Thus, the operator can perform the surgical operation safely and accurately.

In an embodiment of the present invention, the root canal treating unit may further include a detection unit that detects at least one of a surgical operation direction, with respect to the tooth, of the cutting tool attached to the surgical operation device, and a position of the surgical operation device.

The concept represented by the "surgical operation direction" encompasses a direction of the rotation axis of the cutting tool attached to the surgical operation device, a direction in which the laser is directed, a direction in which the ultrasonic wave is directed, and the like.

The above-described detection may be performed by, for example, a combination of calibration of matching the cutting tool attached to the surgical operation device to the target tooth and measurement by a gyrosensor built in the surgical operation device, three-dimensional position measurement on two or more points on the surgical operation device, a combination of measurement by a gyrosensor built in the surgical operation device and three-dimensional position measurement on at least one point on the surgical operation device, or a combination of two-dimensional position measurement on two or more points on the surgical operation device and measurement by a gyrosensor. The detection is not limited to direct position detection by the detection unit, and may encompass calculation of a position based on the results of detection performed by the detection unit. The three-dimensional position to be detected is not limited to an absolute three-dimensional position of the surgical operation device, and encompasses, for example, a relative three-dimensional position with respect to the target tooth.

The position may be measured by, for example, a three-dimensional position measurement method of detecting a three-dimensional position measurement marker, attached to the surgical operation device, by use of an infrared detector provided outside; a method of detecting a magnetic sensor, attached to the measurement target, by use of a three-dimensional magnetic detector; a method of measuring a three-dimensional position by use of infrared rays, or a method of measuring the position by use of a GPS device.

According to an embodiment of the present invention, the image of the cutting tool is displayed three-dimensionally on the display unit in correspondence with the tooth image displayed on the display unit.

This is described in more detail. The detection unit that detects at least one of the position and the direction of the surgical operation device is provided. Owing to this, the position of the surgical operation device with respect to the target tooth is detected, and the image of the surgical operation device is displayed on the display unit in correspondence with the tooth image. Therefore, the operator can perform the surgical operation accurately while checking the display unit.

The operator does not need to view the tooth image showing the position of the root canal orifice or the like and the oral cavity of the patient in a switching manner, and can perform the surgical operation safely and accurately.

In an embodiment of the present invention, the root canal treating unit may further include a predetermined operation unit that performs a predetermined operation when the position of the cutting tool attached to the surgical operation device, the position of which is detected by the detection unit, is a predetermined position in the root canal, or when the surgical operation direction is a predetermined direction with respect to the root canal extension direction at a predetermined position in the tooth.

The concept represented by "when the position of the cutting tool is a predetermined position" encompasses: when the position of the cutting tool is at a preset position that is several millimeters before the root apex; when the position of the cutting tool is deviated from a certain range expanding in the width direction from the root canal extension direction; and when the position of the cutting tool is included in the certain range.

The "predetermined direction" may be a direction in which the surgical operation direction is deviated from a certain angle range around the root canal extension direction.

The "predetermined operation" may be making a notification in the form of, for example, voice, buzzer, melody, vibration, or illumination such as lighting or blinking of an LED or the like; and performing drive control on the cutting tool, for example, stopping the drive on the cutting tool, lowering the output to drive the cutting tool, or rotating the cutting tool in a reverse direction.

According to an embodiment of the present invention, for example, when the cutting tool is not at the predetermined position, or when the rotation axis of the cutting tool is not in the predetermined direction, a notification is made in the form of, for example, voice, buzzer, melody, vibration, or illumination such as lighting or blinking of an LED or the like. Therefore, the operator can perform the surgical operation cautiously and carefully while being aware that the cutting tool is at the predetermined position or that the rotation axis of the cutting tool is in the predetermined direction. The cutting tool is driven when the cutting tool is at the predetermined position or when the rotation axis of the cutting tool is in the predetermined direction. Therefore, the healthy area of the tooth is prevented from being inadvertently cut away, or the cutting tool is prevented from piercing the root apex.

In an embodiment of the present invention, the root canal treating unit may further include a root canal length measurement unit that measures a position of a tip of the attached cutting tool; and a root canal length information storage unit that stores information measured by the root canal length measurement unit. The predetermined operation unit may perform the predetermined operation when the position of the tip of the cutting tool measured by the root canal length measurement unit is a predetermined position in the root canal.

The "predetermined operation" may be making a notification in the form of, for example, voice, buzzer, melody, vibration, or illumination such as lighting or blinking of an LED or the like; and performing drive control on the cutting tool, for example, starting or stopping the drive on the cutting tool, lowering the output to drive the cutting tool, or rotating the cutting tool in a reverse direction.

According to an embodiment of the present invention, for example, the operator can perform the surgical operation cautiously and carefully while being aware that the tip of the cutting tool is becoming close to the root apex based on an output from the root canal length measurement device. Even if the operator is not aware that the cutting tool is becoming close to the root apex, the cutting tool is automatically controlled, for example, is stopped, driven at a decreased force, or rotated in a reverse direction. Therefore, the treatment can be performed safely.

In an embodiment of the present invention, the predetermined operation unit may be a notification unit that notifies that the position of the cutting tool is a predetermined position with respect to a root canal length, or when a direction of the cutting tool is a predetermined direction with respect to the root canal extension direction at the predetermined position in the tooth.

According to an embodiment of the present invention, for example, when the surgical operation device is deviated from the root canal extension direction, or when the tip of the cutting tool attached to the surgical operation device is at a position that is arbitrarily set by the operator as the position several millimeters before the root apex, a notification is made in the form of, for example, voice, buzzer, melody, vibration, or illumination such as lighting or blinking of an LED or the like. Therefore, the operator can perform the surgical operation cautiously and carefully while being aware that the surgical operation direction is not correct or that the tip of the cutting tool is becoming close to the root apex.

In an embodiment of the present invention, the predetermined operation unit may be the drive control unit.

According to an embodiment of the present invention, for example, when the surgical operation device is deviated from the root canal extension direction preset by the operator, or when the tip of the cutting tool attached to the surgical operation device is at a position that is arbitrarily set by the operator as the position several millimeters before the root apex, the drive on the surgical operation device is controlled. Therefore, an unintended area in the root canal is prevented from being inadvertently cut away by the cutting tool, or the cutting tool is prevented from piercing the root apex (so-called perforation is prevented). Therefore, the operator can perform the surgical operation safely.

A root canal treating display device, a root canal treating unit and a dental image display method according to embodiments of the present invention show a direction in which a root canal treatment is to be performed and thus guide a cutting tool to a desired root canal so that a healthy area of a tooth to be cut is minimized.

Obviously, numerous modifications and variations of the present invention are possible in light of the above teachings. It is therefore to be understood that within the scope of the appended claims, the invention may be practiced otherwise than as specifically described herein.

The invention claimed is:
1. A root canal treatment information apparatus, comprising:
a computer including processing circuitry configured to store three-dimensional information including information on a root canal of teeth in a storage, the three- dimensional information being acquired by an X-ray CT image capturing device,
specify a tooth as a target of interest,
generate a tooth image of the tooth,
instruct display of the tooth image on a display,
generate, based on the three-dimensional information, a root canal extension direction image showing a root canal extension direction along the root canal of the tooth, and
instruct display of the root canal extension direction image on the display as overlapping, and in correspondence with, the tooth image thereby providing an indication of the angle in which a tool for root canal treatment is recommended to enter the tooth, the angle corresponding to two points defining a path of root canal extension direction image with respect to a curve of the root canal.

2. The root canal treatment information apparatus according to claim 1, wherein the circuitry is further configured to generate the tooth image of the specified tooth based on the three-dimensional information stored in the storage.

3. The root canal treatment information apparatus according to claim 2, wherein the circuitry is further configured to receive a designation of an arbitrary point on the root canal, and generate the root canal extension direction image based on the designated arbitrary point.

4. The root canal treatment information apparatus according to claim 3, wherein the circuitry is further configured to receive a designation of multiple arbitrary points at a predetermined interval.

5. The root canal treatment information apparatus according to claim 3, wherein the circuitry is further configured to receive the designation of, as the arbitrary point, one of a position on a tooth crown where a cutting tool enters the tooth or a root canal orifice of the tooth.

6. The root canal treatment information apparatus according to claim 2, wherein the circuitry is further configured to generate, as the tooth image, a tooth cross-sectional image that shows a cross-section, of the tooth, including the root canal extension direction and is rotatable about the root canal extension direction, which is a rotation axis, and to instruct display of the tooth cross-sectional image on the display, the root canal extension direction being straight.

7. The root canal treatment information apparatus according to claim 2, further comprising:
a visible light camera configured to capture a visible light two-dimensional captured image of an occlusal surface of the tooth as the target of interest,
wherein the circuitry is further configured to generate, as the tooth image, a two-dimensional converted image, which is a two-dimensional image that shows a predetermined plane parallel to the occlusal surface and is generated based on the three-dimensional info' cation, and to instnict display of the two-dimensional captured image and the two- dimensional converted image on the display in correspondence with each other.

8. The root canal treatment information apparatus according to claim 7, wherein the circuitry is further configured to generate, as the root canal extension direction image, a root canal extension direction converted image, which is a two-dimensional image of the root canal extension direction image and shows the predetermined plane, and to instruct display of the root canal extension direction converted image on the display in correspondence with the tooth image.

9. The root canal treatment information apparatus according to claim 2, wherein the circuitry is further configured to:
store cutting tool information on a cutting tool to be used for a surgical operation on the tooth in a cutting tool information storage;
accept specification of the cutting tool to be displayed on the display;
generate a cutting tool image based on the cutting tool information on the specified cutting tool; and
instruct display of the cutting tool image on the display as overlapping, and in correspondence with, the tooth image.

10. The root canal treatment information apparatus according to claim 9, wherein the circuitry is further configured to generate an entrance route image showing an entrance route of the cutting tool along the root canal based on the cutting tool information and the root canal extension direction, and to instruct display of the entrance route image on the display in correspondence with the tooth image.

11. A root canal treatment system, comprising:
the root canal treatment information apparatus according to claim 2; and
a surgical operation device configured to perform a surgical operation on the tooth.

12. The root canal treatment system according to claim 11, further comprising:
a motor that drives a cutting tool attached to the surgical operation device; and
control circuitry configured to control drive on the motor, wherein the control circuitry is further configured to control the drive in accordance with the cutting tool.

13. The root canal treatment system according to claim 11, further comprising:
a detector configured to detect at least one of a surgical operation direction, with respect to the tooth, of the cutting tool attached to the surgical operation device, and a position of the surgical operation device.

14. The root canal treatment system according to claim 13, wherein the control circuitry is further configured to instruct performance of a predetermined operation when the position of the cutting tool attached to the surgical operation device, the position of which is detected by the detector, is a predetermined position in the root canal, or when the surgical operation direction is a predetermined direction with respect to the root canal extension direction at a predetermined position in the tooth.

15. The root canal treatment system according to claim 14, further comprising:
a root canal length measurement sensor that measures a position of a tip of the attached cutting tool,
wherein control circuitry is further configured to store in a root canal length information storage information measured by the root canal length measurement sensor, and instruct performance of the predetermined operation when the position of the tip of the cutting tool measured by the root canal length measurement sensor is at a predetermined position in the root canal.

16. The root canal treatment system according to claim 14, wherein the predetermined operation is a notification that notifies that the position of the cutting tool is a predetermined position with respect to a root canal length, or that a direction of the cutting tool is a predetermined direction with respect to the root canal extension direction at the predetermined position in the tooth.

17. The root canal treatment system according to claim 14, wherein the predetermined operation is the control of the drive.

18. The root canal treatment information apparatus according to claim 1, further comprising:

a visible light camera that captures an image of an occlusal surface of the tooth as the target of interest,
wherein the circuitry is further configured to generate, as the tooth image, a two- dimensional captured image of the occlusal surface of the tooth based on the image captured by the visible light camera.

19. The root canal treatment information apparatus according to claim 1, wherein the circuitry is further configured to generate, as the tooth image, a tooth cross-sectional image that shows a cross-section, of the tooth, including the root canal extension direction and is rotatable about the root canal extension direction, which is a rotation axis, and to instruct display of the tooth cross-sectional image on the display, the root canal extension direction being straight, and
wherein the root canal extension direction image is also displayed above a crown area on the tooth image.

20. A dental image display method, comprising:
generating, using a computer and based on three-dimensional information, a root canal extension direction image showing a root canal extension direction along a root canal of a tooth by a root canal treatment information apparatus including circuity circuitry configured to store the three-dimensional information including information on the root canal of teeth in a storage, the three-dimensional information being acquired by an X-ray CT image capturing device, specify the tooth as a target of interest, generate a tooth image of the tooth, and instruct display of the tooth image on a display; and
displaying the root canal extension direction image on the display as overlapping, and in correspondence with, the tooth image thereby providing an indication of the angle in which a tool for root canal treatment is recommended to enter the tooth, the angle corresponding to two points defining a path of root canal extension direction image with respect to a curve of the root canal.

21. The dental image display method according to claim 20, further comprising:
generating the tooth image of the specified tooth based on the three-dimensional information stored in the storage.

22. The dental image display method according to claim 21, wherein the circuitry of the root canal treatment information apparatus is further configured to accept specification of an arbitrary point on the root canal of the specified tooth, and the displaying comprises displaying, on the display, the root canal extension direction image generated based on the specified arbitrary point, as overlapping, and in correspondence with, the tooth image.

23. The dental image display method according to claim 21, further comprising:
generating, as the tooth image, a tooth cross-sectional image that shows a cross-section, of the tooth, including the root canal extension direction and is rotatable about the root canal extension direction, which is a rotation axis; and
displaying the tooth cross-sectional image on the display, the root canal extension direction being straight.

24. The dental image display method according to claim 21, further comprising:
displaying, on the display, a two-dimensional captured image of an occlusal surface of the tooth as the target of interest captured by a visible light camera that captures a visible light image, and a two-dimensional converted image, which is a two-dimensional image that shows a predetermined plane parallel to the occlusal surface and is generated based on the three-dimensional information, in correspondence with each other.

25. The dental image display method according to claim 24, further comprising:
displaying, on the display, a root canal extension direction converted image, which is a two-dimensional image of the root canal extension direction image and shows a predeteimined plane, as overlapping, and in correspondence with, the tooth image.

* * * * *